(12) United States Patent
Striegel et al.

(10) Patent No.: US 6,936,632 B2
(45) Date of Patent: Aug. 30, 2005

(54) FUSED PYRROLE COMPOUNDS, PHARMACEUTICAL AGENTS CONTAINING THE SAME, AND THE USE THEREOF

(75) Inventors: Hans-Guenter Striegel, Blaustein (DE); Stefan Laufer, Blaubeuren (DE); Karola Tollmann, Brechen (DE); Susanne Tries, Ehingen (DE)

(73) Assignee: Merckle GmbH, Blaubeuren (DE)

( * ) Notice: Subject to any disclaimer, the term of this patent is extended or adjusted under 35 U.S.C. 154(b) by 61 days.

(21) Appl. No.: 10/169,988

(22) PCT Filed: Jan. 12, 2001

(86) PCT No.: PCT/EP01/00332

§ 371 (c)(1),
(2), (4) Date: Sep. 27, 2002

(87) PCT Pub. No.: WO01/51491

PCT Pub. Date: Jul. 19, 2001

(65) Prior Publication Data

US 2004/0122002 A1 Jun. 24, 2004

(30) Foreign Application Priority Data

Jan. 13, 2000 (DE) ......................................... 100 01 166

(51) Int. Cl.$^7$ ..................... A61K 31/403; C07D 209/02
(52) U.S. Cl. ...................................... 514/413; 548/516
(58) Field of Search .......................... 548/516; 514/413

(56) References Cited

U.S. PATENT DOCUMENTS

| | | | |
|---|---|---|---|
| 4,232,038 A | 11/1980 | Kluge et al. | |
| 5,260,451 A | 11/1993 | Dannhardt et al. | |
| 5,939,415 A | 8/1999 | Laufer et al. | |
| 5,942,535 A | * 8/1999 | Laufer et al. | ............... 514/413 |
| 5,958,943 A | 9/1999 | Laufer et al. | |
| 6,136,839 A | * 10/2000 | Isakson et al. | ............... 514/406 |

FOREIGN PATENT DOCUMENTS

| | | |
|---|---|---|
| DE | 196 24 289 A1 | 1/1998 |
| DE | 196 24 290 A1 | 1/1998 |
| DE | 198 45 446 A1 | 4/2000 |
| EP | 0 087 629 A2 | 9/1983 |
| WO | WO 94/15932 A1 | 7/1994 |
| WO | WO 94/27980 A1 | 12/1994 |
| WO | WO 95/00501 A2 | 1/1995 |
| WO | WO 95/11883 A1 | 5/1995 |
| WO | WO 95/15315 A1 | 6/1995 |
| WO | WO 95/21817 A1 | 8/1995 |
| WO | WO 95/30656 A1 | 11/1995 |
| WO | WO 96/10012 A1 | 4/1996 |
| WO | WO 99/61016 A1 | 12/1999 |
| WO | WO 01/05792 A1 | 1/2001 |
| WO | WO 01/57042 A2 | 8/2001 |

OTHER PUBLICATIONS

Yoshida Zenichi (1978): STN International CAPLUS database (Columbus, Ohio), document No. 89:109069.*
Dannhardt, G., et al., "Aminomethylierung und Arylthiolierung von 6.7–Diaryl–2.3–dihydro–1H–pyrrolizinen", Arch. Pharm., vol. 319, pp. 65–69 (1986).
Dannhardt, G., et al., "Oxidative Ringöffnung von 6.7–Diphenyl–2.3–dihydro–1H–pyrrolizin (DADHP) durch m–Chlorperbenzoesäure", Arch. Pharm., vol. 319, pp. 231–234 (1986).
Dannhardt, G., et al., "Synthese und Oxidation von 6.7–Diphenyl–2.3–dihydro–1H–pyrrolizin–5–yl–acetaldehyd (DADHP–5–acetaldenhyd)", Arch. Pharm., vol. 319, pp. 500–505 (1986).
Dannhardt, G., et al., "6.7–Diarylsubstituierte 1– und 3–Pyrrolizinone (1–DAPON und 3–DAPON)", Arch. Pharm., vol. 319, pp. 749–755 (1986).
Dannhardt, G., et al., "Natriummetaperiodat–Oxidation von 6.7–Diphenyl–2.3–dihydro–1H–pyrrolizin", Arch. Pharm., vol. 318, pp. 661–663 (1985).
Dannhardt, G., et al., "C–5 Functionalized 6,7–Diphenyl–2, 3–dihydro–1H–pyrrolizines as Inhibitors of Bovine Cyclooxygenase and 5–Lipoxygenase", Arch. Pharm., vol. 327, pp. 509–514 (1994).
Dannhardt, G., et al., "6.7–Diaryl–2.3–dihydro–1H–pyrrolizine (DADHP) als Singulett–Sauerstoff–Fänger", Arch. Pharm., vol. 318, pp. 663–664 (1985).
Dannhardt, G., et al., "E–2–Pyrrolizin–5–yl Acrylic Acids as Potent Dual or Selective Inhibitors of Bovine Cyclooxygenase and 5–Lipoxygenase", Arch. Pharm., vol. 328, pp. 681–686 (1995).
"Antiinflammatory Cyclooxygenase and 5–Lipooxygenase Inhibitor", Drugs of the Future, vol. 20, pp. 1007–1009 (1995).

(Continued)

Primary Examiner—Golam M M Shameem
(74) Attorney, Agent, or Firm—Rothwell, Figg, Ernst & Manbeck, PC

(57) ABSTRACT

The present invention relates to fused pyrrole compounds of the formula 1.

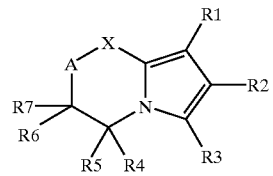

Formula 1 in which at least one of the radicals R1, R2, R3 is 4-sulphur-substituted phenyl.

These compounds are in particular pyrrolizines, indolizines and heteroanalogues having selective inhibitory action on isoenzyme-2 of prostaglandin H synthase (COX-2). The invention also relates to pharmaceutical compositions which contain these compounds; and the use of these compounds for the treatment of disorders of the rheumatic type.

14 Claims, 11 Drawing Sheets

OTHER PUBLICATIONS

Laufer, S., et al., "Synthesis and Evaluation of a Novel Series of Pyrrolizine Derivatives as Dual Cyclooxygenase–1 and 5–Lipoxygenase Inhibitors", *Arch. Pharm.*, vol. 330, pp. 307–312 (1997).

Laufer, S., et al., "(6,7–Diaryldihydropyrrolizin–5–yl)acetic Acids, a Novel Class of Potent Dual Inhibitors of Both Cyclooxygenase and 5–Lipoxygenase", *J. Med. Chem.*, vol. 37, pp. 1894–1897 (1994).

Muchowski, J., et al., "Synthesis and Antiinflammatory and Analgesic Activity of 5–Aroyl–1,2–dihydro–3H–pyrrolo[1, 2–a] pyrrole–1–carboxylic Acids. The 6–Substituted Compounds", *J. Med. Chem.*, vol. 30, pp. 820–823 (1987).

Wilkerson, W., et al., "Antiinflammatory 4,5–Diarylpyrroles: Synthesis and QSAR", *J. Med. Chem.*, vol. 37, pp. 988–998 (1994).

Wilkerson, W., et al., "Antiinflammatory 4,5–Diarylpyrroles. 2. Activity as a Function of Cyclooxygenase–2 Inhibition", *J. Med. Chem.*, vol. 38, pp. 3895–3901 (1995).

\* cited by examiner

Fig. 1

| Example No. | Structure | Mp [°C] | IR 1/λ [cm⁻¹] | 1H-NMR (Solvent): δ [ppm] | 13C-NMR (Solvent): δ [ppm] |
|---|---|---|---|---|---|
| 1 | [structure: phenyl-pyrrole with SCH₃-phenyl] | 112 | 3050, 1695, 1595, 1521, 1484, 1335, 1179, 1003 | (CDCl₃): 7.25- 7.10 (m, 9H, 2 arom), 6.72 (s, 1H, H-5), 3.98 (t, 2H, CH₂), 2.96 (t, 2H, CH₂), 2.50 (quin, 2H, CH₂), 2.44 (s, 3H, SCH₃) | |
| 2 | [structure: phenyl-pyrrole with SOCH₃-phenyl] | 208.8 | 2912, 1586, 1457, 1301, 1140, 1088, 959, 829, 774. | (CDCl₃): 7.93-7.64 (AA'BB', 4H, arom), 7.53 - 7.40 (5H, arom), 4.88 (s, 1H, H-3), 4.23 (t, 2H, CH₂), 3.16 (t, 2H, CH₂), 3.08 (s, 3H, SOCH₃), 2.65 (quin, 2H, CH₂), | |
| 3 | [structure: phenyl-pyrrole with SO₂CH₃-phenyl] | 164.9 | 3172, 1590, 1311, 1148, 951, 771 | (CDCl₃): 7.78 - 7.37 (AA'BB', 4H, arom), 7.37 - 7.20 (m, 5H, arom), 6.86 (s, 1H, H-3), 4.05 (t, 2H, CH₂), 3.05 (s, 3H, SO₂CH₃), 2.50 (quin, 2H, CH₂). | |
| 4 | [structure: F-phenyl-pyrrole with SO₂CH₃-phenyl] | -dec | | (CDCl₃): 7.27 - 6.89 (AA'BB'+ m, 8H, arom+ F-arom), 6.74 (s, 1H, H-5), 4.01 (t, 2H, CH₂), 2.93 (t, 2H, CH₂), 2.53 (quin, 2H, CH₂), 2.46 (s, 3H, SCH₃) | |
| 5 | [structure: F-phenyl-pyrrole with SO₂CH₃-phenyl] | 169.10 | 2924, 1592, 1528, 1502, 1404, 1307, 1215, 1152, 1090, 948, 841, 766 | (CDCl₃): 7.78 - 7.74 / 7.39 - 7.34 (AA'BB', 4H, arom), 7.29 - 6.92 (m, 4H, F-arom), 6.85 (s, 1H, CH), 4.055 (t, 2H, CH₂), 3.05 (s, 3H, CH₃), 2.94 (t, 2H, CH₂), 2.56 (quin, 2H, CH₂) | |
| 6 | [structure: SCH₃-phenyl-pyrrole with F-phenyl] | oily | 3424, 2918, 1691, 1596, 1493, 1402, 1223, 1156, 1090, 837 | (CDCl₃): 7.25 - 7.10 (AA'BB'+m, 6H, arom), 7.00- 6.85 (m, 2H, F-arom), 4.008 (t, 2H, CH₂), 2.960 (t, 2H, CH₂), 2.523 (quin, 2H, CH₂), 2.461 (s, 3H, SCH₃), | |

Fig. 2

| | | | | |
|---|---|---|---|---|
| 7 | [structure: pyrrolizine with SO2CH3-phenyl and F-phenyl] | | 2924, 1593, 1535, 1308, 1219, 1149, 954, 839, 776, 554, 537 | (CHCl3/DMSO): 7.78 – 7.74 (AA':2H, SO2CH3,arom-7); 7.34 -6.9 (m, BB', 2H, SO2CH3 arom-7, + m, 4H, F-arom), 6.73 (s, 1H, pyrroliz.); 4.045 (t, 2H, CH2, J=7.1); 3.087 – 2.95 (m, 5H, CH3, CH2), 2.60 (quin, 2H, CH2). | |
| 8 | [structure: pyrrole with SO2CH3-phenyl, F-phenyl, CH3] | 190-192 | 3440, 2975, 1591, 1533, 1500, 1302, 1215, 1152, 844, 772. | (CDCl3): 7.72 – 7.68 (AA', 2H, arom), 7.25 – 7.00 (BB'+AA'BB', 6H, arom), 3.97 (t, 2H, CH2), 3.05 (t, s, 5H, CH2 + CH3,), 2.65 – 2.5 (quin, 2H, CH2), 2.02 (s, 3H, CH3), | |
| 9d | [structure: pyrrolizine with F-phenyl and SCH3-phenyl] | | 2918, 1524, 1504, 1215, 830, 805, 520 | (CDCl3):7.5–6.9 (8H, m, arom) 4.0 (2H, t, J=6.9Hz) 2.88 (2H, t, J=7.3Hz) 2.53-2.50 (2H, m, CH2) 2.45 (3H, s, CH3) 2.03 (3H, s, CH3) | 161.1 (d, C-F, J=240 Hz), 137.5, 135.8, 132.6 (d, J=3.2 Hz), 131.6 (d, J = 4 Hz), 129.8, 129.1, 126.3, 124.9, 114.9 (d, J = 21 Hz), 108.5, 46.3, 27.3, 23.3, 15.7, 10.2. |
| 10 | [structure: pyrrolizine with SO2NH2-phenyl and F-phenyl] | 206.9 | 3355, 3048, 1596, 1403, 1321, 1151 | (d3-MEOD): 7.86 – 7.81 (AA', 2H, SO2NH2-arom), 7.66-7.62 (BB', 2H, SO2NH2-arom), 7.60-7.50 (m, 2H), 7.16 – 7.07 (m, 2H), 6.74 (s, 1H, H-1), 4.16 (t, 2H, J=7.1Hz, CH2), 3.18 – 3.10 (t, 2H, J=7.2Hz, CH2), 2.62 (quin, 2 H, CH2, J=7.2Hz) | 163.4/158.6 (d), 139.7, 138.4, 136.7, 128.7/128.5 (d), 127.1, 127.0/126.2 (d), 124.2, 115.4, 115.0/114.2 (d), 108.0, 46.1, 27.3, 25.2 |
| 11 | [structure: pyrrole with SCH3-phenyl, F-phenyl, CO2CH2CH3] | oily | | (CDCl3): 8.01-7.94 / 6.98-6.89 (AA'BB', 4H, arom), 7.13 (s, 4H), 4.17-4.08 (q, u, t, 4H, OCH2CH3 + CH2), 3.98 (t, J=7.1Hz, 2H), 3.21 (t, J=7.5Hz, 2H), 2.54 (quin, J=7.4Hz, 2H), 2.31 (s, CH3), 1.20 (t, J=7.2Hz, OCH2CH3) | |

Fig. 3

| | Structure | mp | IR | NMR | 13C NMR |
|---|---|---|---|---|---|
| 12 | 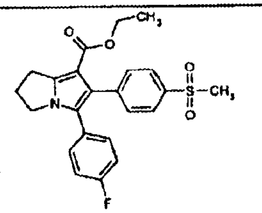 | oily | | (CDCl₃): 7.80 - 7.76 / 7.43 - 7.38 (AA'BB', 4H, arom), 7.09 - 6.96 (m, 4H, arom), 4.17 (q, J=7.1Hz, 2H, OCH₂CH₃), 3.99 (t, J=7.2Hz, 2H, CH₂), 3.23 (t, J=7.4Hz, 2H, CH₂), 3.05 (s, SO₂CH₃), 2.63-2.49 (quin, J=7.2Hz, 2H, CH₂), 1.26-1.19 (t, J=7.0Hz, OCH₂CH₃). | |
| 13 A | 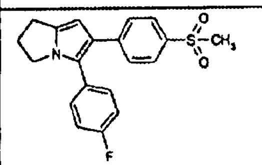 | 153.70 | 1591, 1525, 1509, 1301, 1223, 1148, 1091, 956, 843, 769, 547. | (CDCl₃): 7.75 - 7.71 / 7.39 - 7.35 (AA'BB', 4H, SO₂CH₃-arom), 7.28 - 7.21 (m, 2H, F-arom), 7.10 - 7.01 (m, 2H, F-arom), 6.12 (s, CH), 3.91 (t, J=6.9Hz, CH₂), 3.04 (s, SO₂CH₃), 2.96 (t, J=7.3Hz, CH₂), 2.50 (quin, J=7.2Hz, CH₂). | 164.6, 159.6, 143.0, 137.7, 136.4, 131.2, 128.8, 128.7, 128.0, 127.4, 125.1, 124.1, 116.1, 115.6, 100.2, 45.9, 44.6, 27.4, 24.5 |
| 13 B | 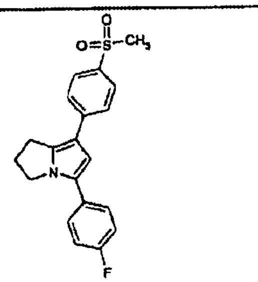 | 176.00 - 179.00 | 1594, 1525, 1488, 1302, 1223, 1146, 1092, 971, 959, 836, 791, 769. | (CDCl₃): 7.91-7.86 / 7.66-7.61 (AA'BB', 4H, SO₂CH₃-arom), 7.48-7.41 (m, 2H, F-arom), 7.16-7.05 (m, 2H, F-arom), 6.67 (s, CH), 4.15 (t, J=7.1 Hz, CH₂), 3.17 (t, J=7.3 Hz, CH₂), 3.07 (s, SO₂CH₃), 2.65 (quin, J=7.2 Hz, CH₂). | 164.1, 159.2, 142.0, 137.6, 135.7, 129.3, 129.0, 128.9, 127.9, 17.7, 127.6, 125.1, 116.0, 115.5, 114.5, 108.6, 46.6, 44.7, 27.8, 25.8. |
| 24 | 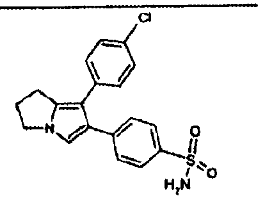 | 128-138°C dec | 3432, 3178, 3055, 1596, 1547, 1489, 1445, 1426, 1384, 1288, 1185, 1091, 1042, 833, 731, 721, 637 | (DMSO-d6):7.24-7.17 (m,5H.arom), 7.09-6.89 (AA'BB', 4H, arom), 4.87 (s, 2H, SO₂NH₂), 4.30 (t, 2H, CH₂), 2.965 (t, 2H, CH₂), 2.52 (quin.2H.CH₂) | |

Fig. 4

| | Structure | mp | IR | ¹H NMR | ¹³C NMR |
|---|---|---|---|---|---|
| 20 | [structure: pyrrolizine with 4-sulfamoylphenyl and 4-chlorophenyl] | dec | 3427, 2957, 2897, 1596, 1525, 1486, 1393, 1219, 1186, 1128, 1011, 835, 635 | (DMSO-d6):7.7-7.66 (AA'', 2H, arom), 7.20-7.10 (m, 7H, arom), 4.89 (s, 2H, SONH₂), 4.02 (t, 2H, CH₂), 2.935 (t, 2H, CH₂), 2.53 (quin, 2H, CH₂). | |
| 10 | [structure: pyrrolizine with I, 4-sulfamoylphenyl and 4-fluorophenyl] | 206.9 | 3355, 3048, 1596, 1403, 1321, 1151 | (d3-MEOD): 7.86-7.81 (AA', 2H), 7.66-7.61 (BB', 2H), 7.62-7.50 (m, 2H, F-aromat), 7.20-7.05 (m, 2H, F-arom), 6.74 (s, 1H), 4.156 (t, 2H, J=7.1Hz), 3.141 (t, 2H, J=7.2Hz), 2.62 (quin.2H). | 163.4, 158.6, 139.7, 138.4, 136.7, 128.7, 128.5, 127.1, 127.0, 126.2, 124.2, 115.4, 115.0, 114.2, 108.0, 46.1, 27.3, 25.2 |
| 21 | [structure: pyrrolizine with CH₃, 4-sulfonyl and 4-chlorophenyl] | | 3335, 3255, 1595, 1489, 1340, 1164, 835, 749, 547 | (DMSO-d6): 7.83 - 7.79 (AA', 2H, arom), 7.28 - 6.95 (m, 6H, BB' + Cl-arom), 4.77 (s, 2H, NH₂), 3.955 (t, 2H, CH₂), 2.99 (t, 2H, CH₂), 2.56 (quin, 2H, CH₂), 2.26 (s, 3H, CH₃). | |
| 17 | [structure: pyrrolizine with CH₃, 4-sulfamoylphenyl and 4-chlorophenyl] | 150 | 3336, 3260, 1596, 1433, 1426, 1315, 1160, 1118, 1093, 836, 727, 603, 548 | (DMSO-d6): 7.72 (AA', 2H, arom), 7.27-7.04 (m.6H, BB' + Cl-arom), 3.955 (t, 2H.-CH₂), 3.03 (t, 2H.-CH₂), 2.59 (quin, 2H, -CH₂), 2.21 (s, 3H, -CH₃) | |
| 15 | [structure: pyrrolizine with CH₃, 4-sulfamoylphenyl and 4-fluorophenyl] | 120 | 3350, 3266, 1595, 1538, 1501, 1220, 1160, 836, 604, 549 | (DMSO-d6): 7.71-7.67 (AA', 2H, arom), 7.25-6.94 (m, 6H, BB'+F-arom), 4.79 (s, 2H, NH₂), 3.95 (t, 2H, CH₂), 3.04 (t, 2H, CH₂), 2.57 (quin, 2H, CH₂), 2.2 (s, 3H, CH₃). | |

Fig. 5

| | | | |
|---|---|---|---|
| 26 | 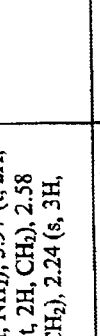 | 211 | 3405, 3345, 3288, 2955, 1595, 1543, 1333, 1301, 1200, 1128, 904, 706, 612 | 7.73-7.69 (AA', 2H, arom), 7.49-7.26 (BB'+AA', 4H, arom), 7.17-7.13 (BB', 2H, arom), 4.77 (s.broad, 2H, NH$_2$), 3.97 (t, 2H, CH$_2$), 3.06 (t, 2H, CH$_2$), 2.58 (quin, 2H, CH$_2$), 2.24 (s, 3H, CH$_3$) |
| 28 | 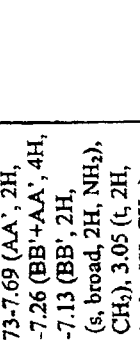 | 201 | 3405, 3345, 3288, 2955, 1595, 1534, 1333, 1301, 1128, 904, 706, 612 | (CDCl$_3$): 7.73-7.69 (AA', 2H, arom), 7.49-7.26 (BB'+AA', 4H, arom), 7.17-7.13 (BB', 2H, arom), 4.77 (s, broad, 2H, NH$_2$), 3.97 (t, 2H, CH$_2$), 3.05 (t, 2H, CH$_2$), 2.58 (quin, 2H, CH$_2$), 2.24 (s, 3H, CH$_3$) |
| 29 A | 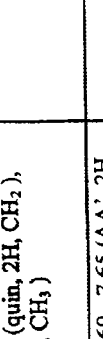 | 152-154 | 3364, 3264, 1594, 1324, 1162, 604 | (CDCl$_3$): 7.69 - 7.65 (AA', 2H, arom), 7.18 - 7.13 (BB', 2H, arom), 7.12 - 7.00 (AA'BB', 4H, arom), 3.96 (t, 2H, CH$_2$), 3.04 (t, 2H, CH$_2$), 2.59 (quin, 2H, CH$_2$), 2.35 (s, 3H, CH$_3$), 2.21 (s, 3H, CH$_3$) |
| 29 B | 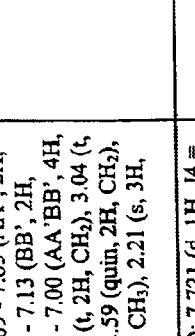 | 218-219 | 3381, 3261, 2924, 1594, 1543, 1326, 1161, 904, 835, 605 | (DMSO-d6): 7.721 (d, 1H, J4 = 1.4 Hz, H-2'), 7.70 - 7.55 (AA', 2H, arom-1), 7.378 (br, 2H, SO$_2$NH$_2$), 7.252 (d, 1H, J3 = 8.0 Hz, H-5'), 7.213 (br, 2H, SO$_2$NH$_2$), 7.20 - 7.04 (BB', 2H, arom-1), 7.026 (dd, 1H, J3 = 7.7 Hz, J4 = 1.5 Hz, H-6') 3.956 (t, 2H, J = 7.0 Hz, CH$_2$), 2.985 (t, 2H, J = 7.0 Hz, CH$_2$), 2.575 (s, 3H, CH$_3$-4'), 2.500 (quin, 2H, CH$_2$, J = 7.0 Hz), 3.156 (s, 3H, CH$_3$-3) |

Fig. 6

| # | Structure | mp | IR | NMR |
|---|---|---|---|---|
| 25 | | 2.57-259 | 3421, 3270, 2957, 1549, 1536, 1488, 1430, 1321, 1162, 1092, 827, 610, 550 | 7.65 - 7.60 (AA', 2H, arom), 7.27 - 7.22 (BB', 2H, arom), 7.11 - 7.04 (AA'BB', 4H, Cl-arom), 3.70 (s, 2H, CH$_2$), 2.84 (s, 2H, CH$_2$), 2.17 (s, 3H, CH$_3$), 1.31 (s, 6H, CH$_3$) |
| 18 | | dec, from 320 | 3248, 2980, 1589, 1518, 1375, 1311, 1163 | (d3-MeOD): 7.63 - 7.59 (AA', 2H, arom), 7.27-7.11 (AA'BB', 4H, arom), 7.08 - 7.04 (2H, arom), 4.87 (s, SO$_2$NH$_2$-exchange), 4.37 (t, 2H, CH$_2$), 4.08 (q., 2H, OCH$_2$CH$_3$), 3.03 (t, 2H, CH$_2$), 2.649 (quin, 2H, CH$_2$), 1.12-1.05 (t, 3H, OCH$_2$CH$_3$). |
| 22 | | dec, from 110 | 3265, 2981, 1688, 1542, 1464, 1419, 1382, 1312, 1227, 1163, 1098 | (CDCl$_3$): 7.73 - 7.68 (AA', 2H, arom), 7.27 - 7.23 (BB', 2H, arom), 7.04 - 7.00 (AA', 2H, arom), 6.81 - 677 (BB', 2H, arom), 4.30 (t, 2H, CH$_2$), 4.02 (q., 2H, OCH$_2$CH$_3$), 2.91 (t, 4H, CH$_2$ + SO$_2$NH$_2$), 2.49 (quin, 2H, CH$_2$), 0.99 (t, 3H, OCH$_2$CH$_3$). |
| 19 | | | 3448, 3177, 1693, 1463, 1452, 1440, 1397, 1313, 1221, 1186, 1134, 1095, 1036, 1008 | (d3-MeOD): 7.63-7.59 (AA', 2H, arom), 7.26 - 7.10 (AA'BB', 4H, arom), 7.06 - 7.02 (BB', 2H, arom), 4.87 (s, SO$_2$NH$_2$-exchange), 4.37 (t, 2H, CH$_2$), 3.62 (s, 3H, COOCH$_3$), 3.02 (t, 2H, CH$_2$), 2.63-2.56 (quin, 2H, CH$_2$) |
| 23 | | dec, from 140 | 3022, 2951, 2886, 1708, 1596, 1545, 1488, 1459, 1399, 1220, 1121, 1098, 833 | (CDCl$_3$): 7.29 - 7.17 (AA'BB', 4H, arom), 7.14 - 7.10 (AA', 2H, Cl-arom), 6.94 - 6.89 (BB', 2H, Cl-arom), 4.39 (t, 2H, CH$_2$), 3.63 (s, 3H, COOCH$_3$), 3.00 (t, 2H, CH$_2$), 2.555 (t, 2H, CH$_2$). |

Fig. 7

| | Structure | mp | IR | ¹H NMR | ¹³C NMR |
|---|---|---|---|---|---|
| 16 | [structure: sulfonamide-phenyl pyrrolizine with 4-fluorophenyl] | 167°C dec | 3376, 3269, 1597, 1529, 1396, 1329, 1224, 1163, 1087, 839 | (CDCl₃): 7.75-7.71 / 7.33-7.00 (m, 8H, arom), 5.30 (s, 2H, NH₂), 4.04 (t, 2H, J=7.1Hz, CH₂), 3.05 (t, 2H, J=7.3Hz, CH₂), 2.58 (quin, 2H, CH₂) | 163.8, 158.9, 139.7, 138.9, 134.5, 131.4, 131.3, 129.7, 129.6, 127.9, 126.0, 120.9, 115.3, 114.8, 113.4, 45.5, 39.4, 26.4, 25.4. |
| 27 | [structure: sulfonamide-phenyl pyrrolizine with 4-CF₃-phenyl, Cl] | 94-97 | 3405, 3205, 1615, 1596, 1324, 1163, 1122, 1107, 1064, 849, 595, 550 | (d3-MeOD): 7.77 – 7.73 (AA', 2H, arom), 7.57 - 7.53 (BB', 2H, arom), 7.35 - 7.31 (AA', 2H, arom), 7.18 – 7.14 (BB', 2H, arom), 4.88 (s, br, 2H, exchange-NH₂), 4.058 (t, 2H, CH₂), 3.045 (t, 2H, CH₂), 2.595 (quin, 2H, CH₂) | |
| 34 | [structure: sulfonamide-phenyl pyrrolizine with CF₃] | 153.5 | 3388, 3282, 1594, 1536, 1296, 1198, 1149, 1091, 1079, 796, 598 | (CDCl₃): 7.95-7.44 (AA'BB', 4H, arom), 7.04 (s, 1H, CH), 4.03 (t, 2H, CH₂), 2.96 (t, 2H, CH₂), 2.57 (quin, 2H, CH₂) | 142.9, 134.5, 131.8, 128.7, 128.3, 126.1, 125.6, 123.5, 115.3, 46.7, 27.3, 24.1 |
| 30 | [structure: sulfonamide-phenyl pyrrolizine with Br] | 198-207 (dec) | 3348, 3256, 1596, 1528, 1430, 1327, 1302, 1151, 1055, 1095, 836, 543, 412. | (CDCl₃): 7.72-7.49 (AA'BB', 4H, arom), 7.20 (NH₂), 6.23 (s, 1H, CH), 3.88-3.81 (t, 2H, CH₂), 3.03 (t, 2H, CH₂), 2.49 (quin, 2H, CH₂), 2.17 (s, 3H, CH₃) | 134.0, 127.1, 126.5, 126.1, 125.0, 124.2, 113.0, 107.1, 44.0, 27.3, 25.8, 11.6. |

Fig. 8

| # | Structure | mp (°C) | IR (cm⁻¹) | ¹H NMR | ¹³C NMR |
|---|---|---|---|---|---|
| 31 | (structure) | 185-190 (dec) | 3353, 3259, 1724, 1591, 1524, 1428, 1323, 1158, 1091, 891, 836. | CDCl$_3$/DMSO-d6: 7.85-7.44 (AA'BB', 4H, arom), 4.09 (NH$_2$), 3.89 (t, 2H, CH$_2$), 2.98 (t, 2H, CH$_2$), 2.51 (quint, 2H, CH$_2$), 2.18 (s, 3H, CH$_3$), 2.14 (s, 3H, CH$_3$) | |
| 32 | (structure) | 230-240 (dec) | 3393, 3275, 2921, 2834, 2362, 1732, 1598, 1532, 1429, 1327, 1300, 1154, 1099, 1071, 906, 839. | CDCl$_3$ 7.73-7.45 (AA'BB', 4H, arom), 7.21 (NH$_2$), 3.80 (t, 2H, CH$_2$), 2.95 (t, 2H, CH$_2$), 2.60 (quint, 2H, CH$_2$), 2.5-2.4 (m, 4H, 2 CH$_2$), 1.8-1.6 (m, 4H, 2 CH$_2$). | |
| 33 | (structure) | 161 | cm-1: 3320, 3238, 2952, 1594, 1331, 1158, 1090, 834, 549 | ppm: 7.86-7.82 (AA', 2H, arom), 7.44-7.40 (BB', 2H, arom), 4.93 (2H, NH$_2$), 3.88 (t, 2H, CH$_2$), 2.61 (t, 2H, CH$_2$), 2.41 (quint, 2H, CH$_2$), 2.42 (s, 3H, CH$_3$), 1.20 (s,9H,CH$_3$), | |
| 14 | (structure) | 256.2 | 3343, 3232, 2926, 2849, 1595, 1334, 1161, 1094, 735, 548 | (CDCl$_3$): 7.91-7.86 /, 7.39-7.35 (AA'BB', 4H, arom), 4.78 (s, NH$_2$), 3.875 (t, CH$_2$, J=7.0Hz), 2.89 (t, CH$_2$, J=7.3Hz), 2.56-2.46 (m, CH$_2$) 2.30 (s,CH$_3$) 1.81-1.59 /, 1.27-1.21 (m, 10H, cyclohex.) | (CDCl$_3$): 143.0, 137.4, 132.5, 129.2, 126.4, 119.8, 113.4, 44.6, 36.1, 33.3, 27.3, 26.7, 26.2, 24.6, 11.9 |

Fig. 9

| # | Structure | mp | IR | ¹H NMR | ¹³C NMR |
|---|---|---|---|---|---|
| 35 | (sulfonamide-phenyl-pyrrole fused cyclopentane with isobutyl sidechain) | 197.10 | 3337, 3235, 2948, 1595, 1332, 1161, 1093, 546 | (d6-DMSO): 7.74-7.42 (m, 4H, arom), 7.24 (NH₂), 3.82 (t, 2H, CH₂), 2.87 (t, 2H, CH₂), 2.41-2.37 (d+m, 4H, 2xCH₂), 2.09 (s, 3H, CH₃), 0.735 (d, 6H.CH(CH₃)₂) | (d6-DMSO): 141.7, 139.3, 133.1, 126.8, 125.8, 120.7, 119.1, 112.4, 44.2, 40.2, 34.3, 29.6, 26.5, 24.7, 22.4, 10.1 |
| 38 | (sulfonamide-phenyl-pyrrole fused cyclopentane with propyl sidechain) | 165.70 | 3326, 3233, 2926, 2855, 1596, 1427, 1331, 1301, 1159, 1094, 546 | (d6-DMSO): 7.76-7.72 / 7.45-7.41 (AA'BB' system, 4H), 7.24 (NH₂), 3.835 (t, 2H, CH₂), 2.87 (t, 2H, CH₂), 2.44-2.41 (2xCH₂, 4H), 2.11 (s, 3H, CH₃), 1.29-1.23 (m, 4H, 2xCH₂), 0.825 (t, 3H, CH₃) | (d6-DMSO):141.4, 139.3, 132.8, 126.7, 125.8, 120.1, 120.0, 112.1, 44.1, 33.1, 26.5, 24.7, 24.6, 22.0, 13.7, 9.7 |
| 37 | (sulfonamide-phenyl-pyrrole fused cyclopentane with isopentyl sidechain) |  |  | (CDCl₃): 7.76-7.72 / 7.44-7.40 (AA'BB' system, 4H), 7.24 (NH₂), 3.83 (t, 2H, CH₂, J=6.9), 2.88 (t, 2H, CH₂, J=7.1), 2.48-2.37 (m, 4H, 2xCH₂), 2.11 (s, 3H, CH₃), 1.6-1.4 (m, 1H, CH), 1.23 –1.17 (m, 2H, CH₂), 0.845 (d, 6H, CH(CH₃)₂) | (CDCl₃): 141.3, 139.3, 132.8, 126.7, 125.8, 120.1, 119.9, 112.1, 44.1, 30.7, 27.5, 26.5, 24.7, 22.7, 22.3, 9.6 |
| 36 | (sulfonamide-phenyl-pyrrole fused cyclopentane with cyclohexylmethyl sidechain) | 215°C dec | 3329, 3236, 2923, 2849, 1594, 1332, 1299, 1162. | (CDCl₃): 7.88-7.84 / 7.49-7.45 (AA'BB' system, 4H), 4.8-4.6 (2H, NH₂), 3.88 (t, 2H, CH₂, J=7.0), 2.955 (t, 2H, CH₂, J=7.2), 2.54-2.42 (q+d, 4H, 2xCH₂), 2.17 (s, 3H, CH₃), 1.8-0.7 (cyclohexyl, 11H) |  |

Fig. 10

| Ex. | Structure | IC50 (COX-1) | IC50 (COX-2) | IC50 (5-LO) | Selectivity Cox1 / Cox2 | Rat paw oedema: Inhibition [%], 3 mg p.o. |
|---|---|---|---|---|---|---|
| 8 | 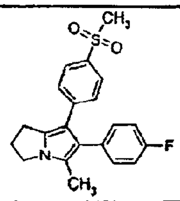 | 6.4 | 0.22 | 0.38 | 29 | |
| 28 | 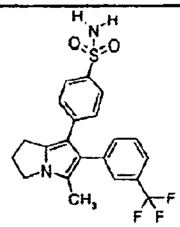 | 8.5 | 0.24 | 2.6 | 35 | 10 |
| 27 | 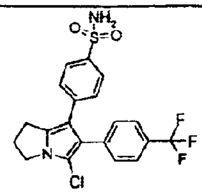 | 2.9 | <0.015 | 2.35 | 193 | 20 |
| 14 | 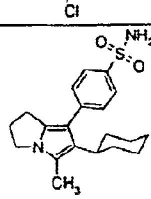 | 8.5 | 0.018 | 1.2 | 472 | 20 |
| 35 | 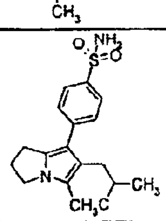 | -- | 0.03 | 3.0 | | 22 |
| 41 | 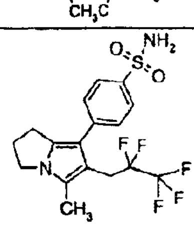 | -- | 0.29 | 7.6 | >300 | n.d. |

Fig. 11
| Reference. A | 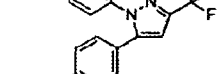 Celecoxib | 3.1 | 0.13 |  | 24 |  |
| --- | --- | --- | --- | --- | --- | --- |
| Ref. B | 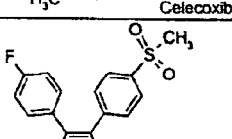 | – | – | 0.2 |  |  |
| Ref. C | 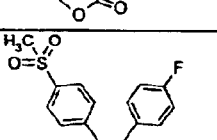 |  | 0.26 | 1.2 |  |  |
| Ref. D | 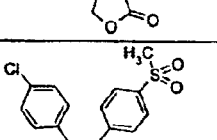 SC 57666 |  | 0.37 |  |  |  |

FUSED PYRROLE COMPOUNDS, PHARMACEUTICAL AGENTS CONTAINING THE SAME, AND THE USE THEREOF

The present invention relates to fused pyrrole compounds, in particular pyrrolizines, indolizines and heteroanalogues having selective inhibitory action on isoenzyme-2 of prostaglandin H synthase (COX-2); pharmaceutical compositions which contain these compounds; and the use of these compounds for the treatment of disorders of the rheumatic type.

It is recognized that the arachidonic acid metabolites prostaglandin $E_2$ (PGE$_2$), prostaglandin $I_2$ (PGI$_2$) and thromboxane $B_2$ (TXB$_2$) intervene profoundly in the inflammatory process. The key enzyme for prostaglandin synthesis is prostaglandin H synthase. As a cyclooxygenase, it produces prostaglandin $H_2$ (PGH$_2$) from arachidonic acid via the intermediate prostaglandin $G_2$ (PGG$_2$). The enzyme exists in two isoforms, namely cyclooxygenase-1 and cyclooxygenase-2. Since the structures of the two isoezymes have already been elucidated, structural differences between the two enzymes have also been investigated more thoroughly.

Cyclooxygenase-1 exists in almost all cells and produces intra- and extracellular ubiquitous prostaglandin mediators which are necessary in physiological amounts for the function of organs, such as the stomach and kidneys.

The inhibition of this enzyme suppresses the synthesis of the vasodilating PGE$_2$ as well as that of the cytoprotective PGI$_2$. The decreased circulation and lack of protective effect can lead to damage to the gastric mucous membrane and as a result to ulceration. As a result of ischaemia, decreased renal blood flow can lead to damage to the renal parenchyma and further to renal insufficiency.

Cyclooxygenase-2, however, is only found in specialized cells, e.g. in blood cells, such as monocytes and granulocytes, in synovial cells, vascular endothelial cells (venous) and locally in inflamed tissue. Experimentally, the formation (expression) of the isoenzyme-2 is induced by phorbol esters, lipopolysaccharides and other stress factors which can provoke local inflammation.

Non-steroidal anti-inflammatory drugs (NSAIDs), such as acetylsalicylic acid, mefanamic acid, diclofenac, indomethacin, ibuprofen and naproxen, are widely used clinically. Pharmacologically, they act via inhibition of cyclooxygenase.

Pyrrolizine compounds which have a similar pharmacological action are known from numerous publications. For example, pyrrolizine compounds having anti-inflammatory activity are described in Arch. Pharm. 319, 65–69 (1986); 319, 231–234 (1986); 318, 661–663 (1985); 318, 663–664 (1985); 319, 500–505 (1986); 319, 749–755 (1986); 327, 509–514 (1994); 330, 307–312 (1997) and in J. Med. Chem. 1987, 30, 820–823 and 1994, 37, 1894–1897.

Further pyrrolizine compounds are described in U.S. Pat. No. 5,260,451 (corresponding to EP 0397175) and in WO 95/32970; WO 95/32971; and WO 95/32972. These compounds have the structural formula

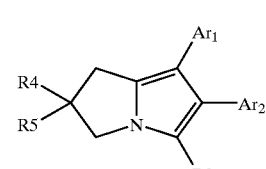

Formula II

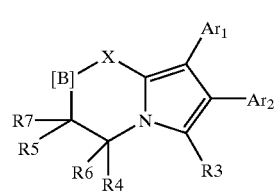

Formula III

A fused diarylpyrrole structural element and a third acidic radical $R^3$ is common to all compounds. The compounds are distinguished by high lipophilicity, good bioavailability and average half-lives, see Drugs of the Future, 1995, 20 (10):1007–1009.

Further pyrrolizine compounds of similar constitution are described in DE 198 45 446.6 and PCT/EP 99/09057. According to U.S. Pat. No. 4,232,038, alkylsulphinylbenzoyl- and alkylsulphonylbenzoyl-substituted pyrrolizines should also have anti-inflammatory, analgesic and antipyretic properties. According to DE 196 24 290.8 and DE 196 24 289.4, certain compounds of this type have lipid-lowering action.

ML 3000 (1), for example, a vicinally diaryl-substituted pyrrole derivative, is described as a dual inhibitor of cyclooxygenase (COX) and 5-lipoxygenase (LOX).

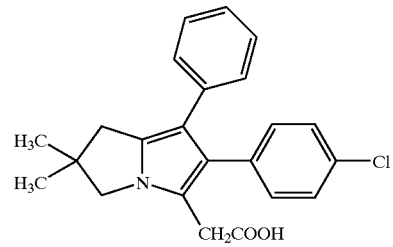

1, ML 3000

However, via the inhibition of cyclooxygenase, toxic side effects also result, which are especially associated with the inhibition of the constitutive, physiological cyclooxygenase-1. More recent investigations show that the classical NSAIDs have an inadequate selectivity and frequently even prefer the isoenzyme-1 of cyclooxygenase.

A selective inhibition of the cyclooxygenase-2 specifically overexpressed in inflamed tissue and leading to tissue damage due to the formation of non-physiological tissue levels of prostaglandins should lead to a superior, namely lower side-effect, anti-inflammatory principle.

Substances which selectively inhibit cyclooxygenase-2 have likewise already been described.

These especially include all 5-membered heterocyclic rings having bisaryl substitution. For example, WO 94/15932 mentions 3,4-diarylthiophenes, -furans and -pyrroles, and occasionally 3-(4-methylsulphonylphenyl)-4-(4-fluorophenyl)thiophene. WO 94/27980 describes 4,5- diaryloxazoles, for example 4-(4-fluorophenyl)-2-methyl-5-[4-(methylsulphonyl)phenyl]oxazole. In EP 0087629, 2,3-diaryl-5-halothiophenes, for example 5-bromo-2,3-bis(4-fluorophenyl)thiophene, are mentioned and WO 95/15315 reports 1,5-diphenylpyrazoles, for example 5-(4-fluorophenyl)-1-[4-(methylsulphonyl)phenyl]-3-(trifluoromethyl)pyrazole. 2,3-Diarylpyrroles are mentioned in WO 95/00501 just as the 3,4-diarylfuranones illustrated below by example of lactones 4 and 5.

In addition, cycloaliphatic or aromatic non-heterocyclic rings with bisaryl substitution are also found. For example, bisarylphenyls, for example 2-[(4-methylthio)phenyl]-1-biphenyl, are also described in WO 96/10012. 5-membered rings, in turn, can be looked up in WO 95/11883 as 1,2-diarylcyclopentenes illustrated below by example of the cyclopentene 6, (SC57666, SC 57949), and to which a spiro unit can be linked in the 4-position following WO 95/21817, for example as is the case in 5-(4-fluorophenyl)-6-[4-(methylsulphonyl)phenyl]spiro[2.4]hept-5-ene. Finally, the 2,3-diarylcyclopentadienes described in WO 95/30656, for example 1-methylsulphonyl-4-[1,1-dimethyl-4-(4-fluorophenyl)cyclopenta-2,4-dien-3-yl]benzene, may also be mentioned.

Further pyrroles are described by Wilkerson et al. in J. Med. Chem 1994, 37, 988–998 and J. Med. Chem. 1995, 38, 3895–3901. WO 99/61016 also indicates certain substituted pyrroles as cyclooxygenase-2 inhibitors.

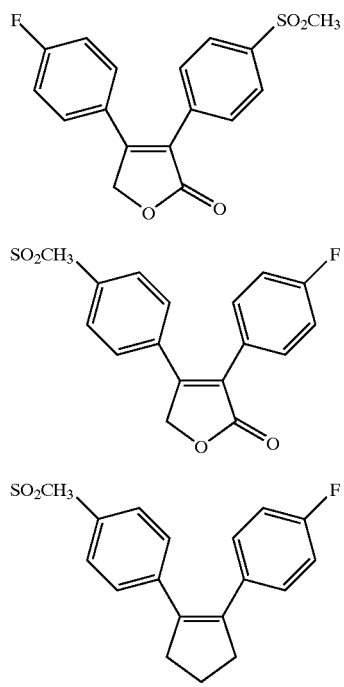

In the case of the lactones 4 and 5, only compound 5 shows a high activity on cyclooxygenase-2 and high selectivity for this isoform.

The object of the present invention was to make available novel compounds which inhibit cyclooxygenase-2 more strongly than cyclooxygenase-1.

This object has surprisingly been achieved by means of [α]-fused pyrrole compounds which carry a phenyl group substituted in the para-position by certain sulphur-containing groups.

The present invention therefore relates to [α]-fused pyrrole compounds of the formula 1

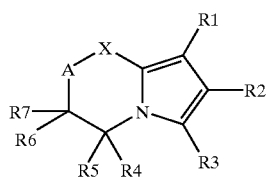

Formula 1 in which
X is CR8R9, S, O, NR12 or C(O);
A is CR10R11 or a bond between X and the atom carrying the radicals R6 and R7;
the first of the radicals R1, R2, R3 is
  4-substituted phenyl, the substituent being selected from alkylthio, alkylsulphinyl, alkylsulphonyl, sulphamoyl, N-alkylsulphamoyl, N,N-dialkylsulphamoyl, alkylsulphonamido or alkylsulphone-N-alkylamido;
the second of the radicals R1, R2, R3 is
  alkyl which is optionally substituted by identical or different substituents selected from halogen, cycloalkyl, alkoxy, trifluoromethoxy, hydroxyl or trifluoromethyl, cycloalkyl which is optionally substituted by identical or different substituents selected from halogen, alkyl, haloalkyl, cycloalkyl, alkoxy, haloalkoxy or hydroxyl, phenyl which is optionally substituted by identical or different substituents selected from halogen, alkyl, haloalkyl, alkoxy, haloalkoxy, alkylthio, hydroxyl, nitro, alkylsulphinyl, alkylsulphonyl, sulphamoyl, N-alkylsulphamoyl, N,N-dialkylsulphamoyl, alkylsulphonamido or alkylsulphone-N-alkylamido; or
  an aromatic or non-aromatic mono- or bicyclic, optionally benzo-fused, heterocyclic radical which contains 1, 2 or 3 heteroatoms independently of one another selected from N, O and S and is optionally substituted by identical or different substituents selected from halogen, alkyl, haloalkyl, alkoxy, haloalkoxy, alkylthio, hydroxyl, nitro, alkylsulphinyl, alkylsulphonyl, sulphamoyl, N-alkylsulphamoyl, N,N-dialkylsulphamoyl, alkylsulphonamido or alkylsulphone-N-alkylamido;
the third of the radicals R1, R2, R3 is
  H, alkyl, haloalkyl, hydroxyalkyl, —CHO, —COOH, —COCOOH, —COO-alkyl, —COO-Alkphenyl, —COCOO-alkyl, halogen, cyano, alkylsulphonyl, sulphamoyl or B—Y;
  in which
  B is alkylene or alkyenylene, each of which can optionally be substituted by hydroxyl or alkoxy;
  Y is —COOH, —COO-alkyl, —SO₃-alkyl, —CHO or hydroxyl; or
the second and the third of the radicals R1, R2, R3, together with the C atoms to which they are bonded, are saturated or unsaturated cycloalkyl;
R4–R11, which can be identical or different, are hydrogen, alkyl, hydroxyalkyl, alkoxyalkyl, hydroxyl, COOH or acyloxy, where vicinal radicals can also represent bonds or geminal radicals, also together with the C atom to which they are bonded, can represent carbonyl or cycloalkyl;

R12 is hydrogen, alkyl or phenyl,
and optical isomers, physiologically tolerable salts and physiologically hydrolysable esters thereof.

Preferred embodiments to which this invention relates are described in the adjacent claims.

The physiologically tolerable salts in the present case can be acid addition or base addition salts.

For acid addition salts, inorganic acids, such as hydrochloric acid, sulphuric acid, nitric acid or phosphoric acid, or organic acids, in particular carboxylic acids, e.g. acetic acid, tartaric acid, lactic acid, citric acid, malic acid, mandelic acid, ascorbic acid, maleic acid, fumaric acid, gluconic acid or sulphonic acids, e.g. methanesulphonic acid, benzenesulphonic acid and toluenesulphonic acid, and the like are used.

The base addition salts include salts of the compounds of the formula I with inorganic bases, such as sodium hydroxide or potassium hydroxide, or with organic bases, such as mono-, di- or triethanolamine.

Physiologically easily hydrolysable esters of the compounds of the formula I are, for example, alkyl, pivaloyloxymethyl, acetoxymethyl, phthalidyl, indanyl and methoxymethyl esters.

If the compounds according to the invention have asymmetric centres, racemates and optical isomers are included as mixtures or in pure form (enantiomers, diastereomers).

The term "alkyl, alkoxy etc." includes straight-chain or branched alkyl groups, such as $CH_3$, $C_2H_5$, n-propyl, $CH(CH_3)_2$, n-butyl, $CH(CH_3)$—$C_2H_5$, isobutyl, $C(CH_3)_3$, n-pentyl or n-hexyl, in particular $CH_3$, $C_2H_5$ or $CH(CH_3)_2$, preferably having—if not stated otherwise—1 to 8, in particular 1 to 6 and particularly preferably 1 to 4, carbon atoms; as a substituent of one of the radicals R1 to R12, "alkyl, alkoxy etc." preferably comprises 1 to 4 carbon atoms.

Substituted "alkyl, alkoxy etc." in particular includes:

haloalkyl, i.e. alkyl which is partially or completely substituted by fluorine, chlorine, bromine and/or iodine, i.e., for example, $CH_2F$, $CHF_2$, $CF_3$, $CH_2Cl$, 2-fluoroethyl, 2-chloroethyl or 2,2,2-trifluoroethyl; as a substituent of one of the radicals R1 to R12, haloalkyl is preferably $CHF_2$ and especially $CF_3$;

haloalkoxy, i.e. alkoxy which is partially or completely substituted by fluorine, chlorine, bromine and/or iodine, i.e., for example, the haloalkoxy radicals corresponding to the haloalkyl radicals listed above; as a substituent of one of the radicals R1 to R12, haloalkoxy is preferably $OCHF_2$ and especially $OCF_3$;

alkoxyalkyl, i.e. alkyl substituted by alkoxy, i.e., for example, —$CH_2$—$OCH_3$ or 2-methoxyethyl;

hydroxyalkyl, i.e. alkyl which is preferably monosubstituted by hydroxyl, e.g. hydroxymethyl or 2-hydroxyethyl;

trifluoromethylalkyl, i.e. alkyl which is preferably monosubstituted by trifluoromethyl, e.g. the radicals described under hydroxyalkyl, which are substituted by trifluoromethyl instead of by hydroxyl;

trifluoromethoxyalkyl, i.e. alkyl which is preferably monosubstituted by trifluoromethoxy, e.g. the radicals described under hydroxyalkyl which are substituted by trifluoromethoxy instead of by hydroxyl;

cycloalkylalkyl, i.e. alkyl which is preferably monosubstituted by cycloalkyl, e.g. the radicals described under hydroxyalkyl, which are substituted by cyclopropyl, cyclobutyl, cyclopentyl or cyclohexyl instead of by hydroxyl.

The term "cycloalkyl" includes mono- or bicyclic alkyl groups, such as cyclopropyl, cyclobutyl, cyclopentyl, cyclohexyl, etc., preferably having—if not stated otherwise—3 to 9, in particular 3 to 7 and particularly preferably 5 or 6, carbon atoms.

The term "alkylene" includes straight-chain or branched alkylene groups, such as methylene and ethylene, preferably having—if not stated otherwise—1 to 8, in particular 1 to 6 and particularly preferably 1 to 4, carbon atoms. If alkylene is substituted by hydroxyl or alkoxy, monosubstitution is preferred.

The term "alkenylene" includes straight-chain or branched, mono- or polyunsaturated alkylene groups, such as ethenylene, preferably having—if not stated otherwise—2 to 8, in particular 2 to 6 and particularly preferably 2 to 4, carbon atoms. If alkenylene is substituted by hydroxyl or alkoxy, monosubstitution is preferred.

Acyloxy means —OCOR, in which R can be alkyl or aryl. Acetyloxy and benzoyloxy may be mentioned in particular.

—COOAlkyl means alkoxycarbonyl, such as CO—$OCH_3$, CO—$OC_2H_5$, CO—$OCH_2$—$C_2H_5$, CO—$OCH(CH_3)_2$, n-butoxycarbonyl, CO—$OCH(CH_3)$—$C_2H_5$, CO—$OCH_2$—$CH(CH_3)_2$, CO—$OC(CH_3)_3$, in particular CO—$OCH_3$, CO—$OC_2H_5$, CO—$OCH(CH_3)_2$ or CO—$OCH_2$—$CH(CH_3)_2$.

—COOAlkPhenyl means an alkoxycarbonyl group substituted by phenyl on the alkyl radical, such as benzyloxycarbonyl.

—COCOOAlkyl means an alkyl ester of a carboxycarbonyl group.

Alkylthio means —S-alkyl and is also designated as alkylsulphanyl or alkylmercapto, such as $SCH_3$, $SC_2H_5$, $SCH_2$—$C_2H_5$, $SCH(CH_3)_2$, n-butylthio, 1-methylpropylthio, 2-methylpropylthio, $SC(CH_3)_3$. Methylthio is preferred.

Alkylsulphinyl means —S(O)-alkyl and is also designated as alkylsulphoxo, such as SO—$CH_3$, SO—$C_2H_5$, n-propylsulphinyl, 1-methylethylsulphinyl, n-butylsulphinyl, 1-methylpropylsulphinyl, 2-methylpropylsulphinyl, 1,1-dimethylethylsulphinyl. Methylsulphinyl is preferred.

Alkylsulphonyl means —S(O)$_2$-alkyl and is also designated as alkylsulphone, such as $SO_2$—$CH_3$, $SO_2$—$C_2H_5$, n-propylsulphonyl, $SO_2$—$CH(CH_3)_2$, n-butylsulphonyl, 1-methylpropylsulphonyl, 2-methylpropylsulphonyl, $SO_2$—$C(CH_3)_3$. Methylsulphonyl is preferred.

Sulphamoyl means —S(O)$_2$NH$_2$ and is also designated as amidosulphonyl or sulphonamide.

N-Alkylsulphamoyl means monosubstituted sulphamoyl —S(O)$_2$NH-alkyl, e.g. —S(O)$_2$NH—$CH_3$.

N,N-Dialkylsulphamoyl means disubstituted sulphamoyl —S(O)$_2$N-(alkyl)$_2$, where the two nitrogen-bonded alkyl radicals can be identical or different, e.g. —S(O)$_2$N(CH$_3$)$_2$.

Alkylsulphonamido means —NHS(O)$_2$-alkyl, such as NHSO$_2$—CH$_3$, NHSO$_2$—C$_2$H$_5$, n-propylsulphon-amido, NHSO$_2$—CH(CH$_3$)$_2$, n-butylsulphonamido, 1-methylpropylsulphonamido, 2-methylpropylsulphonamido, NHSO$_2$—C(CH$_3$)$_3$. Methylsulphonamido is preferred.

Alkylsulphone-N-alkylamido means —N(alkyl)S(O)$_2$-alkyl, where the nitrogen-bonded and the sulphur-bonded alkyl radicals can be identical or different, e.g. N(CH$_3$)SO$_2$—CH$_3$.

Carbonyl, CHO, —COOH, —COCOOH, —SO₃H means >C═O, formyl, carboxy, carboxycarbonyl or sulpho.

"Aryl" is preferably naphthyl and in particular phenyl.

The term "halogen" includes a fluorine, chlorine, bromine or iodine atom and in particular a fluorine, chlorine or bromine atom. As a rule, fluorine and chlorine atoms are preferred, if appropriate also bromine atoms.

The "heterocyclic radical" is in particular a 5- or 6-membered heterocyclic radical which can be aromatic or non-aromatic, mono- or bicyclic, and/or benzo-fused. The aromatic radicals include nitrogen-containing heterocyclic radicals, such as pyrrolyl, imidazolyl, pyrazolyl, pyridazinyl, pyrazinyl, indolyl, quinolinyl, especially pyridyl, pyrimidyl and isoquinolinyl. The aromatic radicals also include those heterocyclic radicals which contain an oxygen atom or a sulphur atom, such as thienyl, benzothienyl, furanyl and especially benzofuranyl. Also included here are heterocyclic radicals which contain two or more different heteroatoms, such as thiazolyl, isothiazolyl, thiadiazolyl, isoxazolyl and oxazolyl. Preferred aromatic heterocyclic radicals are thienyl, pyridyl and thiazolyl. The non-aromatic radicals include nitrogen-containing heterocyclic radicals, such as piperidinyl and piperazinyl. These also include heterocyclic radicals which contain two or more different heteroatoms, such as morpholinyl.

Substituted radicals, in particular alkyl, cycloalkyl, aryl and heteroaryl, are preferably mono-, di- or trisubstituted.

For substitution with halogen, it moreover applies that poly- and in particular perhalogenated, especially poly- and in particular perfluorinated, radicals should also be covered. Preferred radicals of this type are poly- and in particular perhalogenated aliphatic radicals in which 2 or more or in particular all C-bonded hydrogen atoms are replaced by a halogen atom and in particular a fluorine atom. Especially, mention may be made here of poly- and in particular perhalogenated alkyl, such as trifluoromethyl, 2,2,2-trifluoroethyl, perfluoroethyl, 3,3,3-trifluoropropyl, 2,2,3,3,3-pentafluoropropyl, perfluoropropyl, 1,1,1-trifluoroisopropyl, 1,1,1,3,3,3-hexafluoroisopropyl, perfluoroisopropyl, 4,4,4-trifluorobutyl, 3,3,4,4,4-pentafluorobutyl, 2,2,3,3,4,4,4-heptafluorobutyl, perfluorobutyl, perfluoroisobutyl, perfluoro-sec-butyl and perfluoro-t-butyl and the corresponding poly- and in particular perchlorinated radicals.

The [α]-fused ring can be 6- or especially 5-membered, heterocyclic or especially alicyclic, and if alicyclic, then unsaturated or especially saturated, and/or consequently substituted or unsubstituted.

The [α]-fused pyrrole compounds of the formula 1 according to the invention in particular include those in which X is CR8R9 and A is a bond between X and the atom carrying the radicals R6 and R7 (pyrrolizines); X is CR8R9 and A is CR10R11 (indolizines); X is NR12 and A is a bond between X and the atom carrying the radicals R6 and R7 (pyrrolo[1,2-a]imidazoles); X is S and A is a bond between X and the atom carrying the radicals R6 and R7 (pyrrolo[2,1-b]thiazoles); X is S and A is CR10R11 (pyrrolo[2,1-b]1,3-thiazines); X is O and A is CR10R11 (pyrrolo[2,1-b]1,3-oxazines); X is O and A is a bond between X and the atom carrying the radicals R6 and R7 (pyrrolo[2,1-b]oxazoles), where the radicals not mentioned can have the meanings indicated above.

If the [α]-fused ring is a 5-membered unsaturated radical, R4 and R6 are especially a bond, such as in pyrrolizine, pyrrolo[2,1-b]imidazole and pyrrolo[2,1-b]thiazole. If the [α]-fused ring is a 6-membered unsaturated radical, R4 and R6, such as in pyrrolo[2,1-b]1,3-thiazine, pyrrolo[2,1-b]1,3-oxazine or 5,6-dihydroindolizine, and optionally also R8 and R10 are a bond, such as in indolizine.

Without being bonded to a specific [α]-fused ring, according to a particular embodiment of the present invention R4–R11, which can be identical or different, are hydrogen or alkyl. According to another particular embodiment, at least one of the radicals R4, R5, R6 and R7 is hydroxyalkyl, in particular hydroxymethyl, and the other radicals R4, R5, R6 and R7 independently of one another are H or alkyl, R4 preferably being hydroxyalkyl, in particular hydroxymethyl, R5 being H or alkyl and R6 and R7 independently of one another being H or alkyl. According to a further particular embodiment, one of the radicals R8 and R9 is H, alkyl, hydroxyalkyl or alkoxyalkyl and the other is hydroxyl, alkoxy, carboxyl or acyloxy, or R8 and R9, together with the carbon atom to which they are bonded, are a carbonyl group.

6,7-Dihydro-5H-pyrrolizines are preferred, i.e. compounds of the formula 1 in which X is CR8R9, A is a bond between X and the atom carrying the radicals R6 and R7 and R4, R5, R6, R7, R8, R9, which can be identical or different, have the abovementioned meanings and are preferably hydrogen or alkyl. In particular, mention may be made of 6,7-dihydro-5H-pyrrolizines in which R4 to R9 are all hydrogen or at least one of the radicals R4 to R9, for example R6 and/or R8 is alkyl, in particular methyl.

According to the invention, one of the radicals R1, R2, R3 is 4-substituted phenyl (para-substituted phenyl), the substituent being selected from certain sulphur-containing groups, namely from alkylthio, alkylsulphinyl, alkylsulphonyl, sulphamoyl, N-alkylsulphamoyl, N,N-dialkylsulphamoyl, alkylsulphonamido and alkylsulphone-N-alkylamido. Preferred substituents are alkylthio, alkylsulphinyl, alkylsulphonyl, sulphamoyl and alkylsulphonamido, in particular methylthio, methylsulphinyl, methylsulphonyl, sulphamoyl and methylsulphonamido, very particularly methylsulphonyl and sulphamoyl.

A—more advantageously lipophilic—second of the radicals R1, R2, R3 can be linear or branched, alicyclic or heterocyclic, non-aromatic or aromatic. On the one hand, aryl radicals, in particular phenyl radicals, on the other hand aliphatic and cycloaliphatic, in particular alkyl, cycloalkyl and cycloalkylalkyl radicals, are preferred. These radicals can be substituted according to the above details. Substitution is advantageous in particular for the first case, i.e. of aryl substitution. Accordingly, the second of the radicals R1, R2, R3 is in particular phenyl monosubstituted in the para or meta position, in particular 4-substituted phenyl. Optionally present substituents are preferably selected from alkyl groups, in particular methyl, and especially electronegative groups, such as halogen atoms, in particular fluorine, and haloalkyl groups, in particular trifluoromethyl.

If the second of the radicals R1, R2, R3 is an alkyl radical, on the one hand alkyl radicals having a relatively large number of carbon atoms, in particular the abovementioned $C_{4-6}$-alkyl radicals, and of these advantageously the branched and in particular the singly branched, and on the other hand alkyl radicals having a relatively low number of carbon atoms, especially methyl, are preferred.

If the second of the radicals R1, R2, R3 is a cycloalkyl radical, cyclohexyl is particularly advantageous.

If the second of the radicals R1, R2, R3 is a cycloalkylalkyl radical, cycloalkylmethyl radicals are preferred, cyclopropylmethyl being advantageous.

According to a preferred embodiment, the second of the radicals R1, R2, R3 is a fluoroaliphatic, in particular a poly- or in particular perfluorinated aliphatic radical. In particular, mention may be made here of poly- and perfluorinated alkyl radicals, i.e. especially the previously described alkyl radicals, in which 2 or more and in particular all H atoms are replaced by fluorine atoms. This analogously applies to cycloalkyl and cycloalkylalkyl radicals.

According to a particular embodiment of the present invention, a third of the radicals R1, R2, R3 is hydrogen, alkyl, haloalkyl, hydroxyalkyl, halogen, cyano, alkylsulphonyl, sulphamoyl or B—Y, in which B is alkylene or alkenylene, each of which can optionally be substituted by hydroxyl or alkoxy, and Y is hydroxyl; in the context of this embodiment hydrogen, alkyl, haloalkyl, in particular $CF_3$ or halogen, are preferred. If the third of the radicals is B—Y, B is preferably alkylene which is optionally substituted by hydroxyl.

If the third radical is an alkyl radical, the relatively short radicals are preferred here, where mention may in particular be made of methyl. Preferred alkoxycarbonyl radicals are methoxy- and ethoxycarbonyl. Of the halogen atoms, chlorine and optionally bromine are preferred in this case.

A second and a third of the radicals R1, R2, R3, if they are vicinal to one another, together with the C atoms to which they are bonded, can also form a cycloaliphatic radical. If R2 and R3 are involved, this ring taken per se is an unsaturated ring, for example a cyclopentenyl or cyclohexenyl ring, as is illustrated in the present Example 32. If R1 and R2 are involved, the ring has two exocyclic double bonds.

Preferably, the first and the second of the radicals R1, R2, R3 are vicinal to one another, i.e. R1 and R2 or R2 and R3 are involved. This leads to advantages, in particular for the [α]-fused pyrrole compounds according to the invention having bisaryl substitution.

In principle, the positions of the groups designated as first, second and third radicals are variable. It has proved advantageous if the first of the radicals R1, R2, R3 is in the position of R1 or R3. It has also proved advantageous if the second of the radicals R1, R2, R3 is in the position of R2.

Compounds in which R3 is CHO, —COOH, —COCOOH, —COOalkyl, —COOAlkphenyl, —COCOOalkyl or B—Y, in which B is alkylene or alkenylene, each of which can optionally be substituted by hydroxyl or alkoxy, and Y is —COOH, —COO-alkyl or —CHO, can be used as synthesis intermediates. In the context of this particular embodiment, preferred radicals B—Y are 2-acetic acid and 3-propionic acid radicals.

The compounds according to the invention can be prepared in the following way (in the schemes the radicals indicated have the previously mentioned meanings, if not stated otherwise; details in brackets serve as illustrative examples). In the reaction schemes, acyl has the meanings indicated above. R is an alkyl radical if not stated otherwise.

The synthesis of sulphoxides and sulphones can be carried out via the reduction of sulphonyl chlorides using base metals, such as iron and zinc, in acidic, aqueous systems to give suitable thiols, which are then first alkylated to give thioethers and then oxidized stepwise using peroxides.

A further possibility for the synthesis of sulphones proceeds via reduction of sulphonyl chlorides with base metals, such as iron and zinc, in neutral, buffered, aqueous systems, or using sulphites, to give sulphinates, which are then alkylated to alkylsulphinates and finally thermally rearranged to give the sulphones.

For example, 6-(4-fluorophenyl)-5-methyl-7-phenyl-2,3-dihydro-1H-pyrrolizine, which can be prepared from 2-benzylpyrroline and 2-bromo-1-(4-fluorophenyl)ethanone according to the process described by Laufer et al. (J. Med. Chem. 1994, 37, 1894–1897), can be sulphonated in chlorosulphonic acid and converted to the sulphonyl chloride by means of a suitable chlorinating agent, such as phosphorus pentachloride, but also by means of excess chlorosulphonic acid, preferably in the presence of heat. The sulphonyl chloride is then reduced in an aqueous solution of sodium sulphite and a suitable base, e.g. sodium hydrogencarbonate at elevated temperature, e.g. 70° C. The anion of the sulphinic acid formed, which is in solution, is alkylated in, for example, an ethanolic/aqueous system using an alkyl iodide and the alkyl sulphinite primarily formed is converted into the desired alkylsulphone by heating (e.g. 100° C.) for a number of hours (Reaction 1).

Reaction 1:

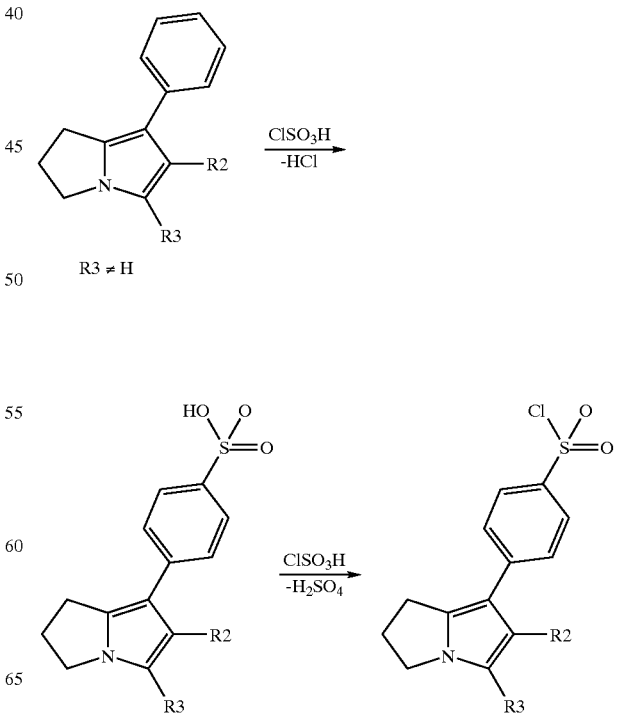

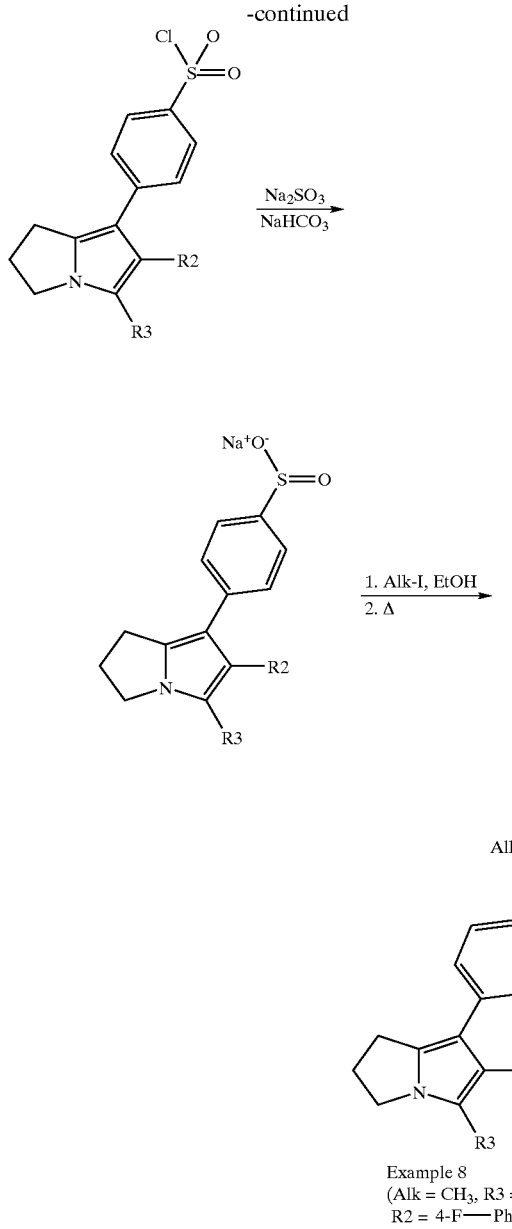

Example 8
(Alk = CH₃, R3 = CH₃,
R2 = 4-F—Ph—)

If necessary, a protective group is first introduced for the extremely reactive position 5 of the starting compound, e.g. 6-(4-fluorophenyl)-7-phenyl-2,3-dihydro-1H-pyrrolizine. Suitable protective groups for reactive positions on pyrroles are carboxylic acid ester groups, which can be prepared almost quantitatively via the reaction of these pyrroles, for example, with phosgene, diphosgene or triphosgene and the subsequent alcoholysis of the carbonyl chlorides formed as intermediates. After introduction of the desired group has taken place, the esters are hydrolysed and the pyrrolecarboxylic acids isolated are thermally decarboxylated to the pyrroles.

Advantageously, the aromatics carrying the necessary sulphur functions can be introduced by means of suitable precursors even during the synthesis of the pyrrolizine structure, as a result of which shortening of the synthesis sequence results. For example, the 4-methylsulphanylbenzyl-2-pyrroline (7) necessary for the synthesis of the compound from Example 6 according to the technique outlined is accessible via the Grignard reaction of 4-methylsulphanylbenzyl bromide with magnesium and subsequent addition to 4-chlorobutyronitrile (Reaction 2).

Reaction 2:

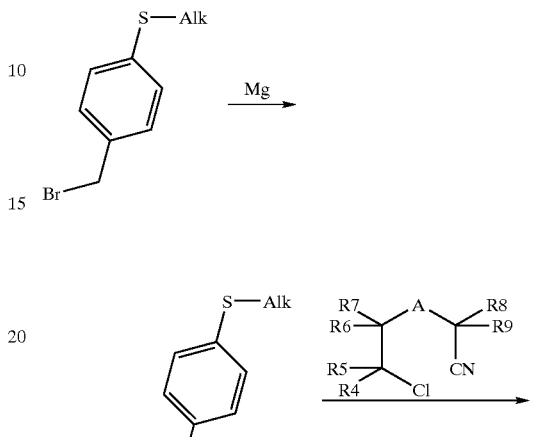

Grignard

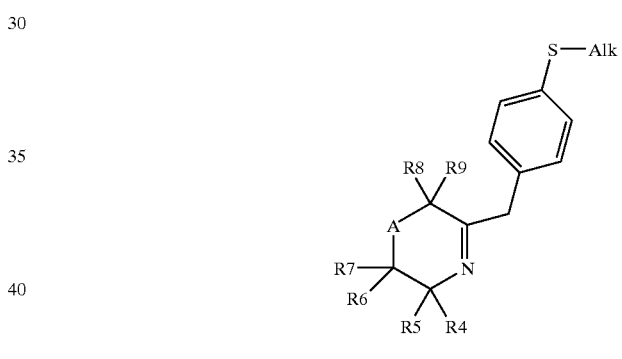

Preferably, the preparation of the intermediate 7 is carried out via the condensation of a 4-alkyl-sulphonylphenylacetic acid ester with N-vinyl-2-pyrrolidone in the presence of strong bases, e.g. NaH, K tert-butoxide, etc. and subsequent hydrolytic cleavage and decarboxylation of the 1-vinyl-3-acyl-2-pyrrolidone formed in high yield as an intermediate (Reaction 3). For example, the reaction of the intermediate 7 with 2-bromo-1-(4-fluorophenyl)ethanone yields the pyrrolizine shown below (Example 6).

Reaction 3:

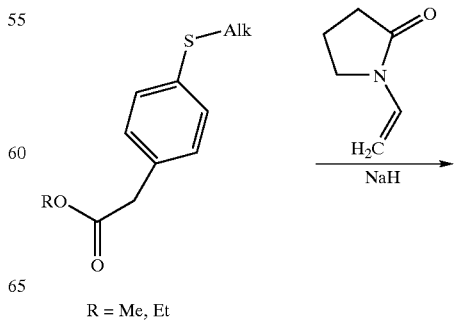

R = Me, Et

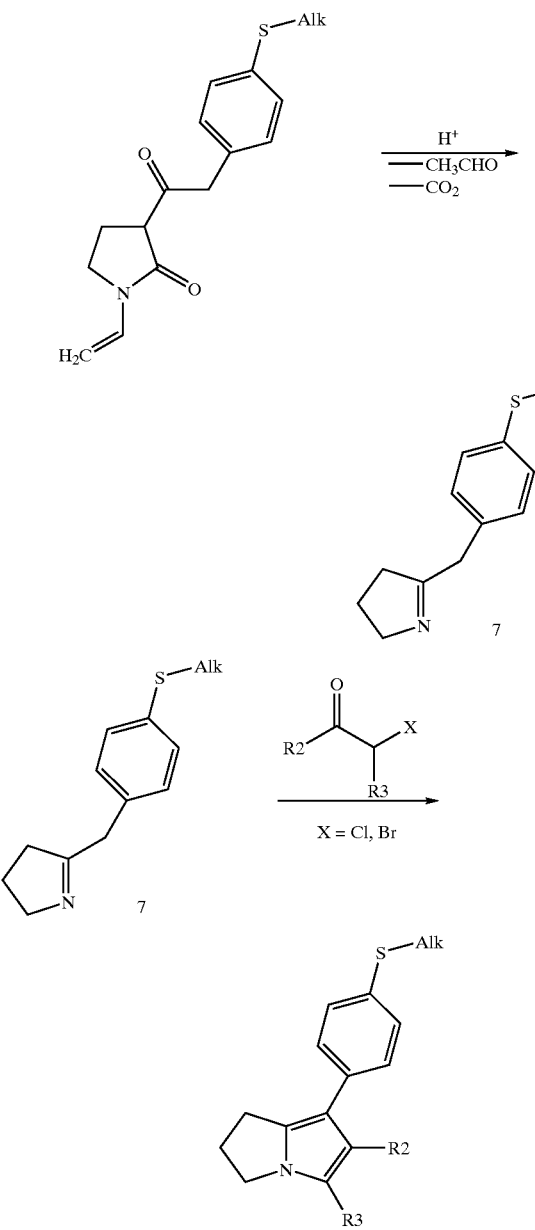

Example 6 (Alk = CH₃, R3 = H, R2 = 4-F—Ph—)

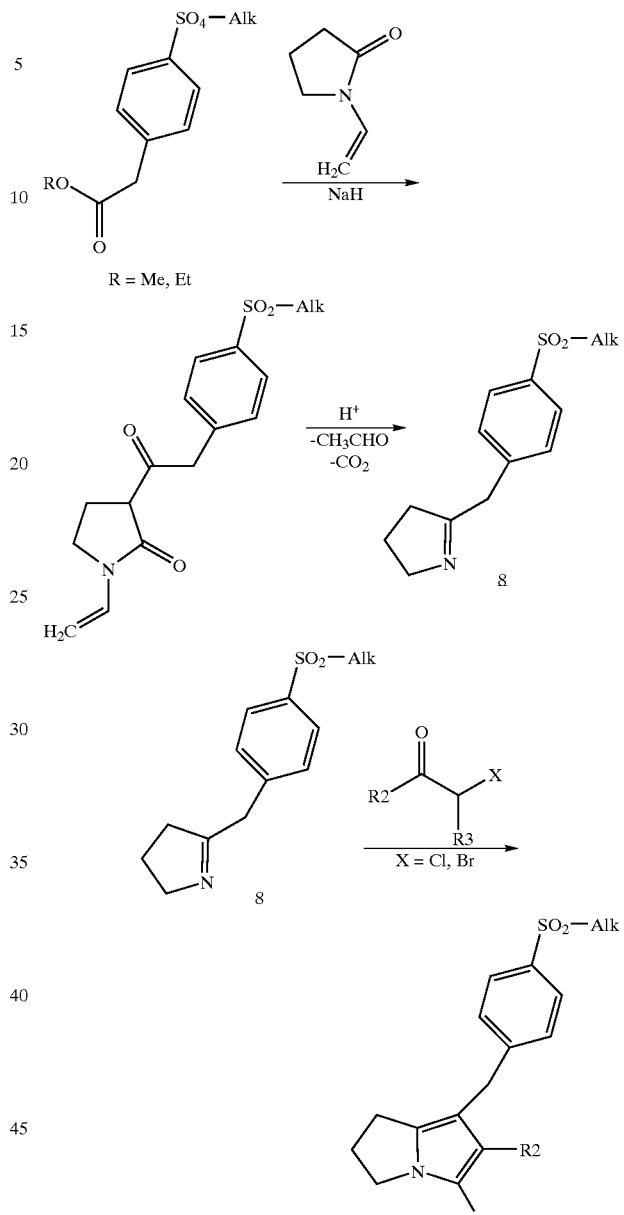

Example 8 (Alk = CH₃, R3 = H, R2 = 4-F—Ph—)

The necessary starting compounds 4-alkylmercaptophenylacetic acid esters, here methyl 4-methyl-mercaptophenylacetate, can be conveniently prepared starting from thioanisole via Friedel-Crafts acylation with acetyl chloride and Willgerodt-Kindler rearrangement with subsequent hydrolysis and ester formation. The 4-alkylsulphonylphenylacetic acid esters can be obtained in good yields from the 4-alkylmercaptophenylacetic acid esters by peracid oxidation, e.g. using m-chloroperbenzoic acid or $H_2O_2$ in glacial acetic acid, and can be condensed analogously to the sulphonyl compound to give a pyrroline 9 and cyclized to the pyrrolizine of Example 7 (Reaction 4).

Diarylpyrrolizine compounds according to the invention of the 6,7-(or 1,2-) diaryl series, in which the sulphur function is positioned in the para position on the aromatic to position 6 (or position 2) of the pyrrolizine can also be prepared from the corresponding phenacyl bromides which carry these sulphur functions in the case of the sulphanyl, sulphoxide, and of the sulphonyl and also the sulphamoyl compounds (Reaction 4b).

Thus, for example, the reaction of 2-bromo-1-(4-methylsulphanylphenyl)-1-ethanone with 2-benzyl-1-pyrroline yields the compound of Example 1, with 2-(4-fluorobenzyl)-1-pyrroline that of Example 4, the reaction of 2-bromo-1-(4-methylsulphinylphenyl)-1 thanone with 2-benzyl-1-pyrroline the compound of Example 2, the reaction of 2-bromo-1-(4-methylsulphonylphenyl)-1-ethanone with 2-benzyl-1-pyrroline that of Example 3, with 2-(4-fluorobenzyl)-1-pyrroline the compound of Example 5.

Acyl side chains can also be introduced in position 5 of the pyrrolizine in the said 6,7-(or 1,2) diarylpyrrolizine compounds by acylation in position 5 (or 3) and these can be converted by suitable reduction methods (HI reduction, NaCNBH₃ reduction, Vitride reduction etc.) into alkyl side chains.

Reaction 4b:

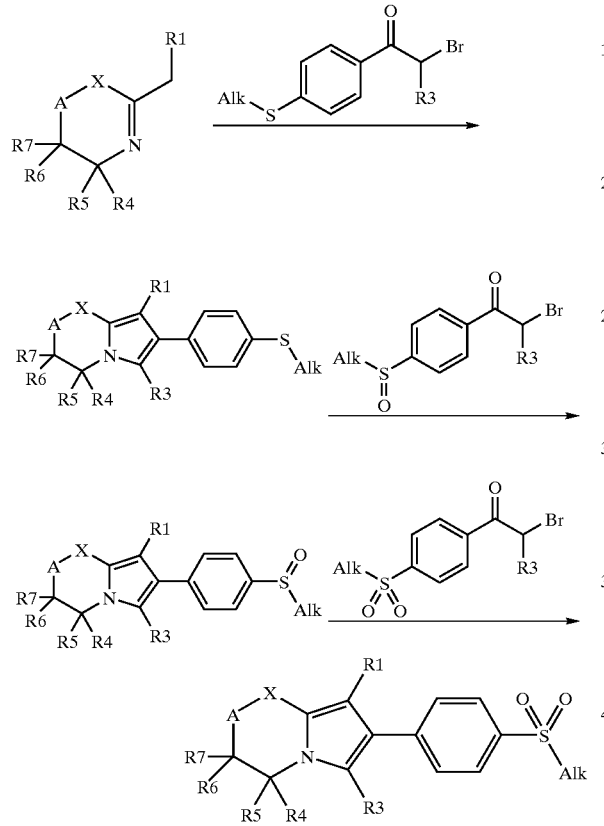

5,6-(or 2,3) diarylpyrrolizine compounds and 6,7-(or 2,3) diarylindolizine compounds according to the invention can be prepared in the manner of a 1,3-dipolar cycloaddition from corresponding münchnone or sydnone precursor compounds and suitable dienophiles or dipolarophiles. In this case, a sulphur function can be introduced on the one hand via the münchnone/sydnone component, on the other hand via the dipolarophile component. Dipolarophiles used are dehydrocinnamic acids or other acetylene carboxylic acids, 2-halo-substituted cinnamic acids or 2-haloacrylates and nitrostyrenes. In the pyrrolizine series, N-acyl derivatives of proline (pyrrolidine-2-carboxylic acid) and in the indolizine series N-acyl derivatives of the homologous piperidine-2-carboxylic acid are employed for sydnone formation.

For example, the cycloaddition of ethyl 2-bromo-3-(4-methylsulphanylphenyl)propenoate (10) to the munchnone of N-(4-fluorobenzoyl)proline (11, Reaction 5) produced in situ leads to the ethyl ester of the pyrrolizinecarboxylic acid of Example 11, that of ethyl 2-bromo-3-(4-methylsulphonylphenyl)-propenoate (12) to the ester from Example 12, and the cycloaddition of a 2-(4-methylsulphonyl-phenyl)-1-nitroethene (13) to the same münchnone leads to the pyrrolizine compound from Example 13A.

By the use of, for example, methyl dehydrocinnamate (14), 1-nitrostyrene or N-benzoylproline (15), unsubstituted 5,6-(or 2,3) diarylpyrrolizine compounds (Reaction 6) are first obtained into which a sulphur function can subsequently be introduced into the para ring position, for example, by chlorosulphonation.

Reaction 5:

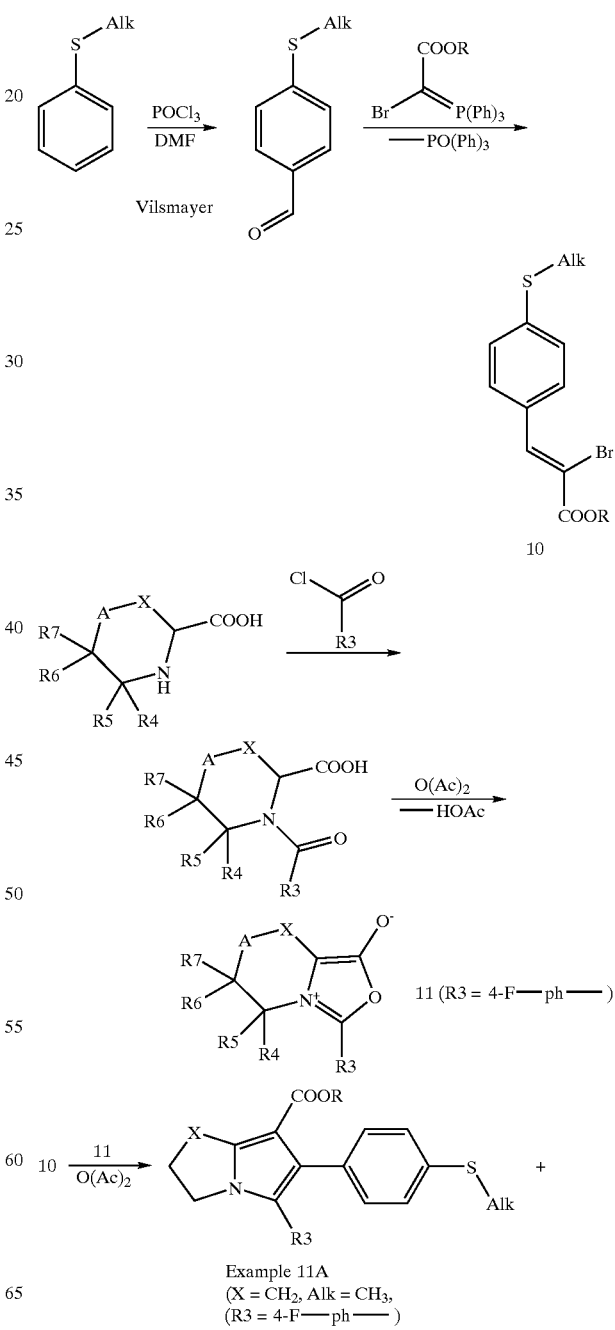

Example 11A
(X = CH₂, Alk = CH₃,
(R3 = 4-F—ph—)

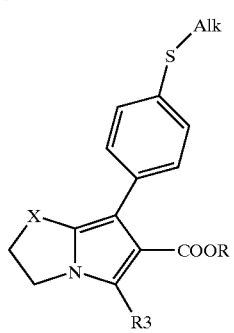
Example 11B
(X = CH₂, Alk = CH₃,
(R3 = 4-F—ph—)
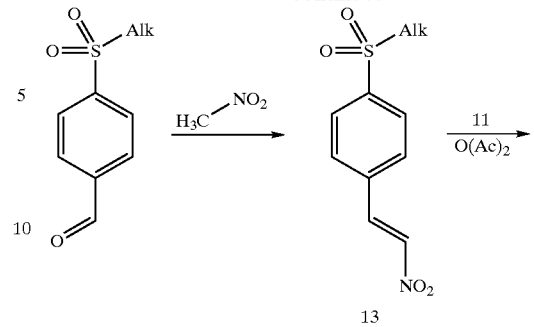
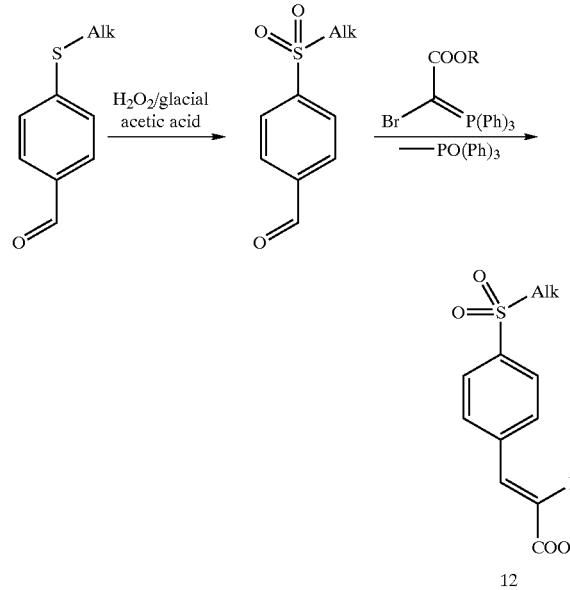
Example 12A
(X = CH₂, Alk = CH₃, R3 = 4-F—ph—)
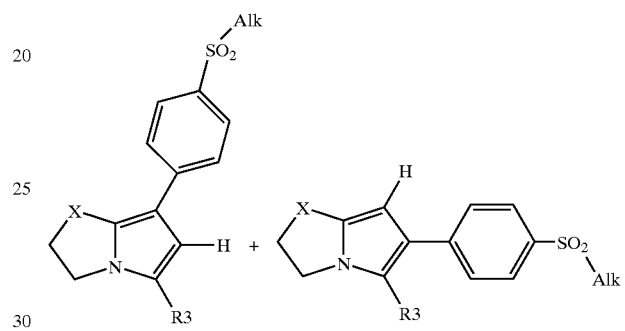
Example 13B                Example 13A
(X = CH₂, Alk = CH₃,      (X = CH₂, Alk = CH₃,
 R2 = 4-F—ph—)             R2 = 4-F—ph—)
Reaction 6:
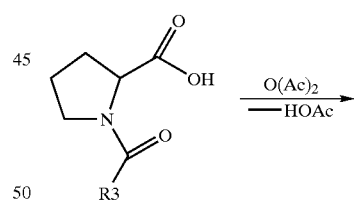
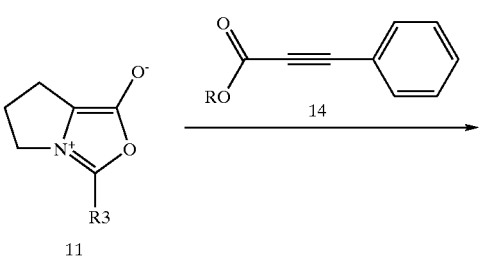
Example 12B
(X = CH₂, Alk = CH₃, R3 = 4-F—ph—)

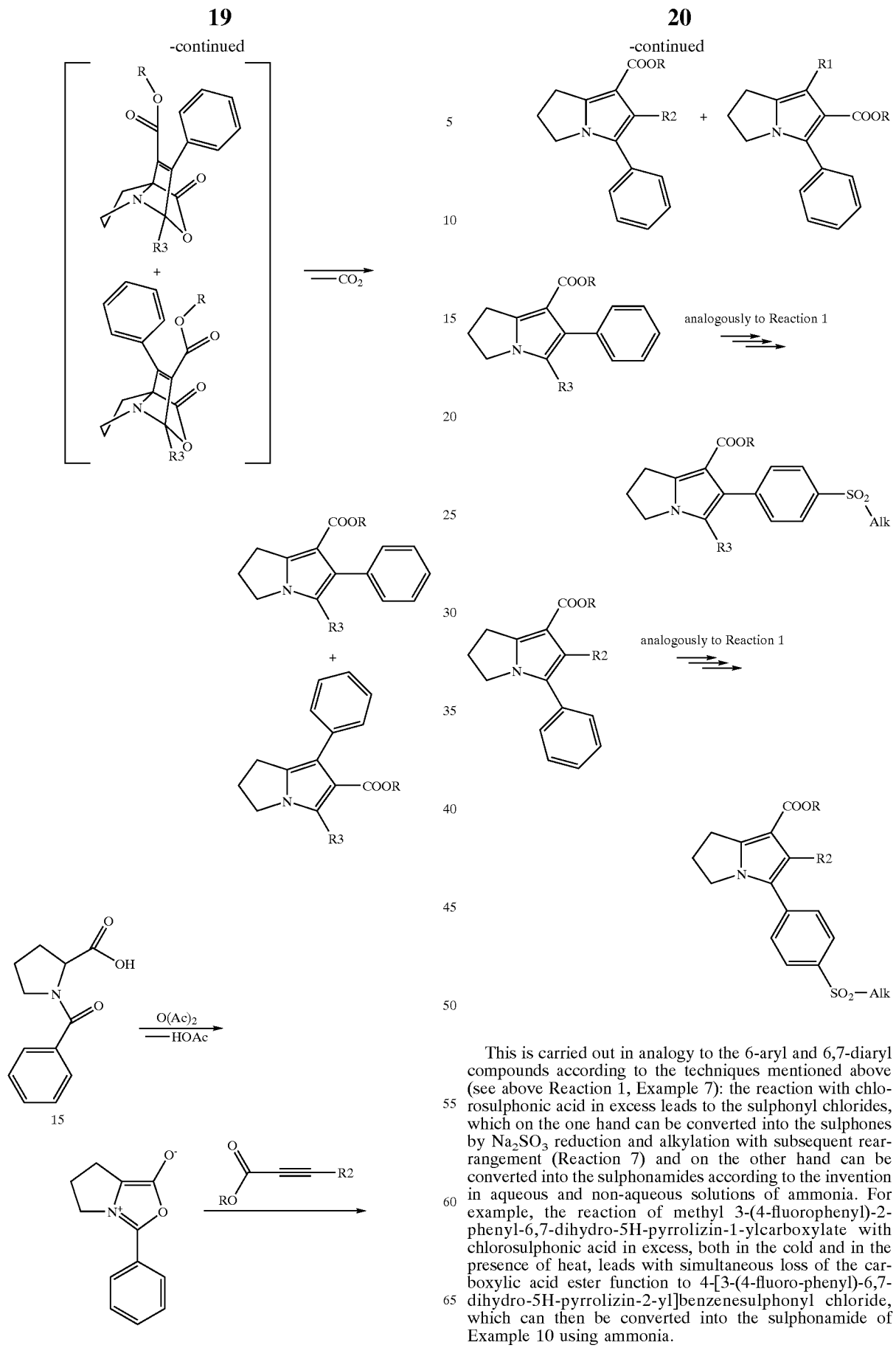

This is carried out in analogy to the 6-aryl and 6,7-diaryl compounds according to the techniques mentioned above (see above Reaction 1, Example 7): the reaction with chlorosulphonic acid in excess leads to the sulphonyl chlorides, which on the one hand can be converted into the sulphones by $Na_2SO_3$ reduction and alkylation with subsequent rearrangement (Reaction 7) and on the other hand can be converted into the sulphonamides according to the invention in aqueous and non-aqueous solutions of ammonia. For example, the reaction of methyl 3-(4-fluorophenyl)-2-phenyl-6,7-dihydro-5H-pyrrolizin-1-ylcarboxylate with chlorosulphonic acid in excess, both in the cold and in the presence of heat, leads with simultaneous loss of the carboxylic acid ester function to 4-[3-(4-fluoro-phenyl)-6,7-dihydro-5H-pyrrolizin-2-yl]benzenesulphonyl chloride, which can then be converted into the sulphonamide of Example 10 using ammonia.

Reaction 7:

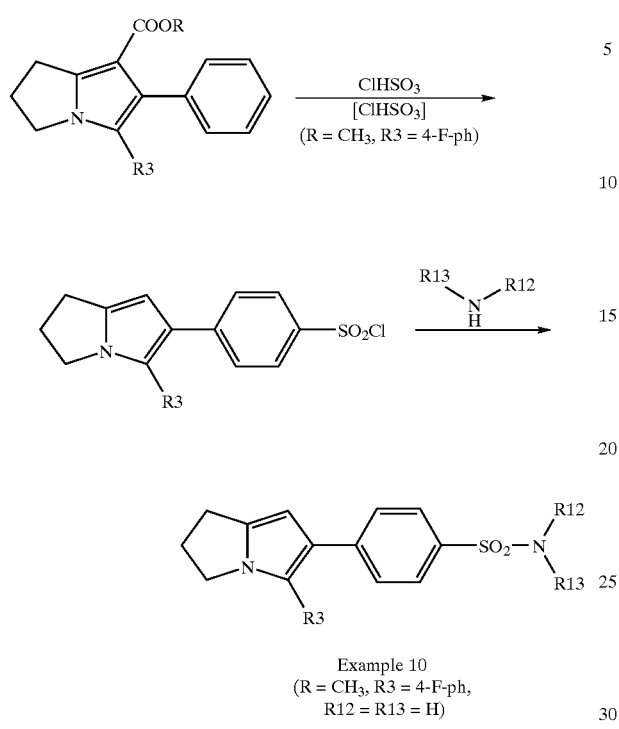

Example 10
(R = CH₃, R3 = 4-F-ph,
R12 = R13 = H)

A suitable alternative for access to 5,6-diaryl-substituted pyrrolizines is especially offered by arylation according to Suzuki if the sulphur-containing aromatic is introduced in position 5.

For example, the reaction of a 6-(4-fluorophenyl)-7-methyl-2,3-dihydro-1H-pyrrolizine, which was obtained from 2-ethyl-1-pyrroline and 2-bromo-1-(4-fluorophenyl)-1-ethanone, with N-bromo-succinimide in THF at low temperatures (−70° C. to 25° C.) yields a 5-bromo-6-(4-fluorophenyl)-7-methyl-2,3-dihydro-1H-pyrrolizine, which in the presence of tetrakistriphenylphosphinepalladium(0) can be condensed in aqueous/alkaline (e.g. $Na_2CO_3$/$CH_2Cl_2$) medium with 4-methyl-sulphanylphenylboronic acid according to Suzuki to give the methylsulphanyl compound from Example 9 (Reaction 8).

A suitable starting point for the 6-alkyl-7-(4-sulphamoylphenyl)-substituted pyrrolizines is also 7-phenyl-2,3-dihydropyrrolizine, which can be halogenated in position 5 by NBS in THF or can be acylated in position 5 with reaction with acylating compounds such as acid chlorides and acid anhydrides (Reaction 9).

Reaction 8:

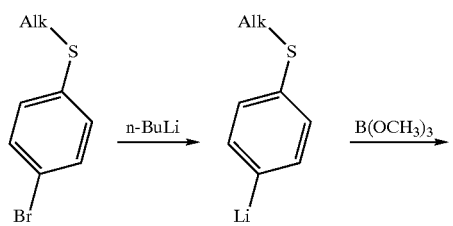

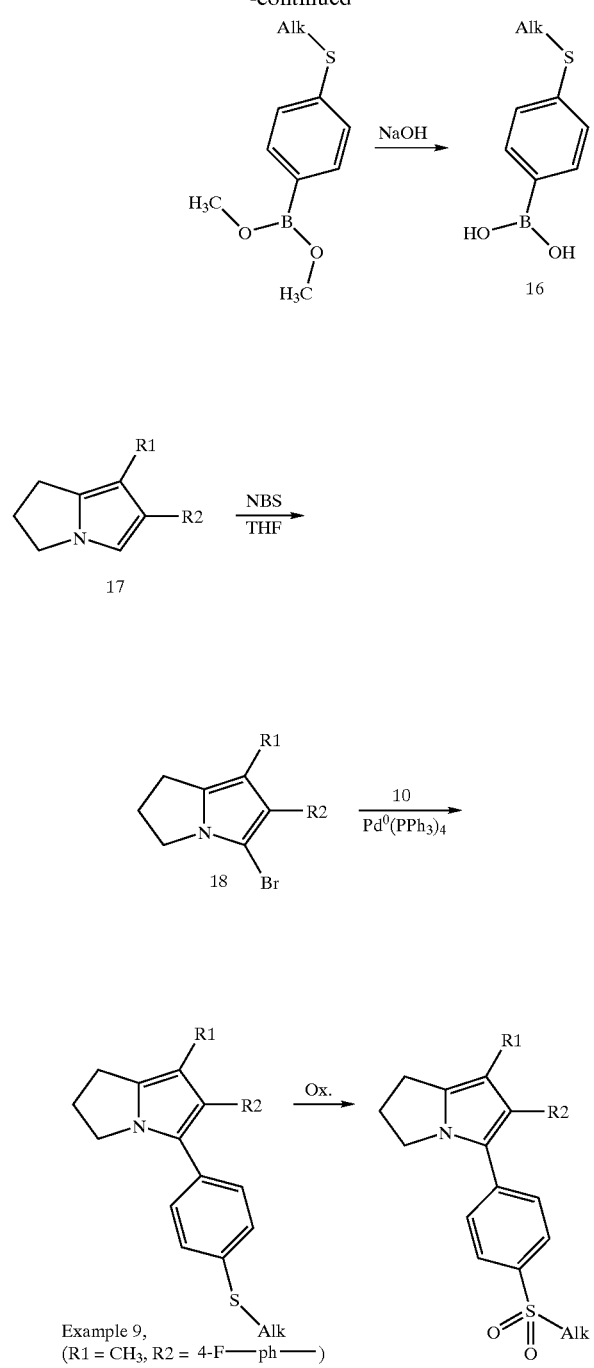

Reaction 9:

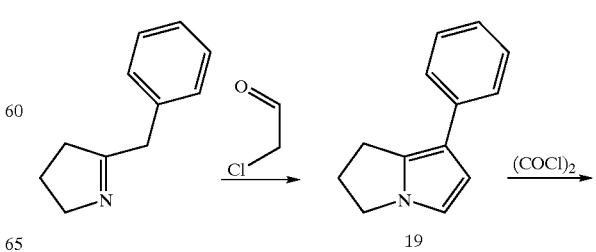

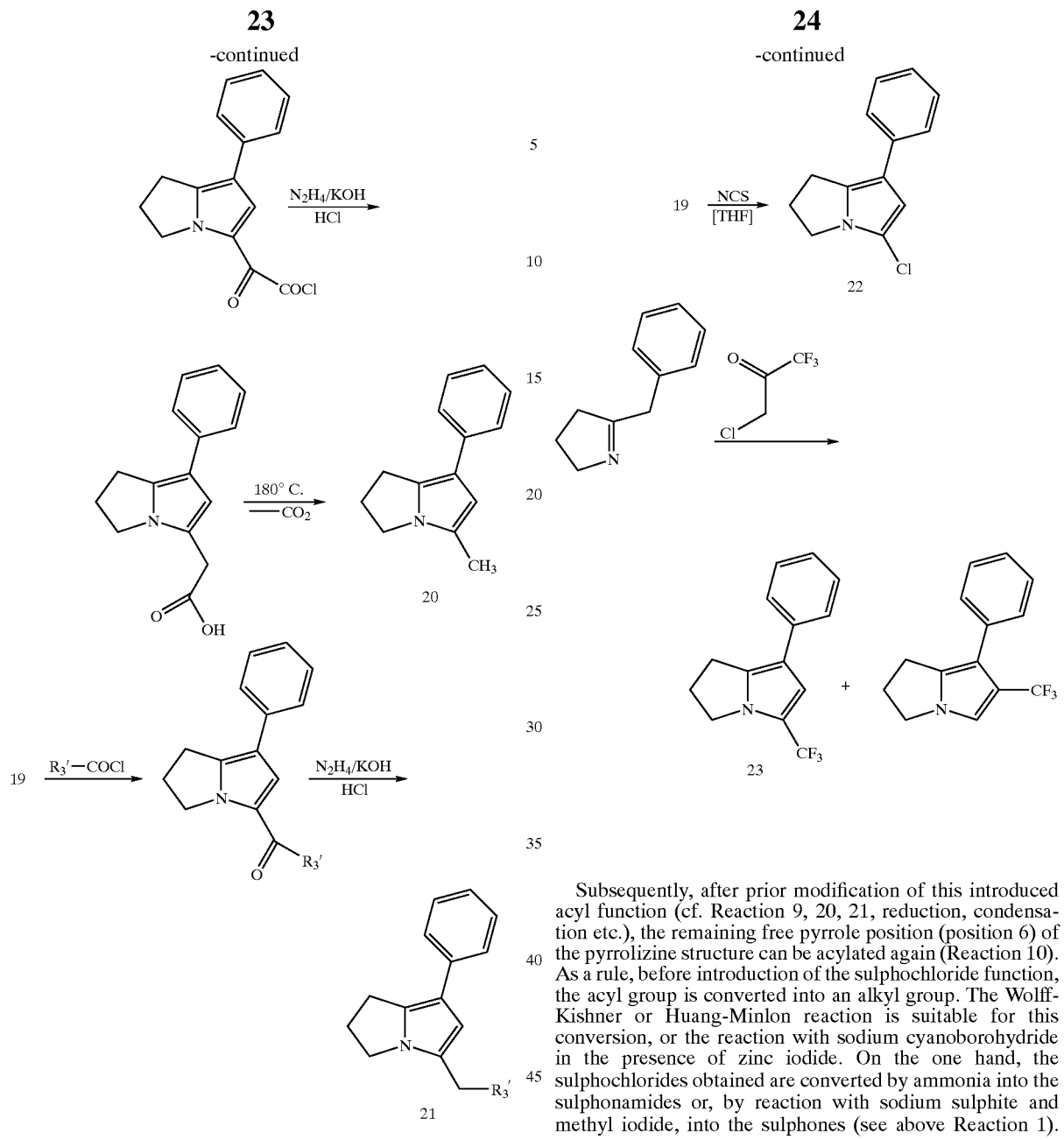

Subsequently, after prior modification of this introduced acyl function (cf. Reaction 9, 20, 21, reduction, condensation etc.), the remaining free pyrrole position (position 6) of the pyrrolizine structure can be acylated again (Reaction 10). As a rule, before introduction of the sulphochloride function, the acyl group is converted into an alkyl group. The Wolff-Kishner or Huang-Minlon reaction is suitable for this conversion, or the reaction with sodium cyanoborohydride in the presence of zinc iodide. On the one hand, the sulphochlorides obtained are converted by ammonia into the sulphonamides or, by reaction with sodium sulphite and methyl iodide, into the sulphones (see above Reaction 1).

Reaction 10:

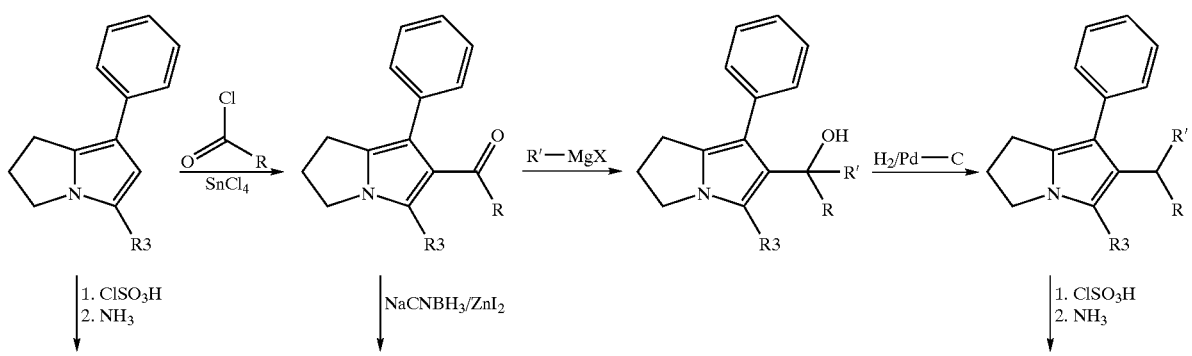

-continued

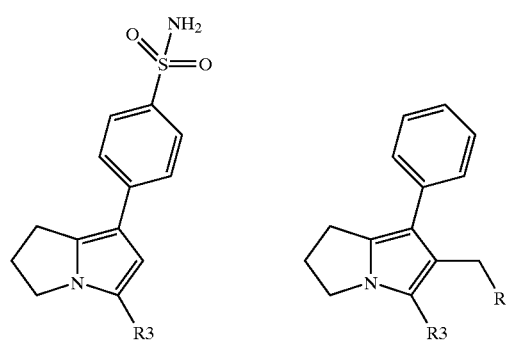

Example 30
(R3 = CH₃)

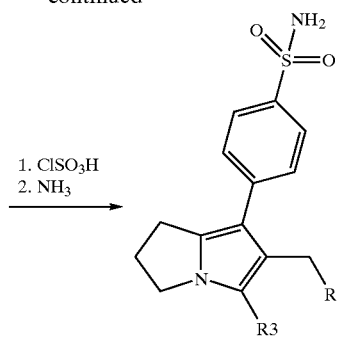

1. ClSO₃H
2. NH₃

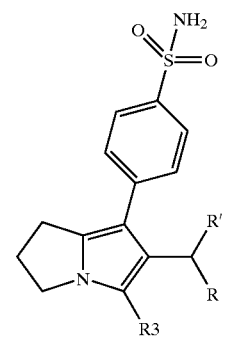

Example 35
(R3 = CH₃,
R = CH(CH₃)₂)

Example 39
(R3 = CH₃,
R = R' = CH₃)

As a starting point for the synthesis of cycloaliphatically substituted pyrrolizines, e.g. of the 6-cyclohexyl derivatives, the acylated cycloaliphatics (e.g. cyclohexyl methyl ketone) can be used. Their bromination also leads to the desired bromoacetyl compounds. The reaction of the 1-acetyl-1-ethoxycarbonylcycloalkyl, e.g. of 1-acetyl-1-ethoxycarbonylcyclohexane, with bromine to give 1-bromoacetyl-1-ethoxycarbonylcyclohexane, which also cyclizes smoothly to give a pyrrolizine with pyrrolines, is more advantageous. Comparably to 1-phenyl-6,7-dihydro-5H-pyrrolizin-3-yl acetic acid in Reaction 9 (preparation of compound 20), the 6-ylacetic acid is also unstable and decarboxylates at elevated temperature (Reaction 11, 24-COOH).

Reaction 11:

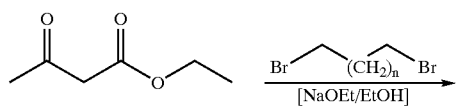

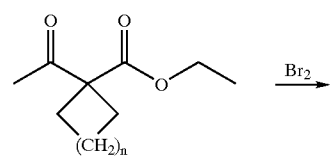

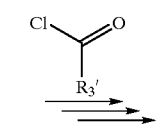

-continued

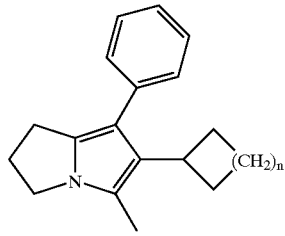
24

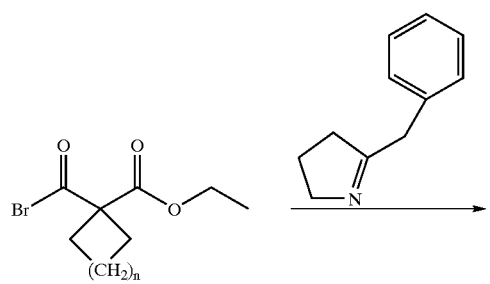

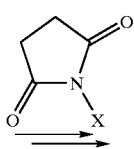
24

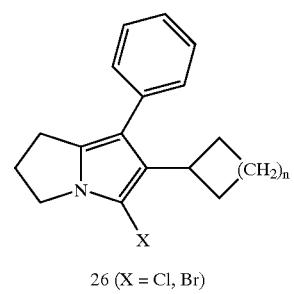

25

26 (X = Cl, Br)

In this case, the ethoxycarbonyl group functions as a protective group for the branching position in the cycloaliphatic. Finally, the sulphochlorides are also obtained here using chlorosulphonic acid, and on the one hand are converted by ammonia into the sulphonamides (cf. Example 14) or into the sulphones by reaction with sodium sulphite and methyl iodide (Reaction 12).

Reaction 12:

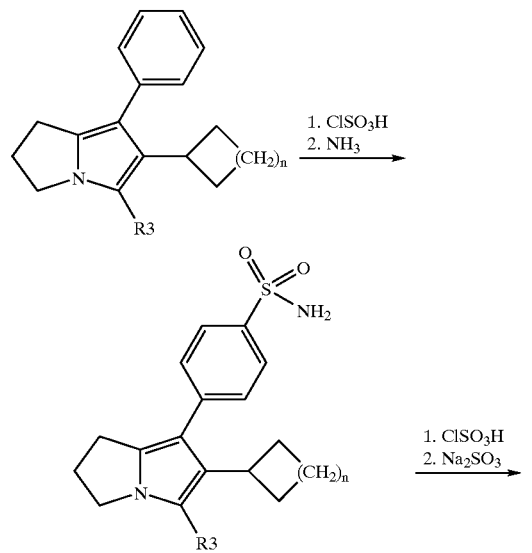

Example 14
(R3 = CH₃, n = 3)

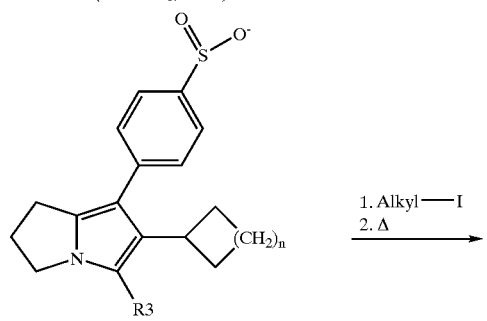

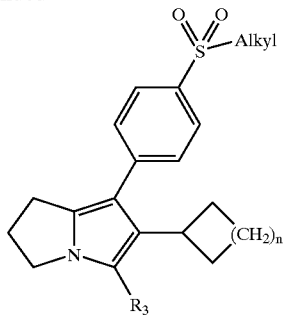

The intermediately obtained pyrrolizines, as well as the pyrrolizines carrying sulphur functions, can be converted further in different ways, for example further functional groups can be introduced into the activated positions of the pyrrolizine nucleus, as is carried out in WO 95/23970 and WO 95/23971. The α-positions of the aliphatic fused ring adjacent to the pyrrole nucleus (position 1, or 7) can be functionalized by suitable methods: free-radical bromination with N-bromosuccinimide in aprotic solvents yields 1-bromo (or 7-bromo) derivatives, and in aqueous systems and in an excess of the reagent the 1-oxo derivatives of the pyrrolizines.

When using 1 molar equivalent of N-bromosuccinimide, the compound of the formula 25 brominated in the 1-position is obtained (Reaction 13). This in turn can then be reacted with acylates, for example sodium acetate or alkoxides, such as sodium methoxide or sodium ethoxide, to give the corresponding compounds of the formulae 26 and 27 (Reaction 13). The reactions are carried out in a known manner, the reaction with the acylates takes place in an inert solvent, for example dimethylformamide (DMF), at elevated temperature, e.g. 70 to 90° C. The reaction of the compounds of the formula 25 with alkoxides is expediently carried out in the corresponding alcohol. Alternatively, the compounds of the formula 25 (Reaction 13), if desired without being isolated from the reaction mixture, can be reacted directly with an alcohol to give the compounds of the formula 27.

Alternatively, a compound of the formula R can be reacted with one molar equivalent of NBS in a chlorinated solvent in the presence of water to give a compound of the formula 28. Using a further molar equivalent of NBS, a compound of the formula 29 is then obtained.

Reaction 13:

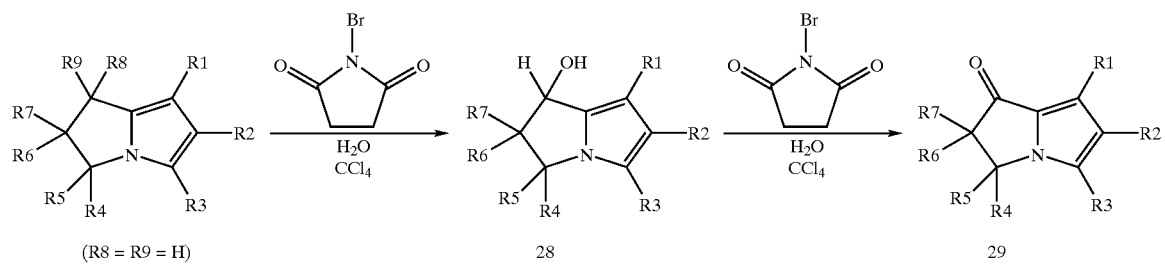

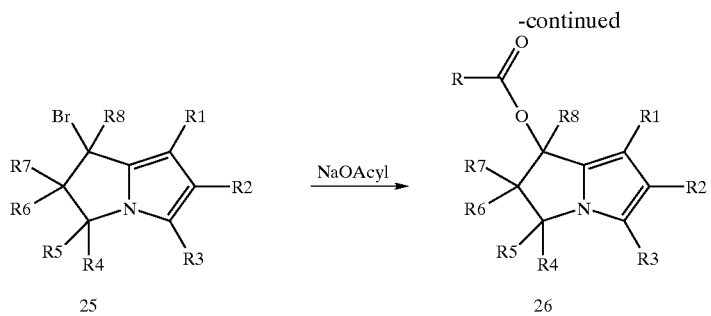

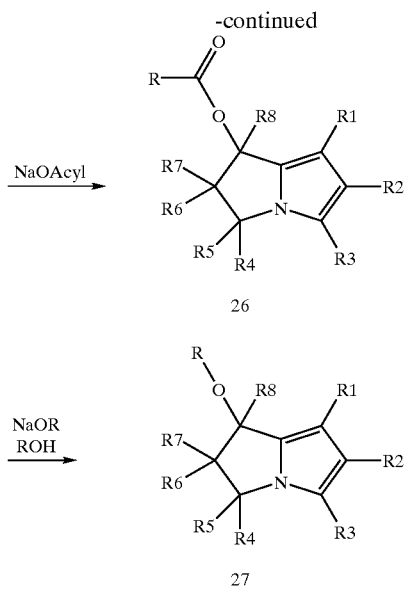

The introduction of polar groups on the hydrocarbon skeleton of the fused ring, i.e. in the position of the substituents R4–R11, such as hydroxyl groups (Reaction 14, 30), amino groups (Reaction 14, 311 Z=NR$_2$), carbonyl (Reaction 14, 32) and carboxyl groups (Reaction 14, 33) presupposes a modified synthesis strategy. Such functional groups can only be indirectly introduced subsequently on the hydrocarbon skeleton of the fused ring. The preparation is carried out by means of suitable precursors which already contain these functional groups, protected by so-called protective groups (=Pg) or can subsequently be converted into the desired group from a suitable precursor group (e.g. 30).

Reaction 14 shows an example of how, using the methodology described in EP 0397175, starting here from trishydroxymethylene derivatives (R4–R6=H, R8=R9=H, R7=CH$_2$OH) by selective introduction of a protective group for one of the 3 hydroxymethylene groups, compounds of the structure 30, 31, 32 and 33 can be obtained which contain the corresponding substitution pattern with functional groups. These compounds (30, 31, 32 and 33) occur in the form of two optical antipodes which, if required, are separated by use of chromatographic techniques or are separated using customary purification methods at the stage of diastereomeric synthesis intermediates (acetals or ketals where R=H, R'=alkyl, aryl etc, or R=R'=alkyl, aryl etc.). after their preparation and which yield the pure enantiomers of the precursors after recleavage.

Reaction 14:

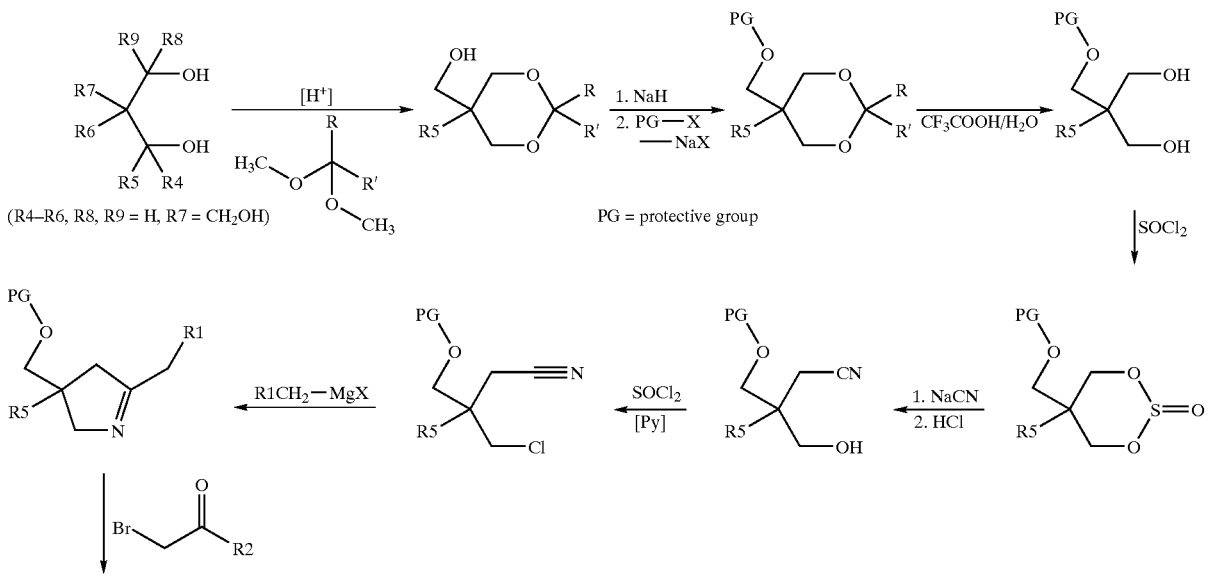

-continued

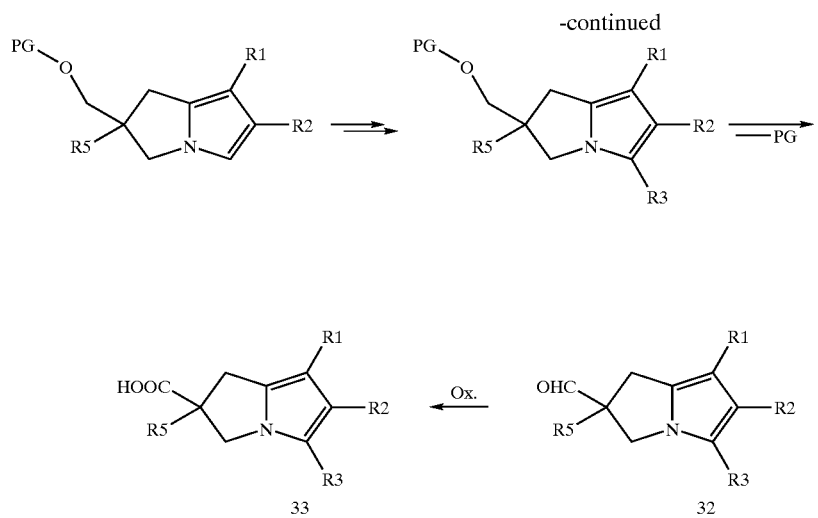

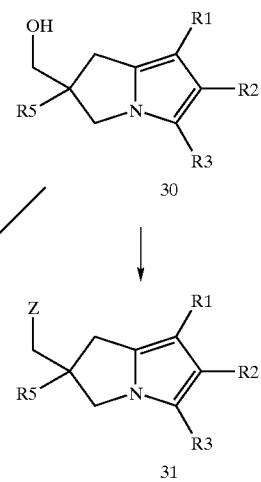

In vitro, the compounds according to the invention show a marked inhibition of the release of proinflammatory mediators of the arachidonic acid cascade and thus in vivo antipyretic, analgesic and anti-inflammatory action in inflammation models. The compounds according to the invention inhibit prostaglandin H synthase, the key enzyme of prostaglandin synthesis. In this case, its isoform 2 shows an increased sensitivity to the compounds according to the invention, so that these act as selective inhibitors of isoenzyme-2. The compounds thus allow a markedly decreased side-effect profile, in particular on the kidney and GI tract, to be expected.

The compounds also exert a weak to medium inhibitory action on 5-lipoxygenase, a further enzyme of arachidonic acid metabolism. Using the inhibitory action on 5-LO, similarly to dual inhibitors of cyclooxygenase-1/2 (COX-1/COX-2) and of 5-lipoxygenase (5-LOX), the disadvantageous effects of a pure COX-1 inhibition on bronchi (asthma) and GI tract (lesions) can be compensated.

The compounds according to the invention are thus suitable for the treatment of disorders in which increased release rates of the eicosanoid mediators are responsible for the formation or the progressive course of these disorders. In particular, the compounds according to the invention, can be used for the treatment of disorders of the rheumatic type and for the prevention of allergically induced disorders. The compounds according to the invention are thus efficacious anti-inflammatories, analgesics, antipyretics, antiallergics and broncholytics or have antibronchoconstrictor activity and can therefore be used for thrombosis prophylaxis and for the prophylaxis of anaphylactic and septic shock as well as for the treatment of dermatological disorders, such as psoriasis, urticaria, acute and chronic exanthema, of allergic and non-allergic genesis.

The compounds according to the invention have increased chemical stability, parenteral administrability, enteral bioavailability and short half-lives.

The compounds according to the invention can either be administered as individual therapeutic active compounds or as mixtures with other therapeutic active compounds: they can be administered as such, but in general they are administered in the form of pharmaceutical compositions, i.e. as mixtures of the active compounds with pharmaceutically acceptable excipients, in particular vehicles or diluents and/or additives. The compounds or compositions can be administered enterally, e.g. orally or rectally, or parenterally, e.g. subcutaneously, intravenously or intramuscularly, but they are preferably given in oral dose forms.

The nature of the pharmaceutical composition and of the pharmaceutical carrier or diluent depends on the desired manner of administration. Oral compositions can be present, for example, as tablets or capsules and can contain customary excipients, such as binding agents (e.g. syrup, acacia, gelatin, sorbitol, tragacanth or polyvinylpyrrolidone), fillers (e.g. lactose, sugar, maize starch, calcium phosphate, sorbitol or glycine), lubricants (e.g. magnesium stearate, talc, polyethylene glycol or silica), disintegrating agents (e.g. starch) or wetting agents (e.g. sodium laurylsulphate). Oral liquid preparations can be present in the form of aqueous or oily suspensions, solutions, emulsions, syrups, elixirs or sprays etc. or can be present as dry powders for reconstitution with water or another suitable carrier. Liquid preparations of this type can contain customary additives, for example suspending agents, flavourings, diluents or emulsifiers. For parenteral administration, solutions or suspensions with customary pharmaceutical carriers can be employed.

The use of compounds according to the invention in the course of treatment comprises a process. In this case, an efficacious amount of one or more compounds, as a rule formulated corresponding to pharmaceutical and veterinary practice, is administered to the individual to be treated, preferably a mammal, in particular a human, agricultural animal or pet. Whether such a treatment is indicated and in which form it has to be carried out, depends on the individual case and is subject to medical assessment (diagnosis) which includes present signs, symptoms and/or dysfunctions, risks of developing specific signs, symptoms and/or dysfunctions, and further factors.

As a rule, the treatment is carried out by administration one or more times daily, if appropriate together or alternately with other active compounds or active compound-containing preparations, so that a daily dose of approximately 0.1 mg to approximately 1000 mg and in particular 0.5 mg to approximately 100 mg per kg of body weight is administered to an individual to be treated.

The following examples explain the invention without restricting it.

FIGS. 1 to 9 show spectroscopic data of the compounds prepared according to Examples 1 to 36;

FIGS. 10 and 11 show biological activity data of some compounds according to the invention and of known compounds for comparison.

SYNTHESIS

| In general, the abbreviations have the following meanings | |
|---|---|
| Mp: | melting point |
| Bp: | boiling point |
| dec: | decomposition |
| TLC: | thin-layer chromatography |
| CC: | column chromatography |
| GC: | gas chromatography |
| Y: | yield |
| TY: | total yield |
| abs. | absolute |
| In the context of NMR, the abbreviations have the following meanings | |
| arom: | aromatic; |
| quin: | quintuplet; |
| br: | broad; |
| t: | triplet; |
| m: | multiplet; |
| s: | singlet; |
| q: | quadruplet; |
| d: | doublet |

The melting points were determined on a Mettler FP 51 or on a Buchi Melting Point B 545: heating rate 2° C./min, average value (40% threshold) of 3 measurements with a regular melting course (melting course diagram), calibration against vanillin (83.0° C.), phenacetin (136.0° C.) and caffeine (237° C.). The IR spectra were recorded on a Shimadzu IR 470; or FT-IR Nicolet Impact 410, on the latter processed using Omnic (Version 2.1). For this, the substance was compressed in KBr tablets or measured as a film between NaCl plates in transmitted light.

The NMR spectra were recorded on a Bruker AC 200 (1H: 200 MHz, 13C: 50.3 MHz). For this, 20–50 mg of substance, in about 0.5–1.0 ml of a deuterated solvent which contained 0.1% of tetramethylsilane as an internal standard, were dissolved to give a clear solution. The solution was transferred to a 0.5 cm sample tube in the sample space. For 1H-NMR spectra, as a rule 32 FIDs were summed under D-lock for 1H-NMR spectra and converted into frequency spectra by the FT process; for the recording of 13C-NMR spectra between 500 and 10,000 FIDs were collected.

UV spectra Were recorded on a UV Perkin-Elmer 550 SE UV/VIS spectroscope. Measurement was carried out in 1 cm quartz cuvettes in a suitable solvent.

Mass spectra were recorded on a GC-MS system HP-MSD (HP 6890 GC-HP 5973 MSD); after GC separation in a high vacuum ($10^{-6}$ Torr) excitation was carried out by EI, at an electron energy of 70 eV.

The determination of volatile and thermostable compounds was carried out by means of GC on GC-MSD. Separation was carried out, if no other details are given, on an HP-5MS column (30 m, 0.25 mm, 5% phenylmethylsilicone, 0.25 µm) using helium at a constant flow of 1.2 ml and a split ratio of 50:1 according to the area method of TIC.

The determination of poorly volatile and thermolabile compounds was carried out by means of HPLC on a Merck-Hitachi HPLC (L4000 detector, L6200A intelligent pump, D 2500 chromato-integrator) according to the area method; UV absorption measured at the absorption maximum or at 256 nm. The column (if not stated otherwise LiChroCART 125-4; LiChrosphere 100 RP-18; 5 µm; from Merck, Darmstadt) was thermostated using a WO Electronics BFO-04 SV column oven (30° C.). As a rule separation was carried out using a gradient of a ternary mixture of methanol, acetonitrile and a 5 mmol $NaH_2PO_4$ buffer which is maintained at a pH of 3.5 using $H_3PO_4$, using a flow rate of 1 ml/min after injection of 20 µl of a solution of 30–40 mg of the substance to be investigated in 100 ml of MeOH.

EXAMPLE 1

2-(4-Methylmercaptophenyl)-1-phenyl-6,7-dihydro-5H-pyrrolizine a) 3-Phenylacetyl-1-vinylpyrrolidin-2-one (according to Ref. Haslego M. L., Maryanoff C. A., Scott L., and Sorgi K. L., Heterocycles, 35, 643–647 (1993))

Sodium hydride (300 g, 60% strength in white oil, 7.5 mol) is suspended under nitrogen in abs. THF (tetrahydrofuran) (1400 ml) in a 3 l three-necked flask and the suspension is heated for 30 min, during which the initial evolution of hydrogen subsides. The mixture is allowed to cool to RT (room temperature) and a mixture of ethyl phenylacetate (457 g, 2.78 mol) and 1-vinyl-2-pyrrolidone (278 g, 2.5 mol) in THF abs. (400 ml) is then added dropwise via a dropping funnel.

The addition rate is chosen such that the evolution of hydrogen can be kept under control (3.5 h). After complete addition, reflux (66° C., IT (internal temperature)) is maintained for a further 3 h; the mixture is cooled to RT and allowed to stand for 16 h. The excess of sodium hydride is destroyed by cautious addition of a saturated (37% strength) ammonium chloride solution (2 l) to the starting solution. The organic phase is separated in a separating funnel, dried with $Na_2SO_4$ and the filtrate is concentrated. The white oil depositing as an independent phase is decanted off. An oily residue of 569 g (99.4%) having a purity of 90% GC (gas chromatography) remains: 8–9% of ethyl phenylacetate. The material obtained can be employed in the next step without further purification.

IR (NaCl): 1/λ ($cm^{-1}$)=3307 (br), 3030 (CH), 2960, 2893 (CH), 1693 (CO), 1633, 1454, 1427, 1389, 1279, 700;

$^1$H-NMR (CDCl$_3$): δ (ppm)=7.37–7.15 (m, 5H, arom), 7.09–6.97 (AB<u>X</u>, 1H, N—CH=), 4.52–4.40 (<u>AB</u>X, 2H, =CH$_2$), 4.19–4.00 (AB, 2 H, PhCH$_2$CO), 3.82–3.73 (m,1 H, 3-H), 3.53–3.39 (m, 2 H, 5-CH$_2$), 2.80–2.40 (m,1 H, 4-H), 2.20–1.90 (m, 1 H, 4-H);

$^{13}$C-NMR (CDCl$_3$): δ (ppm)=203.0 (CO), 173.3 (CONR), 133.7 (C-quart.), 129.7, 128.6, 126.9 (CH), 52.7 (C-3), 49.3 (CH$_2$), 40.3 (CH$_2$), 22.4 (CH$_2$).

b) 2-Benzyl-1-pyrroline (according to Ref. Haslego M. L., Maryanoff C. A., Scott L., and Sorgi K. L., Heterocycles, 35, 643–647 (1993))

A 6 N HCl solution is prepared in a 5 l three-necked flask using water (1.3 l) and HCl (36%, 1.3 l, 15 mol), and this is then heated to reflux. The crude 3-phenylacetyl-1-vinylpyrrolidin-2-one (552 g, 2.5 mol) in THF (1 l) is added dropwise to the hot acid via a dropping funnel, and the volatile acetaldehyde immediately released is distilled from the mixture via a distillation bridge (time needed 2 h).

The mixture is kept under reflux for a further 16 h and, after cooling in an ice bath, treated with toluene (0.7 l) at RT. The organic phase is separated in a separating funnel and the HCl phase is extracted with diethyl ether (0.7 l). The extracts are discarded. The aqueous phase is rendered alkaline (pH 9–10) using sodium hydroxide solution (32%, 1l, 10 mol) while cooling with crushed ice (0.4 kg). The oil depositing in the course of this is taken up in diethyl ether (0.7 l), and the separated aqueous phase is extracted again with diethyl ether (0.7 l). The combined ether solution is washed with water (1 l), dried over $Na_2SO_4$ sicc. (dried), and the filtrate is concentrated. 304 g (75%) of 2-benzyl-1-pyrroline of 90% purity (GC) are obtained.

Y: 75%=304 g (90%); Mp: oily; IR (NaCl): $1/\lambda$ $(cm^{-1})$= 3350 (br), 3028 (CH), 2958, 2868 (CH), 1641, 1603, 1495, 1454, 1429, 704; $^1$H-NMR ($CDCl_3$): δ (ppm)=7.35–7.19 (m, 5H, CH, arom), 3.88–3.78 (t, 2H, 5-$CH_2$), 3.68 (br, 2H, $PhCH_2$), 2.44–2.34 (t, 2H, 3-$CH_2$), 1.91–1.75 (quin, 2H, 4-$CH_2$); $^{13}$C-NMR ($CDCl_3$): δ (ppm)=176.8 (C-2), 136.8 (C-quart.), 128.9, 128.5, 126.5 (CH), 60.7 ($CH_2$), 40.5 ($CH_2$), 36.4 ($CH_2$), 22.5 ($CH_2$).

c) 2-(4-Methylmercaptophenyl)-1-phenyl-6,7-dihydro-5H-pyrrolizine

2-Benzyl-1-pyrroline (2.0 g, 80% strength, 10 mmol), dissolved in MeOH (30 ml), is treated with a solution of 2-bromo-1-(4-methylsulphanylphenyl)-1-ethanone (Example 2, 2.0 g, 8 mmol) in $CH_2Cl_2$ (10 ml) and then with $NaHCO_3$ (1.5 g, 18 mmol). The mixture is stirred at RT until a TLC sample ($Al_2O_3$, hexane/ether 9:1) indicates the complete reaction of the bromoketone (Rf 0.75) and an adequate formation of product (Rf=0.5) (48 h). After addition of water (50 ml), the mixture is extracted with diethyl ether (3×30 ml) and the combined extracts are dried over $Na_2SO_4$ sicc. and concentrated. The residue is purified by CC ($Al_2O_3$, hexane/ether 9:1). 0.62 g (25.2%) of the compound sought is isolated.

Mp: 112° C. IR (NaCl): $1/\lambda$ $(cm^{-1})$=3050, 1695, 1595, 1521, 1484, 1335, 1179, 1003; $^1$H-NMR ($CDCl_3$): δ (ppm)= 7.25–7.10 (m, 9H, arom), 6.72 (s, 1H, CH), 3.98 (t, 2H, $CH_2$), 2.96 (t, 2H, $CH_2$), 2.52–2.48 (quin, 2H, $CH_2$), 2.44 (s, 3H, $SCH_3$).

EXAMPLE 2

2-(4-Methylsulphinylphenyl)-1-phenyl-6,7-dihydro-5H-pyrrolizine a) 1-(4-Methylsulphanylphenyl)-1-ethanone Acetyl chloride (8.2 g, 0.105 mol) is added to a suspension of $AlCl_3$ (16 g, 0.12 mol) in dichloroethane (50 ml) cooled to 0° C.; the mixture is stirred for 15 min and a solution of thioanisole (12.4 g, 0.1 mol) in dichloroethane (20 ml) is then added dropwise; the temperature is kept below 20° C. by cooling (30 min). The mixture is stirred for a further 1 h and allowed to stand at RT overnight. The Lewis acid complex is decomposed by addition of ice water (100 ml) with cooling, the organic phase is separated in a separating funnel, and the aqueous phase is extracted a further 2 times with dichloroethane (100 ml). The combined extracts are dried over $Na_2SO_4$ sicc. and concentrated to ¼ of the starting volume. The red-brown residue (15.2 g) is washed with diethyl ether (20 ml) and hexane (20 ml): 12 g of light red (brick-red) substance result.

Y: 72% (12 g) $C_9H_{10}OS$, MW=166.24; IR (NaCl): $1/\lambda$ $(cm^{-1})$=1664; $^1$H-NMR ($CDCl_3$): δ (ppm)=7.89–7.85 (m, 2H, AA', arom), 7.28–7.24 (m, 2H, BB', arom), 2.57 (s, 3H, $COCH_3$), 2.52 (s, 3H, $SCH_3$).

b) 2-Bromo-1-(4-methylsulphanylphenyl)-1-ethanone

A solution of bromine (4.8 g, 30 mmol) in $CH_2Cl_2$ (20 ml) is added dropwise at room temperature in the course of one hour to a solution of 1-(4-methylsulphanylphenyl)-1-ethanone (5 g, 30 mmol) in $CH_2Cl_2$ (10 ml). The mixture is stirred further for one hour until the disappearance of the starting material (TLC checking $SiO_2$, $CH_2Cl_2$/hexane 1:1). After this, it is poured onto water (30 ml), the aqueous phase is separated and the organic phase is washed with $NaHCO_3$ soln (20 ml, 8% strength) until neutral, then dried ($Na_2SO_4$ sicc.) and concentrated.

Y: 95% (7.0 g), $C_9H_9BrOS$, MW=245.14; Mp: 67–68° C. from hexane; IR (NaCl): $1/\lambda$ $(cm^{-1})$=3005, 2945, 1687, 1581, 1551, 1402, 1313, 1281, 1202, 1189, 1091, 992, 969, 956, 816, 728, 660; $^1$H-NMR ($CDCl_3$): δ (ppm)=8.20–8.05 (AA'BB', 4H, arom), 4.46 (s, 2H, $CH_2Br$), 3.10 (s, 3H, $SCH_3$).

b') 2-Chloro-1-(4-methylsulphanylphenyl)-1-ethanone

Chloroacetyl chloride (11.8 g, 0.105 mol) is added to a suspension of $AlCl_3$ (16 g, 0.12 mol) in dichloroethane (50 ml) cooled to 0° C.; the mixture is stirred for 15 min and a solution of thioanisole (12.4 g, 0.1 mol) in dichloroethane (20 ml) is then added dropwise; the temperature is kept below 20° C. by cooling (30 min). The mixture is stirred for a further 1 h and then decomposed by addition of ice water (100 ml) with cooling of the Lewis acid complex, the organic phase is separated in a separating funnel and the aqueous phase is extracted a further 2 times with $CHCl_3$ (100 ml). The combined extracts are dried over $Na_2SO_4$ sicc. and concentrated to ¼ of the starting volume. The red-brown residue is treated with hexane (20 ml), and the crystallizing product is filtered off with suction and recrystallized from hexane: 4 g (20%) of salmon-coloured substance are obtained.

Mp: 76.5° C. from hexane; Y: 20% (4 g) $C_9H_9ClOS$, MW=200.69; IR (NaCl): $1/\lambda$ $(cm^{-1})$=1687, 1577, 1546, 1394, 1213, 1086, 817; $^1$-NMR($CDCl_3$): δ (ppm)=7.89–7.44 (m, 2H, AA', arom), 7.51–7.26 (m, 2H, BB', arom), 4.66 (s, 2H, $COCH_2Cl$), 2.53 (s, 3H, $SCH_3$).

c) 1-Bromo-2-(4-methylsulphinylphenyl)-2-ethanone

A solution of 2-bromo-1-(4-methylsulphanylphenyl)-1-ethanone (3.7 g, 15 mmol) in $CHCl_3$ (50 ml) is maintained at a temperature of –5° C. A solution of m-chloroperbenzoic acid (70%, 3.7 g, 15 mmol) in $CHCl_3$ (30 ml) cooled to 0° C. is added dropwise while maintaining an IT of –5° C. to 0° C. After stirring for ½ hour in the cold, the deposited m-chlorobenzoic acid is filtered off. The filtrate is first washed with $NaHCO_3$ solution (8% strength, 50 ml) until acid-free and then rewashed with water (50 ml). The $CHCl_3$ phase dried over $Na_2SO_4$ sicc. is concentrated in vacuo. A yellowish residue (1.3 g) results.

Y: 95% (1.3 g) C$_9$H$_9$BrO$_2$S, MW=261.14; IR (NaCl): 1/λ (cm$^{-1}$)=1763, 1706, 1569, 1396, 1290, 1202, 1149, 1103, 997, 956, 826, 758; $^1$H-NMR (CDCl$_3$): δ (ppm)=8.2–8.07 (AA'BB', 4H, arom), 4.71 (s, 2H, CH$_2$Cl), 2.80 (s, 3H, SOCH$_3$).

d) 2-(4-Methylsulphinylphenyl)-1-phenyl-6,7-dihydro-5H-pyrrolizine

2-Benzyl-1-pyrroline (2.0 g, 80% strength, 10 mmol), dissolved in MeOH (30 ml), is treated with a solution of 4-methylsulphinylphenacyl bromide (2.1 g, 8 mmol) in CH$_2$Cl$_2$ (10 ml) and then with NaHCO$_3$ (1.5 g, 18 mmol) and the mixture is stirred at RT until a TLC sample (Al$_2$O$_3$, hexane/ether 9:1) indicates the complete reaction of the bromoketone (Rf 0.75) and an adequate formation of product (Rf=0.2) (48 h). After addition of water (50 ml), the mixture is extracted with diethyl ether (3×30 ml), and the combined extracts are dried over Na$_2$SO$_4$ sicc. and concentrated. The residue is purified by CC (Al$_2$O$_3$, hexane/ether 1:1). 0.3 g (12%) of the compound sought is isolated.

Y: 12% (0.3 g), C$_{20}$H$_{19}$NOS, MW=321.44 IR (NaCl): 1/λ (cm$^{-1}$)=2912, 1586, 1457, 1301, 1140, 1088, 959, 829, 774; $^1$H-NMR (CDCl$_3$): δ (ppm)=7.93–7.64 (4H, arom), 7.53–7.40 (4H, arom), 6.88 (s, 1H), 4.23 (t, CH$_2$), 3.16 (t, CH$_2$), 3.08 (s, CH$_3$), 2.65 (m, CH$_2$).

EXAMPLE 3
2-(4-Methylsulphonylphenyl)-1-phenyl-6,7-dihydro-5H-pyrrolizine a) 2-Bromo-1-(4-methylsulphonylphenyl)-1-ethanone (prepared according to J. Org. Chem. 35, 2106 (1970))

A solution of 1-bromo-2-(4-methylsulphanylphenyl)-2-ethanone (1.25 g, 5 mmol) in CHCl$_3$ (30 ml) is maintained at a temperature of −5° C. A solution of m-chloroperbenzoic acid (3.5 g, 10 mmol) in CHCl$_3$ (30 ml) cooled to 0° C. is added dropwise while maintaining an IT of −5° C. to 0° C. After stirring in the cold for 3 hours, the deposited m-chlorobenzoic acid is filtered off. The filtrate is first washed with NaHCO$_3$ solution (8% strength, 50 ml) until acid-free and then rewashed with water (50 ml). The CHCl$_3$ phase dried over Na$_2$SO$_4$ sicc. is concentrated in vacuo until a reddish-brown solid substance deposits. The solid deposited from the cooled mother liquor (1.3 g) is collected.

Y: 95% (1.3 g) C$_8$H$_8$BrO$_3$S, MW=184.22; Mp: 117.3° C.; IR (NaCl): 1/λ (cm$^{-1}$)=3085, 2935, 1697, 1568, 1335, 1296, 1191, 1145, 1085, 1006, 997, 882, 784, 653; $^1$H-NMR (CDCl$_3$): δ (ppm)=8.20–8.05 (AA'BB', 4H, arom), 4.46 (s, 2H, CH$_2$Br), 3.10 (s, 3H, SO$_2$CH$_3$).

b) 2-(4-Methylsulphonylphenyl)-1-phenyl-6,7-dihydro-5H-pyrrolizine

2-Benzyl-1-pyrroline (2.0 g, 80% strength, 10 mmol), dissolved in MeOH (30 ml), is treated with a solution of 4-methylsulphonylphenacyl bromide (2.3 g, 8 mmol) in CH$_2$Cl$_2$ (10 ml) and then with NaHCO$_3$ (1.5 g, 18 mmol) and the mixture is stirred at RT until a TLC sample (Al$_2$O$_3$, hexane/ether 9:1) indicates the complete reaction of the bromoketone (Rf 0.75) and an adequate formation of product (Rf=0.5) (48 h). After addition of water (50 ml), the mixture is extracted with diethyl ether (3×30 ml), and the combined extracts are dried over Na$_2$SO$_4$ sicc. and concentrated. The residue is purified by CC (Al$_2$O$_3$, hexane/ether 9:1). 0.6 g (25%) of the compound sought is isolated.

Mp: 165, Y 25% (0.6 g), C$_{20}$H$_{19}$NO$_2$S, MW=337.44; IR (NaCl): 1/λ (cm$^{-1}$)=3172, 1590, 1311, 1148, 951, 771, 546

$^1$H-NMR (CDCl$_3$): δ (ppm)=7.80–7.76 u. 7.43–7.38 (AA'BB', 4H, arom), 7.09–6.96 (m, 4H, arom), 4.23–4.12 (q, J=7.1 Hz, 2H), 4.03–3.96 (t, J=7.2 Hz, 2H), 3.27–3.19 (t, J=7.4 Hz, 2H), 3.05 (s, CH$_3$), 2.63–2.49 (quin, J=7.2 Hz, 2H), 1.26–1.19 (t, J=7.0 Hz, CH$_3$).

EXAMPLE 4
2-(4-Methylmercaptophenyl)-1-(4-fluorophenyl)-6,7-dihydro-5H-pyrrolizine a) 2-(4-Fluorobenzyl)-1-pyrroline 4-Fluorotoluene (5.5 g, 0.05 mol), N-bromosuccinimide (NBS, 8.9 g, 0.05 mol) and azaisobutyronitrile (AIBN, 160 mg, 1 mmol) are dispersed in carbon tetrachloride (CCl$_4$, 40 ml); the mixture is stirred at 75° C. for 3–4 h. After cooling, the deposited succinimide is filtered off. The residue is rewashed with CCl$_4$ (10 ml). On concentrating in vacuo, 8.5 g of 4-fluorobenzyl bromide (89%) are obtained from the combined CCl$_4$ phases as a yellow oil.

Magnesium turnings (for Grignard, 6.4 g, 0.266 mol) are covered with a layer of 20 ml of a solution of 4-fluorobenzyl bromide (50 g, 0.265 mol) in abs. (absolute) diethyl ether (250 ml) in a 500 ml three-necked flask and the mixture is briefly heated until the reaction starts. The remaining volume of 4-fluorobenzyl bromide is added dropwise in the course of 30 min and at the same time the mixture is kept at a temperature of 40° C. for a further 2 h in an oil bath. A solution of 4-chlorobutyronitrile (13.6 g, 0.132 mol) in diethyl ether (50 ml) is added dropwise in the course of 30 min to the still warm, freshly prepared Gringnard solution. The largest part of the ether (200 ml) is distilled off over a bridge and replaced by abs. toluene (250 ml). Diethyl ether is driven off until a boiling temperature of 95° C. is achieved in the bottom. The mixture is stirred at this temperature for a further 2 h and then allowed to stand at RT overnight. The organic phase is transferred to a separating funnel and hydrolysed and extracted with 10% strength HCl (3×100 ml each). The toluene phase is discarded, and the HCl-acidic aqueous phase is again washed with toluene (100 ml) and then maintained at pH 10 using conc. NaOH (32% strength). The pyrroline base depositing is taken up with diethyl ether (100 ml) in the separating funnel. After separating the ether phase, the mixture is again extracted with ether (2×50 ml), and the combined ether phases are dried over K$_2$CO$_3$ sicc. and concentrated. 8.8 g of 2-(4-fluorobenzyl)-1-pyrroline (37.8% based on chloronitrile) are obtained.

Bp: 150–153° C., yellow-orange oil, C$_{11}$H$_{12}$FN, MW=177.22; IR (NaCl): 1/λ (cm$^{-1}$)=2957, 2868, 1641, 1603, 1509, 1430, 1222, 1157.5, 837, 825; $^1$H-NMR (CDCl$_3$): δ (ppm)=7.26–6.94 (m, 4H, arom), 3.83 (t, 2H, CH$_2$), 3.64 (s 2H, CH$_2$), 2.39 (t, 2H, CH$_2$), 1.87 (quin 2H, CH$_2$).

b) 1-(4-Fluorophenyl)-2-(4-methylsulphanylphenyl)-6,7-dihydro-5H-pyrrolizine

2-Bromo-1-(4-methylsulphanylphenyl)-1-ethanone (0.83 g, 3.4 mmol), dissolved in diethyl ether (10 ml), is treated with a solution of 2-(4-fluorobenzyl)-1-pyrroline (0.6 g, 3.3 mmol) in ethanol (10 ml) and NaHCO$_3$ (0.6 g, 7 mmol). The mixture is stirred in the dark at RT for 18 h. The reaction is checked by TLC: SiO$_2$/hexane-ether 9:1. The mixture is treated with H$_2$O (10 ml), extracted 2 times with diethyl ether (100 ml) and the combined ether phase is then rewashed with water (30 ml). The organic phase dried over Na$_2$SO$_4$ Sicc. is concentrated in vacuo. The residue which remains is purified by CC on Al$_2$O$_3$/hexane/diethyl ether 1:1. Fractions 1–3 afford 330 mg of orange-red oil.

Y: 33% (330 mg), C$_{20}$H$_{18}$FNS, MW=323.44; $^1$H-NMR (CDCl$_3$): δ (ppm)=7.27–6.89 (2 AA'BB', 8H, 2 arom), 6.74 (s, 1H, CH), 4.04–3.97 (t, 2H, CH$_2$), 2.97–2.90 (tr, 2H, CH$_2$), 2.59–2.48 (m, 2H, CH$_2$), 2.46 (s, 3H, SCH$_3$).

EXAMPLE 5

1-(4-Fluorophenyl)-2-(4-methylsulphonylphenyl)-6,7-dihydro-5H-pyrrolizine

2-Bromo-1-(4-methylsulphonylphenyl)-1-ethanone (2.6 g, 9.5 mmol), dissolved in THF (30 ml) is treated with the solution of 2-(4-fluorobenzyl)-1-pyrroline (1.77 g, 10 mmol) in methanol (50 ml) and NaHCO$_3$ (1.7 g, 20 mmol). The mixture is stirred in the dark at RT for 70 h, water (30 ml) is added and it is stirred for a further 5 h. It is extracted 3 times with diethyl ether (100 ml), and the combined ether phase is then rewashed with water (50 ml) and concentrated in vacuo after drying over Na$_2$SO$_4$ sicc. The residue which remains is purified by CC on Al$_2$O$_3$/ethyl acetate. Fractions 3–4 afford 1.9 g having a melting point of 169.1° C.

Y: 56% (1.9 g), C$_{20}$H$_{18}$FNO$_2$S, MW=355.43; IR (NaCl): 1/λ (cm$^{-1}$)=2924, 1592, 1528, 1502, 1404, 1307, 1215, 1152, 1090, 948, 841, 766; $^1$H-NMR (CDCl$_3$): δ (ppm)= 7.78–7.74/7.39–7.34 (AA'BB', 4H, arom), 7.29–6.92 (m, 4H, arom), 6.85 (s, 1H, CH), 4.09–4.02 (t, 2H, CH$_2$), 3.05 (s, 3H, CH$_3$), 2.97–2.90 (t, 2H, CH$_2$), 2.62–2.49 (quin, 2H, CH$_2$).

EXAMPLE 6

2-(4-Fluorophenyl)-1-(4-methylsulphanylphenyl)-6,7-dihydro-5H-pyrrolizine a) 2-(4-Methylsulphanylbenzyl)-1-pyrroline Sodium hydride (23.9 g, 60% strength in white oil, 0.59 mol) is suspended in abs. THF (150 ml) under nitrogen, and the suspension is heated to reflux. A mixture of ethyl (4-methylsulphanylphenyl)acetate (38 g, 0.18 mol) and 1-vinyl-2-pyrrolidone (20 g, 0.18 mol) in THF abs. (70 ml) is then allowed to run in dropwise via a dropping funnel.

The addition rate is chosen such that the evolution of hydrogen can be kept under control (1.5 h). After complete addition, the reflux (66° C., IT) is maintained for a further 4 h; the mixture is then cooled to RT. The excess of sodium hydride is destroyed by cautious addition of a saturated (37% strength) ammonium chloride solution (150 ml) to the cooled starting solution. The THF phase is separated in a separating funnel, and solid precipitated in the aqueous phase is brought into solution by addition of water and extracted with THF (100 ml). The THF phase is dried with Na$_2$SO$_4$ sicc. and the filtrate is concentrated. The depositing white oil is decanted off. An oily residue of 57 g (115%) having a purity of 80% remains (GC: ethyl 4-methylsulphanylphenylacetate, THF, paraffin) The material obtained is employed in the next step without further purification.

6N HCl (400 ml) is heated to reflux in a 1 l three-necked flask having a water separator. The solution of the crude 3-(4-methylsulphanylphenylacetyl)-1-vinylpyrrolidin-2-one (58 g, 80% strength, 170 mmol) in THF (200 ml) is added dropwise via a dropping funnel to the hot acid, and the volatile acetaldehyde immediately released is distilled from the mixture together with THF via the water separator (time needed 2 h).

The mixture is refluxed for a further 6 h and treated with CHCl$_3$ (200 ml) at RT after cooling in an ice bath. The organic phase is separated in a separating funnel and discarded; the HCl phase is rendered alkaline (pH 11–12) using sodium hydroxide solution (32%, 400 ml) while cooling with crushed ice (0.2 kg). The oil depositing in the course of this is taken up in CHCl$_3$ (100 ml) and the separated aqueous phase is extracted 2 times with CHCl$_3$ (200 ml). The combined CHCl$_3$ solution is washed with water (1 l), dried over Na$_2$SO$_4$ sicc. and the filtrate is concentrated. 22.3 g (64.3%) of 2-(4-methylsulphanylbenzyl)-1-pyrroline of 80% purity (GC) are obtained.

Y: 64.3%=22.3 g (80%), Mp: oily, C$_{12}$H$_{15}$NS, MW=205.32; IR (NaCl): 1/λ (cm$^{-1}$)=3238, 2920, 2866, 1690, 1640, 1493, 1424, 1092; $^1$H-NMR (CDCl$_3$): δ (ppm)= 7.23–7.12 (AA'BB', 4H, arom), 3.9–3.75 (m, 2H, CH$_2$), 3.63 (br, 2H, CH$_2$), 2.465 (s, 3H, SCH$_3$), 2.45–2.35 (m, 2H, CH$_2$), 1.90–1.79 (quin, 2H, CH$_2$).

b) 2-(4-Fluorophenyl)-1-(4-methylsulphanylphenyl)-6,7-dihydro-5H-pyrrolizine 2-(4-Methylsulphanylbenzyl)-1-pyrroline (19.3 g, 80% strength, 0.1 mol), dissolved in MeOH (100 ml), is treated with a suspension of 2-bromo-1-(4-fluorophenyl)-1-ethanone (21.7 g, 0.1 mol) in MeOH (50 ml) and then treated with NaHCO$_3$ (8.4 g, 0.1 mol) and stirred at RT for 72 h (TLC sample (Al$_2$O$_3$, hexane/ether 9:1)).

The solid deposited from the MeOH phase is filtered off, dissolved in acetone, undissolved salts are filtered off and acetone is removed in vacuo. The residue is digested with hot diisopropyl ether and crystallized from this in the cold: 3 g of brown-coloured crystals result.

The MeOH filtrate solution is concentrated and digested with diethyl ether. The crystalline brown bottom material (9 g) obtained is discarded.

The diethyl ether extracts are combined and concentrated. The residue (10 g), a red-brown viscous oil, is purified by CC on SiO$_2$/CHCl$_3$. 3 g (9.3%) of the compound sought are obtained.

Y: 9.3% (3 g); C$_{20}$H$_{18}$FNS, MW=323.44; Mp: oily; IR (NaCl): 1/λ (cm$^{-1}$)=3424, 2918, 1691, 1596, 1493, 1402, 1223, 1156, 1090, 837; $^1$H-NMR (CDCl$_3$): δ (ppm)= 7.23–7.10 (m, 6H, arom), 7.0–6.88 (m, 2H, F-arom), 4.01 (t, 2H, CH$_2$), 2.96 (t, 2H, CH$_2$), 2.522 (quin, 2H, CH$_2$), 2.460 (s, 3H, SCH$_3$); GC-MS: m/e (rel. int.[%])=323 (M$^{+*}$, 100%), 308 ((M-CH$_3$$^*$)$^+$, 10%).

EXAMPLE 7

Methyl 4-[2-(4-fluorophenyl)-6,7-dihydro-5H-pyrrolizin-1-yl]phenylsulphone(synonym 2-(4-fluorophenyl)-1-(4-methanesulphonylphenyl)-6,7-dihydro-5H-pyrrolizine)

a) Methyl 2-(4-fluorophenyl)-1-phenyl-6,7-dihydro-5H-pyrrolizine-3-carboxylate

A solution of 6-(4-fluorophenyl)-7-phenyl-2,3-dihydro-1H-pyrrolizine (prepared according to Laufer et al., 1.11 g, 4 mmol) in CHCl$_3$ (20 ml) is cooled to 0° C. in an ice bath, treated with triethylamine (0.44 g, 4.4 mmol), and diphosgene (0.43 g, 2.2 mmol), dissolved in CHCl$_3$ (5 ml) is added dropwise. After addition is complete, the mixture is stirred at RT for a further 4 h in the cold. After addition of MeOH (4 ml), it is additionally stirred at RT for 16 h. The reaction solution is washed with water, and then with Na$_2$CO$_3$ solution (10%) until acid-free and finally washed again with water. The separated $CHCl_3$ phase is dried using $Na_2SO_4$ sicc. and concentrated. As a residue, 1.3 g (100%) of methyl 2-(4-fluorophenyl)-1-phenyl-6,7-dihydro-5H-pyrrolizine-3-carboxylate are obtained (GC. 93%). The substance is used in the next reaction step without further purification.

Y: 100%=1.3 g (93%), $C_{21}H_{18}FNO_2$, MW=335.38. Mp: 160.0° C. IR (NaCl): $1/\lambda$ $(cm^{-1})$=2997, 2955, 2900, 1701 (ester), 1600, 1550, 1525, 1469, 1401, 1313, 1217, 1121, 1095, 847, 783, 698; $^1$H-NMR ($CDCl_3$): δ (ppm)=7.24–6.95 (m, 9H, arom.); 4.38 (t, 2H, $CH_2$, J=7.2 Hz); 3.64 (s, 3H, $CH_3$,); 3.02 (t, 3H, $CH_2$); 2.54 (quin, 2H, $CH_2$); GC-MS: m/e (rel. int.[%])=335 ($M^{+*}$, 100%), 304 ($(M-OCH_3^*)^+$, 22%), 276 ($(M-COOCH_3^{*})^+$, 22%), 248 (10%).

b) 4-[2-(4-Fluorophenyl)-3-methoxycarbonyl-6,7-dihydro-5H-pyrrolizin-1-yl]benzenesulphonyl chloride Methyl 2-(4-fluorophenyl)-1-phenyl-6,7-dihydro-5H-pyrrolizine-3-carboxylate (1.3 g, 3.8 mmol) is dissolved in dried ($CaCl_2$ sicc.) $CHCl_3$ (10 ml) under nitrogen. Chlorosulphonic acid (2.66 g, 22.8 mmol) in $CHCl_3$ (5 ml) is then allowed to run in dropwise via a dropping funnel. After addition is complete, the mixture is stirred at RT for 16 h.

The starting solution is poured onto ice/water (80 ml) and the deposited $CHCl_3$/oil phase is taken up in further $CHCl_3$ (20 ml). The $CHCl_3$ phase is separated in a separating funnel, and the aqueous phase is saturated with NaCl and again extracted with $CHCl_3$ (30 ml). The collected $CHCl_3$ phase is dried using $Na_2SO_4$ sicc., and the filtrate is concentrated. The product depositing on concentration is filtered off with suction. 1.7 g (106%) remain, which are employed in the next step without further purification.

Y: 106%=1.7 g (85% gc), $C_{21}H_{17}ClFNO_4S$, MW=433.89; IR (NaCl): $1/\lambda$ $(cm^{-1})$=1693, 1587, 1525, 1371, 1225, 1177, 1094, 837, 584, 561; $^1$H-NMR ($CDCl_3$): δ (ppm)=7.83–7.78 (AA', 2H, arom), 7.22–6.97 (m, 6H, BB'+F-arom), 4.428 (t, 2H, J=7 Hz, $CH_2$), 3.657 (s, 3H, $OCH_3$), 3.082 (t, 2H, J=7 Hz, $CH_2$), 2.609 (quin, 2H, J=7 Hz);

c) Methyl 2-(4-fluorophenyl)-1-(4-methylsulphonylphenyl)-6,7dihydro-5H-pyrrolizine-3-carboxylate 4-[2-(4-Fluorophenyl)-3-methoxycarbonyl-6,7-dihydro-5H-pyrrolizin-1-yl]benzenesulphonyl chloride (1.7 g, 3.8 mmol), suspended in water (10 ml), is treated with $Na_2SO_3$ (0.56 g, 4.4 mmol) and then with $Na_2CO_3$ (0.72 g, 6.8 mmol) and stirred at 70° C. for 2 h. The solution is treated with a solution of $CH_3I$ (0.88 g, 6.2 mmol) in ethanol (20 ml) and heated under reflux for 2 h. After cooling, the ethanol is removed in vacuo, the residue is treated with water (25 ml) and the product from the reaction is taken up in ethyl acetate (2×30 ml). The ethyl acetate phase is washed with conc. NaCl solution and water, dried using $Na_2SO_4$ sicc. and the filtrate is concentrated. After removing the solvent in vacuo, 0.4 g (25%) of methyl 2-(4-fluorophenyl)-1-(4-methylsulphonylphenyl)-6,7-dihydro-5H-pyrrolizine-3-carboxylate remains as a residue having a concentration of 77%.

Y: 25%=0.4 g (GC. 77% strength), $C_{22}H_{20}FNO_4S$, MW=413.47; Mp.: 191.0° C. IR (NaCl): $1/\lambda$ $(cm^{-1})$=1716, 1693, 1595, 1527, 1311, 1221, 1150, 1097, 778, 556, $^1$H-NMR ($CDCl_3$): δ (ppm)=7.74–7.69 (AA', 2H, arom), 7.22–6.95 (m, 6H, BB'+F-arom), 4.42 (t, 2H, J=7 Hz, $CH_2$), 3.646 (s, 3H, $OCH_3$), 3.055 (t, 2H, J=7 Hz, $CH_2$), 3.03 (s, 3H, $SO_2CH_3$), 2.594 (quin, 2H, J=7 Hz); GC-MS: m/e (rel. int.[%])=413($M^{+*}$, 100%), 382 ($(M-OCH_3^*)^+$, 14%), 355 (10%), 274(12%).

d) Methyl 4-[2-(4-fluorophenyl)-6,7-dihydro-5H-pyrrolizin-1-yl]phenyl sulphone

Methyl 2-(4-fluorophenyl)-1-(4-methylsulphonylphenyl)-6,7-dihydro-5H-pyrrolizine-3-carboxylate (0.4 g, 0.96 mmol) is heated under reflux for 1 h in methanolic KOH (2 N, 9 ml, 1.01 g of KOH, 18 mmol). After cooling, water (20 ml) is added and the alkaline phase is rendered weakly acidic (pH 3) using HCl (conc. 25%). The deposited substance is extracted with ethyl acetate, and the ethyl acetate extract is dried using $Na_2SO_4$ sicc. and concentrated after filtering. After the removal of the solvent in vacuo, 0.4 g (75% GC) of residue remains. The CC purification is carried out on $SiO_2$ using ethyl acetate as an eluent. The main fractions are concentrated in vacuo and the residue is recrystallized from diisopropyl ether:

Y: 17%=0.06 g (gc 95%), $C_{20}H_{18}FNO_2S$, MW=355.43; IR (NaCl): $1/\lambda$ $(cm^{-1})$=2924, 1593, 1535, 1308, 1219, 1149, 954, 839, 776, 554, 537; $^1$H-NMR ($CDCl_3$/DMSO-d6): δ (ppm)=7.78–7.74 (AA'.2H, $SO_2CH_3$.arom-7); 7.34–6.9 (m, BB', 2H, $SO_2CH_3$ arom-7, +m, 4H, F-arom), 6.73 (s, 1H, pyrroliz.); 4.045 (t, 2H, $CH_2$, J=7.1); 3.087–2.95 (m, 5H, $CH_2$, $CH_3$,); 2.60 (quin., 2H, $CH_2$); GC-MS: m/e (rel. int.[%])=355 ($M^{+*}$, 100%), 276, 248, 220.

EXAMPLE 8
2-(4-Fluorophenyl)-1-(4-methanesulphonylphenyl)-3-methyl-6,7-dihydro-5H-pyrrolizine a) 6-(4-Fluorophenyl)-7-phenyl-2,3-dihydro-1H-pyrrolizine According to the procedure of Laufer et al. (J. Med. Chem. 1994, 37, 1894–1897), first 2-bromo-1-(4-fluorophenyl)ethanone (10.8 g, 0.05 mol) in portions and then $NaHCO_3$ (5.0 g, 0.06 mol) are added to a solution of 2-benzylpyrroline (Example 1a, 15 g, 80%, 0.075 mol) in ethanol (150 ml) in a round-bottomed flask. The reaction mixture is stirred for 24–60 h with exclusion of light; during this time the temperature of the solution is kept between 30–40° C.

The crystals depositing are filtered off, washed a number of times with cold EtOH and dried. 11 g of crude product are obtained, which still contains inorganic salts.

Y: <79%, NaBr, $NaHCO_3$, $C_{19}H_{16}FN$, MW=277.34; IR (NaCl): $1/\lambda$ $(cm^{-1})$=3447, 3040, 2949, 2888, 1596, 1534, 1496, 1396, 1213, 1155, 839, 766, 701; $^1$H-NMR ($CDCl_3$): δ (ppm)=7.26–7.13 (m, 9Harom), 6,74 (s,1H, CH=C), 4.05–3.98 (t, 2H, $CH_2$), 3.01–2.93 (t, 2H, $CH_2$), 2.56–2.49 (quin, 2H, $CH_2$); $^{13}$C-NMR ($CDCl_3$): δ (ppm)=161.18 (d, C—F, J=242 Hz), 136.19 (d, J=2.0 Hz), 132.63 (d, J=3.2 Hz), 129.73 (d, J=7.7 Hz), 128.52, 128.11, 126.34, 124.946, 114.88 (d, J=21.0 Hz), 113.74, 112.96 (pyrrole-C—H), 46.48, 27.34, 24.51.

b) 2-[2-(4-Fluorophenyl)-1-phenyl-6,7-dihydro-5H-pyrrolizin-3-yl]acetic acid

Laufer et al. (J. Med. Chem. 1994, 37, 1894–1897)

Oxalyl dichloride (11.4 g, 0.09 mol) is added dropwise to an ice-cold solution of 6-(4-fluorophenyl)-7-phenyl-2,3-dihydro-1H-pyrrolizine (see above 16.6 g, 0.06 mol) in THF (100 ml) at 0–10° C. After addition is complete, the mixture is stirred for a further hour and ice water (30 ml) is then cautiously added dropwise, which leads to strong evolution of gas and to the foaming of the mixture. The gases (HCl, CO, $CO_2$) are led through an absorber. Hydrazine (36.5 ml, 37.5 g, 0.6 mol) is added dropwise and diethylene glycol (72 ml) is poured in.

The reaction mixture is heated to 100° C.; THF and water pass over under atmospheric pressure in a distillation bridge. After increasing the temperature in the bottom to 105° C., foaming commences. The mixture is cooled and potassium hydroxide solution (50% in water (44 g), 62.8 g of KOH 85%, 1.32 mol) is added at 30–40° C. in 5 portions and the temperature is increased in steps. At 50–60° C., the evolution of gas ($N_2$) again commences (take care, strong foaming). At 135° C. (IT), water and residual solvents pass over ($H_2O$). This temperature is maintained in the bottom for approximately 2 h, then the evolution of gas subsides and the colour of the mixture lightens. If the mixture has reached a pale beige coloration, the batch is poured onto ice. The reaction mixture is acidified to pH 2–3 using HCl 10% strength (175 g, 150 ml of HCl 32%, water 300 ml), while the temperature is kept below 10° C. by cooling with ice in order to suppress the decomposition of the product.

The product, which deposits from the acidic solution in the form of fine crystals, is filtered off and washed with water (pH of the wash solutions>5.0).

If the product deposits oil, it is extracted with ethyl acetate (3×100 ml), dried using $Na_2SO_4$ sicc., and the filtrate is concentrated. 13 g (65%) of oily residue are obtained, which crystallizes from diisopropyl ether.

Y: 65%=13 g (2%), $C_{21}H_{18}FNO_2$, MW=335.38; IR (NaCl): $1/\lambda$ $(cm^{-1})$=3436, 1721, 1600, 1530, 1501, 1393, 1222, 1181, 1156, 839, 699; $^1$H-NMR ($CDCl_3$): δ (ppm)= 7.25–6.93 (m, 9H, arom), 4.06–3.99 (t, 2H, —$CH_2$), 3.61 (s, 3H, —$CH_3$), 3.08–3.01 (t, 2H, —$CH_2$), 2.59–2.52 (quin, 2H, —$CH_2$).

c) 6-(4-Fluoropbenyl)-5-methyl-7-phenyl-2,3-dihydro-1H-pyrrolizine

A flask filled with crystalline solid substance of 2-[2-(4-fluorophenyl)-1-phenyl-6,7-dihydro-5H-pyrrolizin-3-yl]-2-acetic acid (61 g, 0.182 mol) is heated to 180° C. in an oil bath. The decarboxylation via the release of $CO_2$ gas is checked by means of a gas bubble counter; it is complete after 10–15 min. The bath is removed, the contents are cooled to 50° C. and diisopropyl ether (100 ml) is added. The suspension is stirred until it has cooled to room temperature, then the crystals are filtered off with suction and the product is crystallized again from diisopropyl ether if required.

46 g (86.7%) of crystalline compound are obtained.

Y: 86.7%=46 g (2%), $C_{20}H_{18}FN$, MW=291.37; IR (NaCl): $1/\lambda$ $(cm^{-1})$=2880, 1599, 1538, 1500, 1218, 829, 700; $^1$H-NMR ($CDCl_3$): δ (ppm)=7.25–6.90 (m, 9H, arom), 3.94 (t, 2H, J=7.0 Hz, $CH_2$), 3.036 (t, 2H, J=7.0 Hz, $CH_2$), 2.54 (quin, 2H, J=7.0 Hz, $CH_2$), 2.227 (s, 3H, $CH_3$).

d) 2-(4-Fluorophenyl)-1-(4-methanesulphonylphenyl)-3-methyl-6,7-dihydro-5H-pyrrolizine Chlorosulphonic acid (7 g, 60 mmol) is added dropwise to a solution of 6-(4-fluorophenyl)-5-methyl-7-phenyl-2,3-dihydro-1H-pyrrolizine (2.91 g, 10 mmol) in $CHCl_3$ (12 ml) cooled to 0° C. with further cooling and the mixture is heated under reflux (66° C.) for 3 h after addition is complete. The reaction mixture is then poured onto ice water (0.4 kg) and the sulphonyl chloride depositing is taken up in chloroform (150 ml). The ice-water phase is extracted with chloroform (100 ml). These $CHCl_3$ extracts are dried using $Na_2SO_4$ sicc. and concentrated. The residue is treated with an aqueous solution (25 ml) of $Na_2SO_3$ (1.42 g, 11.2 mmol) and $NaHCO_3$ (1.89 g, 22.5 mmol) and heated at 70° C. (IT) for 2 h. After addition of ethanol (25 ml) and methyl iodide (1.0 ml, 2.27 g, 16 mmol), the temperature is increased to 100° C. (IT) and maintained for a further 2 h (reflux). After the cooling of the mixture, deposited solid is filtered off with suction, washed with water (10 ml) and dried over $P_2O_5$ in vacuo: 0.4 g (11%) of the product having a melting point of 191° C. (97% purity) results. The aqueous-ethanolic phase is extracted with ethyl acetate (50 ml) and the filtrate is concentrated after drying with $Na_2SO_4$ sicc. The residue crystallizes from EtOH (5 ml): 0.5 g (14% of theory, 94% purity) results.

Y: 25%=0.9 g, $C_{21}H_{20}FNO_2S$, MW=369.46; Mp: 190–192° C.; IR (NaCl): $1/\lambda$ $(cm^{-1})$=3440, 2975, 2925, 1591, 1533, 1500, 1302, 1215, 1152, 844, 772; $^1$H-NMR ($CDCl_3$): δ (ppm)=7.72–7.68 (AA', 2H, arom), 7.25–7.00 (m, 6H, arom), 3.97 (t, 2H, $CH_2$), 3.07 (t, 2H, $CH_2$), 3.00 (s, 3H, $SO_2CH_3$,), 2.65–2.5 (quin, 2H, $CH_2$), 2.02 (s, 3H, $CH_3$).

EXAMPLE 9

2-(4-Fluorophenyl)-3-(4-methanesulphanylphenyl)-1-methyl-6,7-dihydro-5H-pyrrolizine a) 2-Ethyl-1-pyrroline (analogously to Example 1, steps a and b)

Sodium hydride (60% in paraffin, 36 g, 0.9 mol) is suspended in abs. THF (180 ml) in a 1 l three-necked flask having a dropping funnel and reflux condenser, and the suspension is heated under gentle reflux for 10 min. A mixture of ethyl propionate (33.7 g, 0.33 mol) and 1-vinyl-2-pyrrolidone (33.34 g, 0.3 mol) in abs. THF (35 ml) is added dropwise to the boiling suspension (10 min) and kept under reflux for 3.5 h by heating with stirring.

After cooling to 10° C. (ice bath), the excess of sodium hydride is destroyed (beware! $H_2$) and neutralized using saturated ammonium chloride solution (300 ml), and to drive off the liberated ammonia the mixture which is now 30° C. is intensively stirred for a further 10 min. The deposited THF phase is separated, dried over $Na_2SO_4$ sicc. and concentrated. The paraffin layer depositing on the oil phase is decanted. The red oily product fraction obtained (3-propionyl-1-vinyl-2-pyrrolidone, 51.2 g, 102% of theory) is used without further purification for the preparation of 2-ethyl-1-pyrroline:

Y: 102%=51.2 g (about 92%), $C_9H_{13}NO_2$, MW=167.21; Bp: 140.20° C. (760 Torr); IR (NaCl): $1/\lambda$ $(cm^{-1})$=2955, 2925, 2854, 698, 1633, 1456, 1427, 1387, 1327, 1273, 1114, 979; $^1$H-NMR ($CDCl_3$): δ (ppm)=7.08–6.95 (CH), 4.52–4.42 ($CH_2$), 3.74–3.67 (CH), 3.60–3.41 ($CH_2$), 3.13–2.96 (CH), 2.69–2.51 ($CH_2$), 2.23–2.09 (CH), 1.12–1.04 (t, $CH_3$); $^{13}$C-NMR ($CDCl_3$): δ (ppm)=205.3 (C=O), 168.4 (C=O), 129.1 (C—H), 95.6 ($CH_2$), 55.2 (C—H), 43.1 ($CH_2$), 35.9 ($CH_2$), 19.3 ($CH_2$), 7.3 ($CH_3$).

HCl (20%, 300 ml) is heated to gentle boiling in a 113-necked flask having a dropping funnel as well as a water separator having a reflux condenser. A solution of the crude 3-propionyl-1-vinyl-2-pyrrolidone (40.4 g, 240 mmol) in THF (60 ml) is added dropwise (10 min) from the dropping funnel, and the starting mixture is kept at 100° C. (IT). The acetaldehyde/THF mixture (47 ml) collected in the water separator is discarded. The mixture is kept at this temperature for 6 h, cooled and extracted with ether (200 ml). The 2-ethyl-1-pyrroline is deposited in the cold (5–10° C.) from the HCl-acidic aqueous phase by rendering alkaline to pH 9–10. The deposited oil is taken up in diethyl ether (150 ml), and the aqueous phase is extracted with diethyl ether (300 ml). The ether phases are combined, dried ($K_2CO_3$) and concentrated in a weak vacuum (240 mmHg, 45° C.). 18.4 g (79%) of ethyl-1-pyrroline are obtained as a yellow-coloured oil.

Y: 79%=18.4 g (about 94%), $C_6H_{11}N$, MW=97.16; Bp: 109.5 (760 mmHg); IR (NaCl): $1/\lambda$ ($cm^{-1}$)=3378, 2969, 2937, 2870, 1644, 1462, 1454, 1431, 1371, 1300, 1144, 1093, 1019, 961; $^1$H-NMR ($CDCl_3$): δ (ppm)=3.38–3.76 (m, $CH_2$), 2.52–2.34 (m, 2 $CH_2$), 1.95–1.83 (quin, $CH_2$, J=7.8 Hz), 1.19–1.12 (t, $CH_3$, J=7.6 Hz); $^{13}$C-NMR ($CDCl_3$): δ (ppm)=179.8, 60.5, 36.9, 26.8, 22.4, 10.6.

b) 6-(4-Fluorophenyl)-7-methyl-2,3-dihydro-1H-pyrrolizine

2-Bromo-1-(4-fluorophenyl)-1-ethanone (19.53 g, 90 mmol) is added dropwise to the oily ethyl-1-pyrroline (17.55 g, 180 mmol) in portions in a 500 ml flask, the exothermically reacting mixture being cooled between the additions. The mixture of the reaction components is heated in an oil bath (100° C.) with stirring (30 min). The course of the reaction is monitored by TLC.

The cooled mixture is treated with $CH_2Cl_2$ (250 ml), and deposited salts are washed out in the separating funnel using two portions of HCl (3%, 40 ml). The $CH_2Cl_2$ phase is washed with water (50 ml), dried ($Na_2SO_4$ sicc.) and concentrated.

As a residue, 14.04 g (72% of theory) of 6-(4-fluorophenyl)-7-methyl-2,3-dihydro-1H-pyrrolizine remain as a brown viscous oil.

Y: 72%=14.04 g (about 90%), $C_{14}H_{14}FN$, MW=215.27; IR (NaCl): $1/\lambda$ ($cm^{-1}$)=2958, 1703, 1601, 1509, 1223, 1158, 839, 755; $^1$H-NMR ($CDCl_3$): δ (ppm) 7.39–7.30 (m, 2H, F-arom), 7.08–6.98 (m, 2H, F-arom), 6.67 (s, 1H, 5-H), 3.954 (t, 2H, $CH_2$, J=7 Hz), 2.801 (t, 2H, $CH_2$, J=7 Hz), 2.487 (quin, $CH_2$, J=7 Hz), 2.125 (s, 3H, $CH_3$); $^{13}$C-NMR ($CDCl_3$): δ (ppm)=161.04 (d, C—F, J=242 Hz), 135.58 (d, J=2.0 Hz), 133.51 (d, J=2 Hz), 128.87 (d, J=7.5 Hz), 127.65, 115.025 (d, J=20.9 Hz), 111.11 (pyrrole-C—H), 106.71, 46.47, 27.44, 23.14, 10.86; GC-MS: m/e (rel. int.[%])=216 (14), 215 ($M^{+•}$, 100%), 214 (99), 201 (7), 200 (40), 199 (7), 198 (10), 172 (10) 146 (10).

c) 5-Bromo-6-(4-fluorophenyl)-7-methyl-2,3-dihydro-1H-pyrrolizine

The solution of 6-(4-fluorophenyl)-7-methyl-2,3-dihydro-1H-pyrrolizine (9.0 g, 42 mmol) in abs. THF (50 ml) is cooled to −15° C. N-Bromosuccinimide (3.46 g, 19.4 mmol) is added in portions; the mixture is stirred until no more starting material is detectable (TLC $SiO_2$, diisopropyl ether-hexane 2:1). The black-purple-coloured reaction mixture is chromatographed on a column (20 cm×3 cm) packed with $Al_2O_3$ (ICI, for dry packing). The column is subsequently washed with n-hexane (80 ml), and the filtrates are concentrated. 3.55 g (28.9%) of a black-brown oil are obtained, which rapidly decomposes.

Y: 28.9%=3.55 g (about 90%), $C_{14}H_{14}FN$, MW=215.27; $^1$H-NMR ($CDCl_3$): δ (ppm)=7.37–7.29 (m, 2H, F-arom), 7.15–7.00 (m, 2H, F-arom), 3.923 (t, 2H, $CH_2$, J=7 Hz), 2.861 (t, 2H, $CH_2$, J=7 Hz), 2.482 (quin, $CH_2$, J=7 Hz), 2.006 (s, 3H, $CH_3$).

d) 2-(4-Fluorophenyl)-3-(4-methanesulphanylphenyl)-1-methyl-6,7-dihydro-5H-pyrrolizine
(according to Suzuki et al., J. Heterocyclic Chem. 31, 1637 (1994))

5-Bromo-6-(4-fluorophenyl)-7-methyl-2,3-dihydro-1H-pyrrolizine (2.66 g, 8.83 mmol) and tetrakis-(triphenylphosphine)palladium (330 mg, 0.29 mmol, 1:30) are dispersed in toluene (12 ml), the solution of 4-methylthiophenylboronic acid (1.0 g, 6 mmol) in EtOH (7.5 ml) is added and $Na_2CO_3$ solution (12 ml, 2 M, 2.8 g) is finally added. The mixture of the components is immersed in an oil bath maintained at 100° C. and refluxed until the disappearance of the bromo compound (16 h). The black-coloured mixture is treated with saturated NaCl solution (50 ml) and $CH_2Cl_2$ (80 ml). The organic phase is separated and concentrated in vacuo, and the residue is purified by CC ($Al_2O_3$, diisopropyl ether, n-hexane 1:3). The residue obtained from fractions 7–18 is crystallized from n-hexane: 0.58 g (28%) of 2-(4-fluorophenyl)-3-(4-methanesulphanylphenyl)-1-methyl-6,7-dihydro-5H-pyrrolizine having a melting point of 113.7° C.

Y: 28%=0.58 g, $C_{21}H_{20}FNS$, MW=337.46; IR (NaCl): $1/\lambda$ ($cm^{-1}$)=2985, 2918, 2842, (1596) 1524, 1504, 1479, 1424, 1404, 1367, 1305, 1215, 830, 805; $^1$H-NMR ($CDCl_3$): δ (ppm)=7.2–6.9 (8H, m, arom), 4.0 (2H, t, J=6.9 Hz), 2.88 (2H, t, J=7.3 Hz), 2.501 (2H, quin, $CH_2$), 2.45 (3H, s, $CH_3$), 2.03 (3H, s, $CH_3$); $^{13}$C-NMR ($CDCl_3$): δ (ppm)=161.1 (d, C—F, J=240 Hz), 137.52, 135.76, 132.59 (d, J=3.2 Hz), 131.60 (d, J=4 Hz, CH), 129.83, 129.06 (CH), 126.32 (CH), 124.87, 114.94 (d, J=21 Hz, CH), 108.50 (C-5), 46.32 ($CH_2$), 27.26 ($CH_2$), 23.29 ($CH_2$), 15.69 (S$\underline{C}H_3$), 10.23 (7-$\underline{C}H_3$). GC-MS (70 eV): m/z (rel. int. [%])=339 (5), 338 (27), 337 (100, M+.), 336 (25), 322 (40), 290 (10).

e) 2-(4-Fluorophenyl)-3-(4-methanesulphinylphenyl)-1-methyl-6,7-dihydro-5H-pyrrolizine
CC ($SiO_2$, EA/n-hexane 4:1):
Fraction 1–2:
2-(4-Fluorophenyl)-3-(4-methanesulphonylphenyl)-1-methyl-6,7-dihydro-5H-pyrrolizine
Fraction 3–5
2-(4-Fluorophenyl)-3-(4-methanesulphinylphenyl)-1-methyl-6,7-dihydro-5H-pyrrolizine
$^1$H-NMR ($CDCl_3$): δ (ppm)=7.52–7.47 (AA', 2H, Ar.), 7.29–7.24 (BB', 2H, Ar.), 7.16–7.10 (m, 2H, F-arom), 7.09–6.92 (m, 2H, F-arom), 4.04 (2H, t, J=6.9 Hz), 2.89 (2H, t, J=7.3 Hz), 2.73 (s, 3H, $SOCH_3$), 2.53 (2H, quin, $CH_2$), 2.02 (3H, s, $CH_3$).

f) 2-(4-Fluorophenyl)-3-(4-methanesulphonylphenyl)-1-methyl-6,7-dihydro-5H-pyrrolizine
CC ($SiO_2$, EA/n-hexane 4:1):
$^1$H-NMR ($CDCl_3$): δ (ppm)=7.77–7.72 (AA', 2H, Ar.), 7.29–7.24 (BB', 2H, Ar.), 7.16–7.10 (m, 2H, F-arom), 7.09–6.92 (m, 2H, F-arom), 4.06 (2H, t, J=6.9 Hz), 3.05 (s, 3H, $SO_2CH_3$), 2.90 (2H, t, J=7.3 Hz), 2.54 (2H, quin, $CH_2$), 2.01 (3H, s, $CH_3$).

EXAMPLE 10

4-[3-(4-Fluorophenyl)-6,7-dihydro-5H-pyrrolizin-2-yl]benzenesulphonamide a) 1-(4-Fluorobenzoyl)pyrrolidine-2-carboxylic acid L-Proline (2.5 g, 22 mmol) is dissolved in NaOH (5%, 25 ml, 31 mmol) and, after cooling, treated dropwise, with vigorous stirring, with 4-fluorobenzoyl chloride (3.17 g, 20 mmol). The resulting suspension is again treated with NaOH (5%, 15 ml, 19 mmol) and stirred at RT for 1 h. HCl (20% strength, 10 ml) is added with ice cooling and the mixture is stirred until formation of a crystallizate which can be filtered off with suction. The crystallizate subsequently filtered off with suction is washed with water until HCl-free and dried over $P_2O_5$ in a desiccator. 4.21 g (88.8% of theory) of crystallizate remain after drying.

Y: 89% (4.21 g), $C_{12}H_{12}FNO_3$, MW=237.23; Mp: 174.0° C.; IR (NaCl): $1/\lambda$ ($cm^{-1}$)=1735, 1605, 1585, 1514, 1440, 1230, 1180, 1161, 856, 762, 513; $^1$H-NMR (CDCl$_3$): δ (ppm)=7.64–7.61 (d, 2H, J=5.4 Hz), 7.59–7.57 (d, 2H, J=5.4 Hz), 7.16–7.07 (t, 2H, J=8.6 Hz).

b) Methyl 3-(4-fluorophenyl)-2-phenyl-6,7-dihydro-5H-pyrrolizine-1-carboxylate

Methyl phenylpropiolate (methyl dehydrocinnamate (0.96 g, 6 mmol)) is dissolved in acetic anhydride (14 ml) and brought to the boiling temperature of acetic anhydride in a hot oil bath (140° C.). The total amount of 1-(4-fluorobenzoyl)pyrrolidine-2-carboxylic acid (1.42 g, 6 mmol) is added, and the thoroughly mixed solution is refluxed (1 28° C.) for 20 h with stirring. After standing for 4 hours and cooling to RT, a pure crystalline solid deposits (TLC: $Al_2O_3$, diisopropyl ether, Rf 0.7). The crystals are filtered off with suction, washed with water (20 ml) and finally with isopropyl ether (10 ml). The dried crystals weigh 650 mg (32.5% of theory)

Y: 89% (4.21 g), $C_{21}H_{18}FNO_2$, MW=335.38; IR (NaCl): $1/\lambda$ ($cm^{-1}$)=2497, 1791, 1493, 1428, 1157, 846; $^1$H-NMR (CDCl$_3$): δ (ppm)=7.50–7.37 (m, 6H), 7.17–7.01 (r, 2H, F-arom), 3.93–3.86 (t, 2H), 3.53 (s, CH$_3$), 3.01–2.94 (t, 2H), 2.55–2.41 (m, 2H).

c) 4-[3-(4-Fluorophenyl)-6,7-dihydro-5H-pyrrolizin-2-yl] benzenesulphonamide

In a dried flask which has been flushed with argon and cooled to −15° C. in a cooling bath with exclusion of moisture, chlorosulphonic acid (2.6 ml, 4.537 g, 39 mmol) is treated in 2 portions with ethyl 3-(4-fluorophenyl)-2-phenyl-6,7-dihydro-5H-pyrrolizine-1-carboxylate (436 mg, 1.3 mmol). The mixture is stirred for 16 h, the cooling is removed and it is warmed to RT. The reaction is monitored by TLC (SiO$_2$/isopropyl ether-EA 1:1, starting material Rf 0.8, sulphochloride Rf 0.7). Excess chlorosulphonic acid and resultant $H_2SO_4$ are quenched after cooling to −15 to −20° C. by dropwise addition of water (20 ml) and the sulphuric acid aqueous phase is extracted with ethyl acetate (60 ml). The combined, dried (Na$_2$SO$_4$ sicc.) EA phases are saturated with NH$_3$ in a cooling bath (−15° C.) (10 min) and subsequently stirred at RT for a further 2 h (TLC checking: SiO$_2$/isopropyl ether-EA 1:1, starting material Rf 0.8, sulphochloride Rf 0.7, sulphonamide Rf 0.0; RP 18/acetone—H$_2$O 7:3, starting material Rf 0.2, sulphochloride Rf 0.1, sulphonamide Rf 0.4). The semi-solid residue depositing is digested with MeOH (10 ml), the insoluble ammonium salts are filtered off and the clear solution is concentrated in vacuo. The residue obtained (0.55 g) is digested with ether, and the solid substance obtained from ether in vacuo is recrystallized from ethanol: 0.45 g (97% of theory) remains.

Y: 89% (4.21 g), $C_{19}H_{17}FN_2O_2S$, MW=356.42; Mp: 206.9° C.; IR (NaCl): $1/\lambda$ ($cm^{-1}$)=3355, 3048, 1596, 1403, 1321, 1151; $^1$H-NMR (CD$_3$OD): δ (ppm)=7.58–7.81 (d, 1H, J=8.4 Hz), 7.66–7.62 (d, 1H, J=8.5 Hz), 7.59–7.56 (d, 1H, J=5.3 Hz), 7.54–7.52 (d, 1H, J=5.3 Hz), 7.16–7.07 (t, 2H, J=8.8 Hz), 6.74 (s, 1H), 4.19–4.12 (t, 2H, J=7.1 Hz), 3.18–3.10 (t, 2H, J=7.2 Hz), 2.68–2.55 (m, 2H); $^{13}$C-NMR (CD$_3$OD): δ (ppm)=163.4, 158.6, 139.7, 138.4, 136.7, 128.7, 128.5, 127.1, 127.0, 126.2, 124.2, 115.4, 115.0, 114.2, 108.0, 46.1, 27.3, 25.2.

EXAMPLE 11

Ethyl 3-(4-fluorophenyl)-2-(4-methylsulphanylphenyl)-6,7-dihydro-5H-pyrrolizine-1-carboxylate a) Ethyl 2-bromo-3-(4-methylsulphanylphenyl)acrylate 4-Methylsulphanylbenzaldehyde (1.52 g, 10 mmol), dissolved in toluene (8 ml), is rapidly added dropwise to a solution of bromoethoxycarbonyltriphenylphosphoranylidene (4.48 g, 10.5 mmol) in toluene (30 ml) with exclusion of light (aluminium foil wrapping). The mixture is stirred overnight at RT (16 h, TLC checking: SiO$_2$/ether-hexane 1:1). Toluene is removed in vacuo, the residue is digested with diethyl ether (50 ml), and the residual crystal precipitate (triphenylphosphine oxide) is washed 2 times with ether (15 ml). The ether filtrates are concentrated in vacuo and the crude product (5.7 g) is purified by column chromatography (SiO$_2$/ether-hexane 7:3): 2.72 g result.

Y: 90%, $C_{12}H_{13}BrO_2S$ MW=301.20; $^1$H-NMR (CDCl$_3$): δ (ppm)=8.16 (s, 1H), 7.85–7.80 u; 7.28–7.24 (AA'BB', 4H, arom), 4.404.29 (q, J=7.1 Hz, 2H), 2.51 (s, CH$_3$), 1.42–1.35 (t, J=7.1 Hz, CH$_3$).

b) Ethyl 3-(4-fluorophenyl)-2-(4-methylsulphanylphenyl)-6,7-dihydro-5H-pyrrolizine-1-carboxylate A solution of ethyl 2-bromo-3-(4-methylsulphanylphenyl)acrylate (0.75 g, 3 mmol) in acetic anhydride (7 ml) is treated with N4-fluorobenzoylproline (0.59 g, 2.5 mmol), and the reaction vessel is immersed in an oil bath maintained at 150° C. The mixture is refluxed for 18 h with stirring; it is then allowed to cool. After about 48 h, the starting solution is treated with ice water and the acetic acid aqueous phase is extracted with ethyl acetate. The ethyl acetate phase washed with water is dried with Na$_2$SO$_4$ sicc. and concentrated in a rotary evaporator. The residue obtained (1.0 g) is purified by CC (SiO$_2$/ether-hexane 1:1): two products are isolated: fractions 11–13 (Rf 0.5) afford 20 mg, fractions 15–25 (Rf 0.3) 15 mg. ⅔ (0.49 g) of the ethyl 2-bromo-3-(4-methylsulphanylphenyl)acrylate used is recovered in fractions 6–8.

Product A:

Ethyl 3-(4-fluorophenyl)-2-(4-methylsulphanylphenyl)-6,7-dihydro-5H-pyrrolizine-1-carboxylate Y: 20 Mg, $C_{23}H_{22}FNO_2S$, MW=395.50; $^1$H-NMR (CDCl$_3$): δ (ppm)=: 8.01–7.94 u. 6.98–6.89 (m, 4H, arom), 7.13 (s, 5H), 4.17–4.08 (q u. t, 4H), 4.02–3.95 (t, J=7.1 Hz, 2H), 3.25–3.17 (t, J=7.5 Hz, 2H), 2.61–2.47 (quin, J=7.4 Hz, 2H), 2.31 (s, CH$_3$), 1.24–1.16 (t, J=7.2 Hz, CH$_3$).

Product B:

Ethyl 3-(4-fluorophenyl)-1-(4-methylsulphanylphenyl)-6,7-dihydro-5H-pyrrolizine-2-carboxylate Y: 15 mg, $C_{23}H_{22}FNO_2S$, MW=395.50;

EXAMPLE 12

Ethyl 3-(4-fluorophenyl)-2-(4-methylsulphonylphenyl)-6,7-dihydro-5H-pyrrolizine-1-carboxylate a) 4-Methylsulphonylbenzaldehyde A solution of 4-methylmercaptobenzaldehyde (6.08 g, 40 mmol) in CH$_2$Cl$_2$ (40 ml) is cooled to 5° C. in an ice bath.

A solution of m-chloroperbenzoic acid (mCPBA, 19.72 g, 70% strength, 80 mmol) in CHCl$_3$ (220 ml) is added dropwise, the reaction temperature being kept below 10° C. (1 h). The mixture is stirred for 4 h in an ice bath. The crystallized m-chlorobenzoic acid (14 g) is filtered off with suction. The filtrate is first washed with NaHCO$_3$ solution (8% strength, 50 ml) until acid-free (m-chlorobenzoic acid 5 g) and then rewashed with water (100 ml). The CHCl$_3$ phase dried over Na$_2$SO$_4$ sicc. is concentrated in vacuo until a white solid substance deposits. The solid deposited from the cooled mother liquor is collected (5.26 g).

Y: 75% (5.26 g), C$_8$H$_8$O$_3$S, MW=184.22; Mp: 160.5–162.1° C.; IR (NaCl): 1/λ (cm$^{-1}$)=3000, 2925, 1702, 1294, 1148, 961, 766, 529; $^1$H-NMR (CDCl$_3$): δ (ppm)= 10.15 (s, CHO), 8.17–8.13 u. 8.11–8.07 (AA'BB', 4H, arom), 3.11 (s, CH$_3$);

$^{13}$C-NMR (CDCl$_3$): δ (ppm)=190.6, 145.3, 139.6, 130.3, 128.2, 44.3.

b) Ethyl 2-bromo-3-(4-methylsulphonylphenyl)acrylate

The suspension of 4-methylsulphonylbenzaldehyde (3.68 g, 20 mmol) in toluene (30 ml) is added with the exclusion of light to a solution of bromoethoxycarbonyltriphenylphosphoranylidene (8.55 g, 20 mmol) in toluene (60 ml). The mixture is first stirred overnight at RT (16 h, TLC checking: SiO$_2$/ether-hexane 1:1), then heated at 60° C. for 6 h and, after addition of bromoethoxycarbonyltriphenylphosphoranylidene (2.0 g, 5 mmol), stirred for a further 24 h, this is repeated again (2.0 g, 5 mmol) and the mixture is finally worked up after a further 24 h. Toluene is removed in vacuo, the residue is digested with diethyl ether (40 ml), and the remaining crystal precipitate (triphenylphosphine oxide) is suspended 2 times with ether (10 ml) and filtered off with suction. The ether filtrates are concentrated in vacuo, and the crude product is crystallized from diisopropyl ether (5 ml): 2.3 g of white solid substance result which, however, contain 4-methylsulphonylbenzaldehyde (25%).

Y: 25.9% (2.3 g, 75% strength), C$_{12}$H$_{13}$BrO$_4$S, MW=333.20; $^1$H-NMR (CDCl$_3$): δ (ppm)=8.24 (s, 1H), 7.99 (s, 5H), 4.44–4.33 (q, J=7.1 Hz, 2H), 3.09 (s, CH$_3$), 1.44–1.37 (t, J=7.1 Hz, CH$_3$).

or: Ethyl 2-bromo-3-(4-methylsulphanylphenyl)acrylate (Example 11a, 0.9 g, 3 mmol) is dissolved in CHCl$_3$, and the solution is cooled to 5° C. and then treated dropwise with a CHCl$_3$ solution (20 ml) of mCPBA (1.65 g, 70%, 6.6 mmol). The mixture is stirred for 3 h in the cold and then for 16 h at RT, then the deposited solid is filtered off with suction and washed with CHCl$_3$ (20 ml). The CHCl$_3$ filtrates are first washed with NaHCO$_3$ solution (8% strength, 50 ml) until acid-free (m-chlorobenzoic acid 5 g) and then rewashed with water (100 ml). The CHCl$_3$ phase dried over Na$_2$SO$_4$ sicc. is completely concentrated in vacuo: a white solid substance of 1.03 g (103%) remains, which contains small amounts of impurity.

c) Ethyl 3-(4-fluorophenyl)-2-(4-methylsulphlylphenyl)-6,7-dihydro-5H-pyrrolizine-1-carboxylate A solution of ethyl 2-bromo-3-(4-methylsulphonylphenyl)acrylate (0.67 g, 2 mmol) in acetic anhydride (4 ml) is treated with N-4-fluorobenzoylproline (0.47 g, 2 mmol), and the reaction vessel is immersed in an oil bath maintained at 150° C. The mixture is refluxed for 72 h with stirring; it is then allowed to cool. The black-coloured starting solution is concentrated in vacuo, the residue is taken up in ethyl acetate (20 ml) and the acetic acid-containing ethyl acetate solution is first washed with NaHCO$_3$ solution (10% strength, 20 ml) until acid-free. The ethyl acetate phase then washed with water (20 ml) is dried using Na$_2$SO$_4$ sicc. and concentrated in a rotary evaporator. The residue obtained (1.0 g) is purified by CC (Al$_2$O$_3$/ether-THF 9:1): fraction 11/12 (Rf 0.75) affords 20 mg of product A. The ethyl 2-bromo-3-(4-methylsulphonylphenyl)acrylate (0.5 g) employed is recovered in fractions 2–8 (Rf 0.8) and 170 mg of the N-4-fluorobenzoylproline in fractions 15–31 (Rf 0.5).

Y: 20 mg, C$_{23}$H$_{22}$FNO$_4$S MW=427.50; $^1$H-NMR (CDCl$_3$): δ (ppm)=7.80–7.76 u. 7.43–7.38 (AA'BB', 4H, arom), 7.09–6.96 (m, 4H, arom), 4.23–4.12 (q, J=7.1 Hz, 2H), 4.03–3.96 (t, J=7.2 Hz, 2H), 3.27–3.19 (t, J=7.4 Hz, 2H), 3.05 (s, CH$_3$), 2.63–2.49 (quin, J=7.2 Hz, 2H), 1.26–1.19 (t, J=7.0 Hz, CH$_3$).

EXAMPLE 13

{4-[3-(4-Fluorophenyl)-6,7-dihydro-5H-pyrrolizin-2-yl]phenyl}methyl sulphone a) Methyl [4-(2-nitrovinyl)phenyl]sulphone A mixture of 4-methylsulphonylbenzaldehyde (1.84 g, 10 mmol), nitromethane (1.0 ml, 1.134 g, 18.5 mmol), anhydrous ammonium acetate (1.5 g, 19 mmol) and glacial acetic acid (7.0 ml) is refluxed at 120° C. for 3 h. The mixture is treated with water (20 ml) and extracted three times with ether (30 ml). The collected ether phase is first washed with NaHCO$_3$ solution (10% strength, 20 ml) until acid-free. The ether phase subsequently washed with water (20 ml) is dried using Na$_2$SO$_4$ sicc. and concentrated in a rotary evaporator. Yield: 54.0% (1.23 g).

or

A mixture of 4-methylsulphonylbenzaldehyde (22.08 g, 120 mmol) and nitromethane (12.5 ml, 14.2 g, 233 mmol) in MeOH (1 l) is cooled to 3° C. in an ice bath; sodium hydroxide solution (32%, 420 ml, 567 g, 135 g of NaOH, 3.36 mol) is then added dropwise, a clear solution being formed after addition of 30 ml (time needed 1 h). The mixture is stirred at 10° C. for 2 h and then added dropwise at 10° C. to initially introduce HCl (20%, 1080 ml, 216 g of HCl, 5.9 mol) (time needed 40 min). The HCl-acidic mixture is stirred until formation of the precipitate is complete (30 min). The nitrostyrene crystallizate is filtered off with suction, washed with ice water until the wash phase gives a neutral reaction and dried over P$_2$O$_5$ in an evacuated desiccator. The yield of crystallizate is 16.03 g after drying.

Y: 58.8% (16.03 g), C$_9$H$_9$NO$_4$S, MW=227.24; IR (NaCl): 1/λ (cm$^{-1}$)=3105, 1640, 1520, 1341, 1308, 1148, 956, 773, 664, 547; $^1$H-NMR (CDCl$_3$): δ (ppm)=8.07–8.02 u. 7.77–7.73 (AA'BB', 4H, arom), 8.035/7.645 (AB, J=14 Hz, 2H, CH=CH), 3.10 (s, CH$_3$).

b) {4-[3-(4-Fluorophenyl)-6,7-dihydro-5H-pyrrolizin-2-yl]phenyl}methyl sulphone

A solution of N-4-fluorobenzoylproline (11.08 g, 46.7 mmol) in acetic anhydride (4 ml) is maintained at 80° C. IT in an oil bath. Methyl [4-(2-nitrovinyl)phenyl]sulphone (9.66 g, 42.5 mmol) is added, and the reaction vessel is immersed in an oil bath maintained at 150° C. The mixture is refluxed for 4 h with stirring; after the evolution of CO$_2$ has subsided, it is allowed to cool. The black-coloured starting solution is taken up in ethyl acetate (200 ml), and the acetic acid-containing ethyl acetate solution is washed with Na$_2$CO$_3$ solution (10% strength, 20 ml) until acid-free. The ethyl acetate phase subsequently washed with saturated NaCl solution (200 ml) is dried using $Na_2SO_4$ sicc. and concentrated in a rotary evaporator. The residue obtained (22.6 g) is taken up in ethyl acetate (30 ml) and purified by CC ($Al_2O_3$/ether): fractions 4–7 (Rf 0.75) afford 1.45 g of product A, and fractions ⅜ (Rf 0.75+Rf 0.6) are a mixed fraction and afford products A+B. The structural isomer B (0.88 g) is obtained in fractions 10–14 (Rf 0.6).

Product A: {4-[3-(4-Fluorophenyl)-6,7-dihydro-5H-pyrrolizin-2-yl]phenyl}methyl sulphone Y: 8.7% (1.45 g), $C_{20}H_{18}FNO_2S$, MW=355.43; Mp: 153.7° C.; IR (NaCl): $1/\lambda$ $(cm^{-1})$=1591, 1525, 1509, 1301, 1223, 1148, 1091, 956, 843, 769, 547; $^1$H-NMR ($CDCl_3$): $\delta$ (ppm)=7.75–7.71 u. 7.39–7.35 (AA'BB', 4H, -pyridyl), 7.28–7.21 (m, 2H, arom), 7.10–7.01 (m, 2H, arom), 6.12 (s, CH), 3.94–3.88 (t, J=6.9 Hz, $CH_2$), 3.04 (s, $CH_3$), 2.99–2.92 (t, J=7.3 Hz, $CH_2$), 2.59–2.44 (quin, J=7.2 Hz, $CH_2$); $^{13}$C-NMR ($CD_3OD$): $\delta$ (ppm)=164.6, 159.6, 143.0, 137.7, 136.4, 131.2, 131.0, 128.8, 128.7, 128.0, 127.4, 125.1, 124.1, 116.1, 115.6, 100.2, 45.9, 44.6, 27.4, 24.5.

Product B: {4-[3-(4-Fluorophenyl)-6,7-dihydro-5H-pyrrolizin-1-yl]phenyl}methyl sulphone Y: 5.3% (0.88 g), $C_{20}H_{18}FNO_2S$, MW=355.43; Mp: 176.00–179.00° C., IR (NaCl): $1/\lambda$ $(cm^{-1})$=1594, 1525, 1488, 1302, 1223, 1146, 1092, 971, 959, 836, 791, 769; $^1$H-NMR ($CDCl_3$): $\delta$ (ppm)=7.91–7.86 u. 7.66–7.61 (AA'BB', 4H, -pyridyl), 7.48–7.41 (m, 2H, arom), 7.16–7.05 (m, 2H, arom), 6.67 (s, CH), 4.18–4.11 (t, J=7.1 Hz, $CH_2$), 3.20–3.13 (t, J=7.3 Hz, $CH_2$), 3.07 (s, $CH_3$), 2.72–2.57 (quin, J=7.2 Hz, $CH_2$); $^{13}$C-NMR ($CD_3OD$): $\delta$ (ppm)=164.1, 159.2, 142.0, 137.6, 135.7, 129.3, 129.0, 128.9, 127.9, 127.7, 127.6, 125.1, 116.0, 115.5, 114.5, 108.9, 46.6, 44.7, 27.8, 25.8.

EXAMPLE 14

4-[2-Cyclohexyl-3-methyl-6,7-dihydro-5H-pyrrolizin-1-yl]benzenesulphonamide a) Ethyl 1-acetylcyclohexanecarboxylate Ethyl acetoacetate (52.06 g, 0.40 mol) and 1,5-dibromopentane (92.0 g, 0.40 mol) are mixed in a 200 ml 3-necked flask and maintained at 80° C. in an oil bath. An Na ethoxide solution (21%, 245 g, 0.75 mol) is added dropwise from a dropping funnel over the course of 45 min, the temperature then being kept between 70 and 80° C. for 1 h. A GC sample shows a starting material/by-product/product ratio of 1:4:13, altogether a proportion of 18% of the acid cleavage product ethyl cyclohexane-carboxylate.

Water (100 ml) is added and a water/ethanol mixture (200 ml) is removed in vacuo, the mixture is cooled to RT and water (100 ml) is again added. The mixture is extracted with diethyl ether (250 ml) and the phases are separated. The aqueous phase is extracted 2 times with diethyl ether (150 ml), and the ether phase combined with the re-extracts is washed with satd. NaCl solution (100 ml). The ethereal product solution is dried over $Na_2SO_4$ sicc. and concentrated in vacuo.

The oil fraction obtained (92 g, 116%) contains the desired product in a concentration of 65% (GC). Isolation is carried out by fractional distillation: the fraction obtained between 83–90° C./0.3 bar (33 g) contains the compound sought in 90% purity (yield: 38%)

Y: 41.5%=33 g (90% strength), $C_{11}H_{18}O_3$, MW=198.26; Bp: 52.00 (0.075 mmHg); IR (NaCl): $1/\lambda$ $(cm^{-1})$=2938, 2858, 1735, 1712, 1452, 1361, 1303, 1214, 1133; $^1$H-NMR ($CDCl_3$): $\delta$ (ppm)=4.254.15 (q, $CH_2$, J=7.1 Hz), 2.15 (s, $CH_3$), 2.11–1.40 (m, 10H, cyclohex.), 1.30–1.23 (t, $CH_3$, J=7.1 Hz); $^{13}$C-NMR ($CDCl_3$): $\delta$ (ppm)=205.6, 172.2, 61.1, 30.5, 25.8, 25.2, 22.7, 14.0.

b) Ethyl 1-bromoacetylcyclohexanecarboxylate

Ethyl 1-acetylcyclohexanecarboxylate (2.2 g, 90% strength, 10 mmol) is dissolved in abs. $CH_2Cl_2$ (10 ml). A solution of bromine (1.6 g, 10 mmol) in $CH_2Cl_2$ (3 ml) is added dropwise to the solution in the course of 45 min. The mixture is freed from liberated HBr by stirring intensively for 3 hours (GC sample). The reaction solution is neutralized using 5 ml of semi-saturated $NaHCO_3$ solution and the $CH_2Cl_2$ phase separated in a separating funnel is dried over $Na_2SO_4$ sicc. and concentrated in vacuo. A residue of 3.08 g (111%) remains, which according to GC analysis contains 78.8% of product (86.8% yield) and 1,5-dibromopentane from the preceding reaction as an impurity.

Y: 111%=3.1 g (78.8% strength), $C_{11}H_{17}BrO_3$, MW=277.16; Bp: 98.00 (0.0005 mmHg); IR (NaCl): $1/\lambda$ $(cm^{-1})$=2939, 2858, 1735, 1720, 1451, 1304, 1221, 1137, 1022; $^1$H-NMR ($CDCl_3$): $\delta$ (ppm)=4.24–4.13 (q, $CH_2$, J=7.2 Hz), 4.11 (s, $CH_2$), 2.11–1.37 (m, 10H, cyclohex.), 1.28–1.21 (t, $CH_3$, J=7.2 Hz); $^3$C-NMR ($CDCl_3$): $\delta$ (ppm)= 198.6, 171.5, 61.6, 60.4, 31.8, 30.9, 25.0, 22.6, 14.0.

c) Ethyl 1-(1-phenyl-6,7-dihydro-5H-pyrrolizin-2yl)cyclohexanecarboxylate

A mixture of 2-benzyl-1-pyrroline (11.65 g, 60 mmol) and ethyl 1-bromoacetylcyclohexanecarboxylate (15.2 g, 78.8% strength, 45 mmol) is heated at 100° C. for 1.5 h without solvent; 2-benzyl-1-pyrroline (5.82 g, 30 mmol) is then again added and the temperature is kept at 100° C. for a further hour. The mixture is cooled and the melt residue is taken up in $CH_2Cl_2$ (200 ml) and extracted twice with dilute HCl (3% strength, 200 ml). The HCl-acidic phase is back-washed with $CH_2Cl_2$ (100 ml) and the combined $CH_2Cl_2$ solutions are dried over $Na_2SO_4$ sicc. and concentrated to 50 ml in vacuo. This concentrate is transferred to a short column of $Al_2O_3$ (neutral, for TSC, ICl), and the column is then eluted with a mixture of $CH_2Cl_2$ and n-hexane (1:2, 250 ml). The eluate is concentrated to dryness in vacuo; the residue contains 12.6 g of the product (86.9% of theory) in 90% purity.

Y: 87%=12.6 (90% strength), $C_{22}H_{27}NO_2$, MW=337.47; IR (NaCl): $1/\lambda$ $(cm^{-1})$=2935, 2857, 1720, 1450, 1298, 1214, 1129, 702; $^1$H-NMR ($CDCl_3$): $\delta$ (ppm)=7.35–7.16 (5H, arom), 6.58 (s, 1H), 4.01–3.85 (m, 2×$CH_2$), 2.71–2.63 (t, $CH_2$), 2.49–2.32 (q, $CH_2$), 2.25–2.14 ($CH_2$), 1.69–1.22 (m), 1.19–1.12 (t, $CH_3$); $^{13}$C-NMR ($CDCl_3$): $\delta$ (ppm)=176.3, 138.1, 135.9, 130.6, 129.7, 127.4, 125.8, 114.8, 111.4, 60.2, 47.6, 46.7, 35.6, 27.0, 25.8, 23.8, 23.3, 14.0.

d) 1-(3-Carboxymethyl-1-phenyl-6,7-dihydro-5H-pyrrolizin-2-yl)cyclohexanecarboxylic acid A solution of ethyl 1-(1-phenyl-6,7-dihydro-5H-pyrrolizin-2-yl)cyclohexanecarboxylate (2.03 g, 5.5 mmol) in abs. THF (10 ml) is treated under argon with one drop of triethylamine; a solution of oxalyl dichloride (1.12 g, 8.8 mmol) in THF abs. (2 ml) is then added dropwise in small portions while cooling in an ice bath and the mixture is subsequently stirred after the addition for a further 30 min (TLC: $SiO_2$, ether-n-hexane (1:1): starting material Rf 0.8, product 0.4). Without isolation of the oxalyl chloride intermediate, hydrazine hydrate (80% strength, 3.8 ml, 60 mmol) is then added dropwise over the course of 30 min. The reaction mixture is first heated to an IT of 85° C. in an oil bath and THF (11 ml) is simultaneously distilled over via a distillation bridge. After cooling to about 50° C., diethylene glycol (7.0 ml) and, in small portions, KOH (6.3 g, 112 mmol) are added. The mixture is slowly heated to 140° C. in steps (oil bath 180° C.). While initial residual THF, water (3 ml) and excess hydrazine distill over, a reaction temperature of 140–150° C. is achieved after about 30 min, which is maintained for 3 h.

The mixture is cooled, water (20 ml) is added at 80° C. and it is rendered acidic (pH 2.0, ice bath cooling) using HCl 20% strength. The light yellow solid depositing is filtered off with suction and washed with 10 ml of ice water until the wash water gives a neutral reaction. After drying in a desiccator ($P_2O_5$), 2.14 g (87% of theory) of dicarboxylic acid remain.

Y: 87%=2.1 g (92% strength), $C_{22}H_{25}NO_4$, MW=367.45; Mp: 147.00–157.00° C.; IR (NaCl): $1/\lambda$ ($cm^{-1}$)=2930, 2856, 1703, 1602, 1450, 1079, 702; $^1$H-NMR ($CDCl_3$): δ (ppm)= 9.14 (COOH), 7.27–7.23 (m, arom 5H), 3.90–3.83 (t, $CH_2$, J=6.8 Hz), 3.79 (s, $CH_2$), 2.64–2.57 (t, $CH_2$, J=7.1 Hz), 2.43–2.33 (m, $CH_2$), 2.19–2.12 (m, 2H), 1.62–1.10 (m, 10H, cyclohex.); $^3$C-NMR ($CDCl_3$): δ (ppm)=181.8, 177.5, 139.7, 134.9, 131.0, 127.7, 126.1, 124.8, 117.0, 115.3, 61.8, 49.5, 35.8, 33.4, 29.7, 26.4, 25.8, 24.2, 23.8, 19.9.

e) 6-Cyclohexyl-5-methyl-7-phenyl-2,3-dihydro-1H-pyrrolizine 1-(3-Carboxymethyl-1-phenyl-6,7-dihydro-5H-pyrrolizin-2-yl)cyclohexanecarboxylic acid (1.5 g, 3.7 mmol) is immersed in an oil bath of 150° C. for 30 min in a 25 ml flask. The release of $CO_2$ is checked via a bubble counter. The still warm melt is digested with diisopropyl ether (15 ml). The insoluble crystalline residue is filtered off with suction and dried. 0.84 g (82% of theory) of decarboxylation product 6-cyclohexyl-5-methyl-7-phenyl-2,3-dihydro-1H-pyrrolizine (TLC: $SiO_2$, ether-n-hexane (1:1): starting material Rf 0–0.2, product 0.9) is obtained.

Y: 82%=0.84 g (97% strength), $C_{20}H_{25}N$, MW=279.43; Mp: 107.30° C.; IR (NaCl): $1/\lambda$ ($cm^{-1}$)=2926, 2849, 1602, 1446, 1423, 1378, 1301, 1087, 1071, 767, 689; $^1$H-NMR ($CDCl_3$): δ (ppm)=$CDCl_3$: 7.39–7.15 (m, arom 5H), 3.90–3.83 (t, $CH_2$, J=7.0 Hz), 2.91–2.84 (t, $CH_2$, J=7.3 Hz), 2.49–2.42 (t, $CH_2$, J=7.2 Hz), 2.30 (s, $CH_3$), 1.84–1.60 u. 1.29–1.19 (m, 10H, cyclohex.); $^{13}$C-NMR ($CDCl_3$): δ (ppm)=$CDCl_3$: 137.7, 131.4, 129.2, 128.0, 126.4, 124.8, 118.9, 114.8, 44.4, 36.0, 33.4, 27.3, 126.7, 26.3, 24.4, 22.9, 11.9.

f) 4-(2-Cyclohexyl-3-methyl-6,7-dihydro-5H-pyrrolizin-1-yl)benzenesulphonamide

6-Cyclohexyl-5-methyl-7-phenyl-2,3-dihydro-1H-pyrrolizine (0.56 g, 2 mmol) is stirred into chlorosulphonic acid (1.0 ml, 1.745 g, 15 mmol) at RT. After a reaction time of 3 h (TLC: $SiO_2$, ether-n-hexane (1:1): starting material Rf 0.9, intermediate Rf 0.7), the mixture is heated at 80° C. for a short time (30 min) and cooled again. $CHCl_3$ (15 ml) is added and ice water (15 ml) is cautiously added dropwise. The phases are separated and the aqueous sulphuric acid phase is extracted a further 5 times with $CHCl_3$ (10 ml). The $CHCl_3$ phase is dried over $Na_2SO_4$ sicc. and a stream of dry $NH_3$ is passed into the solution over the course of 30 min (TLC: $SiO_2$, ether-n-hexane (1:1): intermediate Rf 0.7, final product Rf 0.3). The mixture is stirred for a further 60 min, filtered and concentrated in vacuo (crude yield 210 mg, 29% of theory, light beige substance). The residue is dissolved in hot EtOH (9 ml) and recrystallized in the cold again after addition of water (4 ml). 106 mg (14.9%) of 98.7% product having a melting point of 256.2° C. crystallize.

Y: 15%=0.1 g (99% strength), $C_{20}H_{26}N_2O_2S$, MW=358.51 Mp: 256.20; IR (NaCl): $1/\lambda$ ($cm^{-1}$)=3343, 3232, 2926, 2849, 1595, 1334, 1161, 1094, 735, 548; $^1$H-NMR ($CDCl_3$): δ (ppm)=7.91–7.86 u. 7.39–7.35 (AA'BB', 4H, arom), 4.78 (s, $NH_2$), 3.91–3.84 (t, $CH_2$, J=7.0 Hz), 2.93–2.85 (t, $CH_2$, J=7.3 Hz), 2.56–2.46 (m, $CH_2$), 2.30 (s, $CH_3$), 1.81–1.59 u. 1.27–1.21 (m, 10H, cyclohex.); $^{13}$C-NMR ($CDCl_3$): δ (ppm)=143.0, 137.4, 132.5, 129.2, 126.4, 119.8, 113.4, 44.6, 36.1, 33.3, 27.3, 26.7, 26.2, 24.6, 11.9.

EXAMPLE 15

4-[2-(4-Fluorophenyl)-3-methyl-6,7-dihydro-5H-pyrrolizin-1-yl]benzenesulphonamide A flask containing chlorosulphonic acid (84.2 g, 0.72 mol) is cooled to 0–5° C. 2-(4-Fluorophenyl)-3-methyl-1-phenyl-6,7-dihydro-5H-pyrrolizine (Example 8 d, 35 g, 0.12 mol) is stirred in in 7 portions in the course of 1.5 h under a dry argon atmosphere. HCl is immediately released. The mixture is stirred further at RT for a further 30 h. The reaction mixture is then quenched in ice water (0.4 kg). The sulphonyl chloride depositing is taken up in $CHCl_3$ (150 ml), and the ice-water phase is extracted with $CHCl_3$ (2×50 ml). These $CHCl_3$ extracts are dried using $Na_2SO_4$ sicc.

The dried $CHCl_3$ solution of the sulphonyl chloride is made up (800 ml) with dry $CHCl_3$ ($CaCl_2$ sicc.) and transferred to a flask. Ammonia (dried over NaOH) is introduced into the dilute solution, which is cooled in an ice water bath to an internal temperature of 0–10° C., from a pressurized container. After complete saturation of the solution with $NH_3$, the white suspension formed is stirred at low temperature (5–10° C.) for a further 3 h. The mixture is then poured into ice water (300 ml) and stirred. The organic phase is then separated in a separating funnel and washed twice with water (200 ml), dried over $Na_2SO_4$ sicc. and concentrated in vacuo after filtration. The residue is crystallized from methanol. The crystals are collected, washed with diisopropyl ether and dried. 12.5 g (27%) of product remain.

Y: 27%=12.5 g (94%), $C_{20}H_{19}FN_2O_2S$, MW=370.45; Mp: 120.0° C.; IR (NaCl): $1/\lambda$ ($cm^{-1}$)=3350, 3266, 1595, 1538, 1501, 1220, 1160, 836, 604, 549; $^1$H-NMR ($CDCl_3$): δ (ppm)=7.71–7.67 (AA',2H, arom), 7.25–6.94 (BB'+ AA'BB', 6H, arom), 4.79 (s, 2H, $CH_2$), 3.99–3.92 (t, 2H, $CH_2$), 3.08–3.0 (t, 2H, $CH_2$), 2.64–2.5 (quin 2H, $CH_2$), 2.2 (s, 3H, $CH_3$).

EXAMPLE 16

4-[3-Chloro-2-(4-fluorophenyl)-6,7-dihydro-5H-pyrrolizin-1-yl]benzenesulphonamide a) 5-Chloro-6-(4-fluorophenyl)-7-phenyl-2,3-dihydro-1H-pyrrolizine The clear solution of 6-(4-fluorophenyl)-7-phenyl-2,3-dihydro-1H-pyrrolizine (Example 8 d, 2.77 g, 10 mmol) in THF (20 ml) is treated at RT with N-chlorosuccinimide (NCS, 1.34 g, 10 mmol). The solution, immediately turning from yellow to black-coloured with spontaneous heating, is stirred for a further 10 min, then adsorbed on an $Al_2O_3$ column (100 g, TSC-ICI), and the substance sought is eluted with ethyl acetate-n-hexane 1:9 (Rf=0.8, starting material Rf=0.6). The eluate fractions are concentrated in vacuo and the residue is crystallized from diisopropyl ether: 1.63 g (52%)

Y: 52% (1.63 g), $C_{19}H_{15}ClFN$, MW=311.79; Mp: 127° C.; IR (NaCl): $1/\lambda$ $(cm^{-1})$=1601, 1530, 1490, 1400, 1294, 1219, 836, 783, 736, 705; $^1$H-NMR $(CDCl_3)$: $\delta$ (ppm)= 7.25–6.93 (m, 9H, arom), 4.01 (t, 2H, J=7.1 Hz, $CH_2$), 3.04 (t, 2H, J=7.3 Hz, $CH_2$), 2.54 (quin, 2H, J=7.2 Hz, $CH_2$); $^{13}$C-NMR $(CDCl_3)$: $\delta$ (ppm)=163.9, 159.0, 135.4, 133.5, 131.6, 131.4, 130.3, 130.2, 128.3, 128.2, 125.2, 121.0, 115.2, 114.7, 45.5, 26.7, 25.3.

b) 4-[3-Chloro-2-(4-fluorophenyl)-67-dihydro-5H-pyrrolizin-1-yl]benzenesulphonamide 5-Chloro-6-(4-fluorophenyl)-7-phenyl-2,3-dihydro-1H-pyrrolizine (1.39 g, 4.5 mmol) is added in portions (5) to chlorosulphonic acid (3.75 g, 32.2 mmol) cooled to 0° C. in the flask and the mixture is stirred at RT for 16 h. The black-coloured mixture is diluted with $CHCl_3$ (25 ml) and cautiously poured onto ice (40 ml). The $CHCl_3$ phase is separated in a separating funnel; the aqueous phase and emulsion layer are extracted twice with $CHCl_3$ (80 ml). The $H_2O$ phase and emulsion layer are saturated with NaCl and extracted with ethyl acetate.

The $CHCT_3$ extract is dried over $Na_2SO_4$ sicc., cooled to 2° C. in an ice bath and saturated with $N_{13}$ from a pressurized container (30 min). The saturated solution is stirred for 1 h, the ammonium chloride crystallized from the reaction mixture is filtered off with suction, and the filtrate is concentrated. The residue (0.52 g, 89% purity) crystallizes from ethanol: 0.27 g (15%).

Y: 15% (0.27 g), $C_{19}H_{16}ClFN_2O_2S$, MW=390.87; Mp: (162° C. dec; IR (NaCl): $1/\lambda$ $(cm^{-1})$=3376, 3269, 1597, 1529, 1396, 1329, 1224, 1163, 1087, 839; $^1$H-NMR $(CDCl_3+DMSO-d6)$: $\delta$ (ppm)=7.75–7.71 and 7.33–7.00 (m, 8H, arom), 5.30 (s, 2H, $NH_2$), 4.03 (t, 2H, J=7.1 Hz, $CH_2$), 3.05 (t, 2H, J=7.3 Hz, $CH_2$), 2.58 (quin, 2H, J=7.1 Hz, $CH_2$); $^{13}$C-NMR $(CDCl_3/DMSO-d6)$: $\delta$ (ppm)=163.8, 158.9, 139.7, 138.9, 134.5, 131.4, 131.3, 129.7, 129.6, 127.9, 126.0, 120.9, 115.3, 114.8, 113.4, 45.5, 39.4, 26.4, 25.4.

EXAMPLE 17
4-[2-(4-Chlorophenyl)-3-methyl-6,7-dihydro-5H-pyrrolizin-1-yl]benzenesulphonamide a) 6-(4-Chlorophenyl)-7-phenyl-2,3-dihydro-1H-pyrrolizine (according to Laufer et al. J. Med. Chem. 1994, 37, 1894–1897) 2-Benzyl-1-pyrroline (Example 1 a, 19.8 g, 80% strength, 0.1 mol), dissolved in MeOH (300 ml) is treated with 4-chlorophenacyl bromide (23,4 g, 0.1 mol) and then with $NaHCO_3$ (10 g, 0.12 mol) and stirred at RT for 16 h with exclusion of light. Precipitated crystallizate is filtered off with suction and washed with MeOH. 16.4 g (56%) of product are obtained after drying.

Y: 56% (16.4 g), $C_{19}H_{16}ClN$, MW=293.80; Mp: 142.0° C.; $C_{19}H_{16}ClN$, MW=293.80; IR (NaCl): $1/\lambda$ $(cm^{-1})$=3447, 2983, 2879, 1600, 1524, 1485, 1401, 1187, 1088, 1010, 837, 765, 701; $^1$H-NMR $(CDCl_3)$: $\delta$ (ppm)=7.26–7.13 (m, 9H, arom), 6.748 (s, 1H, —CH═C), 4.026 (t, sH, J=7.2 Hz, $CH_2$), 2.980 (t, 2H, J=7.4 Hz, $CH_2$), 2.536 (quin, 2H, $CH_2$, J=7.2 Hz).

b) 2-[2-(4-Chlorophenyl-1-phenyl-6,7-dihydro-5H-pyrrolizin-3-yl]acetic acid according to Laufer et al. J. Med. Chem. 1994, 37, 1894–1897

Oxalyl dichloride (2.8 g, 0.0225 mol) is added dropwise to an ice-cold solution of 6-(4-chlorophenyl)-7-phenyl-2,3-dihydro-1H-pyrrolizine (see above, 4.35 g, 0.015 mol) in TIF (50 ml) at 0–10° C. After addition is complete, the mixture is stirred for 15 min and the excess of acid chloride is then cautiously decomposed (gas and foam formation!) using ice water (30 ml). Hydrazine (9.5 ml, 80%, 0.15 mol) is added dropwise, the mixture is stirred for 30 min and diethylene glycol (18 ml) is poured in. THF and water are distilled off under atmospheric pressure at a bath temperature of 100–110° C. (foam formation from 105° C.!). The mixture is cooled to 60° C. and potassium hydroxide solution (50% in water, 15.7 g of KOH 85%, 0.238 mol) is added in 5 portions, the temperature is increased in steps to 140° C. (foam formation!) and water and residual solvents are driven off. This temperature is maintained in the bottom until the evolution of gas subsides (1 h) and the colour of the mixture lightens. The mixture cooled to 60° C. is poured onto ice (300 g) and acidified to pH 2–3 with conc. HCl with ice-cooling (temp. <10° C.).

The product depositing is extracted with ethyl acetate (150 ml), washed with water until neutral, dried using $Na_2SO_4$ sicc. and concentrated at 45° C. in the presence of heat until the start of crystallization. The crystal mass deposited at 5° C. is filtered off with suction and washed with cold ethyl acetate and dried.

Y: 46%=2.4 g (%), $C_{21}H_{18}ClNO_2$, MW=351.84; Mp: 170° C.; IR (NaCl): $1/\lambda$ $(cm^{-1})$=2950, 1710, 1596, 1418, 1232, 830, 705; $^1$H-NMR $(CDCl_3)$: $\delta$ (ppm)=7.27–7.05 (m, 9H, arom), 6.74 (s, 1H, —CH═C), 4.06–3.99 (t, 2H, J=7.0 Hz, $CH_2$), 3.60 (s, 2H, $CH_2$), 3.03 (t, 2H, J=7.0 Hz, $CH_2$), 2.61 (quin, 2H, J=7.0 Hz, $CH_2$).

c) 6-(4-Chlorophenyl)-5-methyl-7-phenyl-2,3-dihydro-1H-pyrrolizine

A flask, filled with crystalline solid substance of 2-[2-(4-chlorophenyl)-1-phenyl-6,7-dihydro-5H-pyrrolizin-3-yl]-2-acetic acid (1.8 g, 0.005 mol), is heated at 180° C. in an oil bath until the $CO_2$ release checked by a gas bubble counter subsides (10–15 min). The residue cooled to 50° C. is stirred with diisopropyl ether (50 ml) until it has cooled to room temperature, then the undissolved crystals are filtered off with suction and the crude product is crystallized again from diisopropyl ether if required.

1.0 g (64%) of white, crystalline compound are obtained.

Y: 64%=1.0 g (99%), $C_{20}H_{18}ClN$, MW=307.83; IR (NaCl): $1/\lambda$ $(cm^{-1})$=3447, 2943, 1600, 1532, 1415, 1116, 708; $^1$H-NMR $(CDCl_3)$: $\delta$ (ppm)=7.255–7.04 (m, 9H, arom), 3.94 (t, 2H, J=7 Hz, $CH_2$), 3.03 (t, 2H, $CH_2$), 2.54 (quin, 2H, J=7 Hz, $CH_2$), 2.236 (s, 3H, $CH_3$).

d) 4-[2-(4-Chlorophenyl)-3-methyl-6,7-dihydro-5H-pyrrolizin-1-yl]benzenesulphonamide 6-(4-Chlorophenyl)-5-methyl-7-phenyl-2,3-dihydro-1H-pyrrolizine (0.8 g, 0.0026 mol) is added to chlorosulphonic acid (1.87 g, 0.0167 mol), cooled to 0° C. in the flask and the mixture is stirred at RT for 5 h. The chlorosulphonic acid is cautiously destroyed with water (10 ml) while cooling in an ice bath, and resultant sulphuric acid is diluted. Resultant sulphochloride is extracted with ethyl acetate (50 ml), and the extract is dried over Na$_2$SO$_4$ sicc. and concentrated. The residue remaining after evaporation of the solvent in vacuo is taken up in dry CHCl$_3$ (CaCl$_2$), and the CHCl$_3$ solution is saturated with NH$_3$ from a pressurized container. The saturated solution is stirred for 2 h, saturated again with NH$_3$ and, after stirring for a further 2 hours, the ammonium chloride crystallized from the reaction mixture is filtered off with suction. The filtrate is concentrated and the residue is crystallized from diethyl ether: 0.4 g (40%).

Y: 40%=0.4 g (97%), C$_{20}$H$_{19}$ClN$_2$O$_2$S, MW=386.90; IR (NaCl): 1/λ (cm$^{-1}$)=3336, 3260, 1596, 1433, 1426, 1315, 1160, 1118, 1093, 836, 727, 603, 548; $^1$H-NMR (CDCl$_3$): δ (ppm)=7.72 (d, 2H, arom), 7.27–7.04 (m, 6H, arom), 3.99–3.92 (t, 2H, CH$_2$), 3.06–2.99 (t, 2H, CH$_2$), 2.64–2.54 (quin, 2H, CH$_2$), 2.21 (s, 3H, CH$_3$).

EXAMPLE 18

Ethyl 2-(4-chlorophenyl)-1-(4-sulphamoylphenyl)-6,7-dihydro-5H-pyrrolizine-3-carboxylate a) Ethyl 2-(4-chlorophenyl)-1-phenyl-6,7-dihydro-5H-pyrrolizine-3-carboxylate 6-(4-Chlorophenyl)-7-phenyl-2,3-dihydro-1H-pyrrolizine (Example 17 a, 1.5 g, 5.1 mmol), dissolved in THF (10 ml) is treated with 1 drop of triethylamine (about 50 mg). A solution of diphosgene (0.5 g, 2.5 mmol), dissolved in THF (5 ml) is added dropwise to this solution at RT and it is stirred for 8 h.

Ethanol (abs., 3 ml) is then added, and the mixture is stirred at RT for a further 12 h. The solvent is completely removed in vacuo (45° C.), and the residue is washed with water (5 ml) and finally recrystallized from a little diisopropyl ether.

Y (after drying): 87.1% (1.62 g), C$_{22}$H$_{20}$ClNO$_2$, MW=365.86; Mp: 143.7° C.; IR (NaCl): 1/λ (cm$^{-1}$)=2985, 2969, 1694, 1545, 1473, 1415, 1385, 1311, 1221, 1126, 1097; $^1$H-NMR (CDCl$_3$): δ (ppm)=7.28–7.17 (m, 5H, arom), 7.14–6.91 (AA'BB', 4H, arom), 4.40 (t, CH$_2$), 4.10 (q, OCH$_2$), 3.00 (t, CH$_2$), 2.55 (quin, CH$_2$), 1.15 (t, CH$_3$).

b) Ethyl 2-(4-chlorophenyl-1-(4-sulphamoylphenyl)-6,7-dihydro-5H-pyrrolizine-3-carboxylate Ethyl 2-(4-chlorophenyl)-1-phenyl-6,7-dihydro-5H-pyrrolizine-3-carboxylate (1.6 g, 4.4 mmol) is added in 4 portions to the chlorosulphonic acid (8.0 ml, 14.0 g, 120 mmol) cooled to −10° C. and protective gas is introduced. After stirring at RT for 15 h, the mixture is diluted with dry CH$_2$Cl$_2$ (100 ml), and a stream of NH$_3$ gas is passed in from a pressurized container until it is saturated. The suspension of ammonium salts is subsequently stirred for a further 2 h and then treated with water (200 ml). A weakly acidic pH (pH 5.0) is set using dil. HCl (10%) and the phases are separated. The aqueous phase is extracted with ethyl acetate (100 ml). The combined organic phases are dried over Na$_2$SO$_4$ sicc., and the solvent mixture is removed in vacuo. The residue obtained is crystallized from ethanol (1.8 g, 92.3%).

Y: 92.3% (1.8 g), C$_{22}$H$_{21}$ClN$_2$O$_4$S, MW=444.94; Mp: dec 320° C.; IR (NaCl): 1/λ (cm$^{-1}$)=3248, 2980, 1589, 1518, 1375, 1311, 1163; $^1$H-NMR (CD$_3$OD): δ (ppm)=7.63–7.59 (AA', 2H, arom), 7.27–7.11 (BB'+AA', 4H, arom), 7.08–7.04 (BB', 2H, arom), 4.86 (s, SONH$_2$), 4.37 (t, 2H, CH$_2$), 4.08 (q, 2H, OCH$_2$), 3.03 (t, 2H, CH$_2$), 2.65 (quin, 2H, CH$_2$), 1.09 (t, 3H, CH$_3$).

EXAMPLE 19

Methyl 2-(4-chlorophenyl)-1-(4-sulphamoylphenyl)-6,7-dihydro-5H-pyrrolizine-3-carboxylate a) Methyl 2-(4-chlorophenyl)-1-phenyl-6,7-dihydro-5H-pyrrolizine-3-carboxylate 6-(4-Chlorophenyl)-7-phenyl-2,3-dihydro-1H-pyrrolizine (Example 17 a, 1.5 g, 5.1 mmol), dissolved in THF (10 ml), is treated with 1 drop of triethylamine (about 50 mg). A solution of diphosgene (0.5 g, 2.5 mmol), dissolved in THF (5 ml), is added dropwise to this solution at RT and it is stirred for 8 h. Methanol (abs., 3 ml) is then added, and the mixture is stirred at RT for a further 12 h. The solvent is completely removed in vacuo (45° C.). The resinous residue is dissolved in CHCl$_3$ (20 ml) and washed twice with water (20 ml). After the removal of the solvent in vacuo, a residue which is recrystallized from a little diisopropyl ether is obtained from the CHCl$_3$ phase dried using Na$_2$SO$_4$ sicc.

Y: 99.5% (1.98 g), C$_{21}$H$_{18}$ClNO$_2$, MW=351.84; IR (NaCl): 1/λ (cm$^{-1}$)=2947, 1630, 1463, 1396, 1227, 1013, 708; $^1$H-NMR (CDCl$_3$): δ (ppm)=7.25–7.11 (m, 7H, arom), 7.01–6.91 (BB', 2H, arom), 4.39 (t, 2H, CH$_2$), 3.65 (s, 3H, CH$_3$), 3.02 (t, 2H, CH$_2$), 2.56 (quin, 2H, CH$_2$).

b) Methyl 2-(4-chlorophenyl)-1-(4-sulphamoylphenyl)-6,7-dihydro-5H-pyrrolizine-3-carboxylate Methyl 2-(4-chlorophenyl)-1-phenyl-6,7-dihydro-5H-pyrrolizine-3-carboxylate (0.87 g, 2.5 mmol) is dissolved in dichloroethane (10 ml) and the solution is cooled to 0–5° C. in an ice bath. A solution of chlorosulphonic acid (0.5 g, 5.7 mmol) in dichloroethane (5 ml) is slowly added dropwise (IT<10° C.), and the mixture is then stirred at RT for 12 h. A solution of NH$_3$ in dichloroethane saturated in the cold is added, and the mixture is stirred at RT for a further 12 h. The mixture is then treated with water (20 ml), and the organic phase is separated in a separating funnel. Solid which is insoluble in water is filtered off from the aqueous phase with suction and dried in vacuo. The dried solid substance is crystallized from MeOH: 0.5 g (47%); a 2nd crystal fraction crystallized from the mother liquor in the cold: 23% (0.25 g).

Y: 70.5% (0.75 g)+, C$_{21}$H$_{19}$ClN$_2$O$_4$S, MW=430.91; IR (NaCl): 1/λ (cm$^{-1}$)=3448, 3177, 1693, 1463, 1452, 1440, 1397, 1313, 1221, 1186, 1134, 1095, 1036, 1008; $^1$H-NMR (CD$_3$OD): δ (ppm)=7.63–7.59 (AA', 2H, arom), 7.26–7.10 (AA'BB', 4H, arom), 7.06–7.02 (BB', 2H, arom), 4.87 (s, SONH$_2$), 4.37 (t, 2H, CH$_2$), 3.62 (s, 3H, COOCH$_3$), 3.02 (t, 2H, CH$_2$), 2.56 (quin, 2H, CH$_2$).

EXAMPLE 20

4-[2-(4-Chlorophenyl)-6,7-dihydro-5H-pyrrolizin-1-yl]benzenesulphonamide a) Benzyl 2-(4-chlorophenyl)-1-phenyl-6,7-dihydro-5H-pyrrolizine-3-carboxylate 6-(4-Chlorophenyl)-7-phenyl-2,3-dihydro-1H-pyrrolizine (Example 17 a, 1.5 g, 5.1 mmol), dissolved in THF (10 ml), is treated with triethylamine (0.7 ml, 0.51 g, 5 mmol). A solution of diphosgene (0.5 g, 2.5 mmol), dissolved in THF (5 ml), is added dropwise to this solution at RT, and it is stirred for 8 h. Benzyl alcohol (abs., 0.52 ml, 0.54 g) and triethylamine (0.7 ml, 0.51 g, 5 mmol) are then added, and the mixture is stirred at RT for a further 48 h. The reaction mixture is partitioned between water (30 ml) and diethyl ether (60 ml), and the ether phase is washed with NaOH (5%, 20 ml). An oily residue is obtained from the THF/ether phase dried using $Na_2SO_4$ sicc. after the removal of the solvent in vacuo.

Y: 55% (1.2 g), $C_{27}H_{22}ClNO_2$, MW=427.93; IR (NaCl): $1/\lambda$ (cm$^{-1}$)=2956, 1685, 1600, 1515, 1465, 1305, 1224, 1133; $^1$H-NMR (CDCl$_3$): $\delta$ (ppm)=7.24–6.57 (m, 14H arom), 5.11 (s, CH$_2$), 4.443–4.36 (t, CH$_2$), 3.05–2.98 (t, CH$_2$), 2.61–2.50 (qu, CH$_2$).

b) 4-[2-(4-Chlorophenyl)-6,7-dihydro-5H-pyrrolizin-1-yl]benzenesulphonamide

Benzyl 2-(4-chlorophenyl)-1-phenyl-6,7-dihydro-5H-pyrrolizine-3-carboxylate (0.48 g, 1.1 mmol) is added to an initially introduced amount of chlorosulphonic acid (2.5 ml, 4.4 g, 38 mmol) which is maintained at −48° C. (>solidification point). After the removal of the cooling bath, the mixture is allowed to warm to RT with stirring; it is stirred here for a further 24 h. It is then treated with a saturated solution of NH$_3$ in CHCl$_3$ (30 ml), and the mixture is again stirred for 16 h. The deposited salts are taken up in water (30 ml) and the phase mixture is extracted with ethyl acetate (50 ml), dried (Na$_2$SO$_4$ sicc.) and concentrated to 10% of the starting volume. 110 mg (27%) of solid substance is crystallized from EA.

$C_{19}H_{17}ClN_2O_2S$, MW=372.88; IR (NaCl): $1/\lambda$ (cm$^{-1}$)= 3427, 2957, 2897, 1596, 1525, 1486, 1393, 1219, 1186, 1128, 1011, 835, 635; $^1$H-NMR (CDCl$_3$): $\delta$ (ppm)=7.7–7.66 (AA', 2H, arom), 7.20–7.10 (m, 7H, arom), 4.89 (s, 2H, SONH$_2$), 4.01 (t, 2H, CH$_2$), 2.935 (t, 2H, CH$_2$), 2.54 (quin, 2H, CH$_2$).

EXAMPLE 21

4-[1-(4-Chlorophenyl)-3-methyl-6,7-dihydro-5H-pyrrolizin-2-yl]benzenesulphonamide a) 2-(4-Chlorobenzyl)-1-pyrroline Magnesium turnings (4.04 g, 168 mmol) are introduced into diethyl ether abs. (10 ml), and the formation of the Grignard reagent is started with a crystal of iodine and 4-chlorobenzyl chloride (2.2 ml, 2.7 g, 16.8 mmol). The remaining amount of 4-chlorobenzyl chloride (19 ml, 24 g, 148.7 mmol), dissolved in diethyl ether abs. (150 ml), is added dropwise (45 min) such that the mixture boils vigorously. After addition is complete, the mixture is refluxed by heating for a further 1.5 h. A solution of 4-chlorobutyronitrile (16.6 g, 160 mmol) in diethyl ether abs. (150 ml) is added dropwise to the solution of the 4-chlorobenzyl Grignard reagent prepared in this way (45 min), the mixture is stirred for a further 45 min after the addition, toluene abs. (200 ml) is added and diethyl ether is distilled off over a bridge until a temperature of 95° C. is reached in the bottom (2.5 h). The mixture is cooled in an ice bath and dil. HCl (10%) is added at 25–30° C. until a pH of 2–3 is reached in the depositing aqueous phase. The toluene/ether phase is separated and extracted 3 times with HCl (10%, 150 ml). The collected HCl phase is washed again with toluene (100 ml) and then rendered alkaline (pH 9–10) with NaOH (32%). The depositing oily pyrroline phase is taken up in diethyl ether (300 ml), dried over K$_2$CO$_3$ and concentrated. The concentrated ether phase (to 50%-55% product content) is used without further purification.

Y: 14.1 g (21.6%); $^1$H-NMR (CDCl$_3$): $\delta$ (ppm)=7.25–7.09 (AA'BB', 4H, arom), (s, 2H, CH$_2$), 4.035 (t, CH$_2$), 2.965 (t, CH$_2$), 2.545 (quin, CH$_2$).

b) 7-(4-Chlorophenyl)-6-phenyl-2,3-dihydro-1H-pyrrolizine 2-(4-Chlorobenzyl)-1-pyrroline (9 g, 50% strength, 25 mmol), dissolved in MeOH (75 ml) is treated with phenacyl bromide (4.97 g, 25 mmol) and then with NaHCO$_3$ (2.5 g, 30 mmol) and stirred at RT for 16 h with exclusion of light. Precipitated crystallizate is filtered off with suction and washed with MeOH. 3.3 g (45%) of product are obtained after drying.

Y: 45% (3.3 g), $C_{19}H_{16}ClN$, MW=293.80; IR (NaCl): $1/\lambda$ (cm$^{-1}$)=3029, 2970, 2894, 1598, 1524, 1486, 1443, 1392, 1295, 1189, 1090; $^1$H-NMR (CDCl$_3$): $\delta$ (ppm)=7.25–7.09 (m, 9H, arom), 6.75 (s, 1H), 4.035 (t, CH$_2$), 2.965 (t, CH$_2$), 2.545 (quin, CH$_2$).

c) 2-[1-(4-Chlorophenyl)-2-phenyl-6,7-dihydro-5H-pyrrolizin-3-yl]acetic acid

Oxalyl dichloride (5.6 g, 0.044 mol) is added dropwise at 0–10° C. to an ice-cold solution of 7-(4-chlorophenyl)-6-phenyl-2,3-dihydro-1H-pyrrolizine (9.2 g, 0.031 mol) in THF (100 ml). After addition is complete, the mixture is stirred for 15 min and the excess of acid chloride is then cautiously decomposed (gas and foam formation!) with ice water (12 ml). Hydrazine (18 ml, 80%, about 0.3 mol) is added dropwise, the mixture is stirred for 30 min and diethylene glycol (36 ml) is poured in. THF and water are distilled off under atmospheric pressure at a bath temperature of 100–110° C. (foam formation at 105° C.!). The mixture is cooled to 60° C. and potassium hydroxide (15.7 g of KOH 85%, 0.238 mol) is added in portions and the temperature in the bottom is increased to 140° C. (foam formation!), and water, hydrazine and residual solvents are distilled off. This temperature is maintained in the bottom for 1 h and the mixture is allowed to cool. The mixture cooled to 60° C. is treated with water (200 ml) and acidified to pH 2–3 with conc. HCl in an ice bath (temp. <10° C.). The depositing carboxylic acid is extracted with ethyl acetate (300 ml), and the EA extract is washed with water until neutral, dried using Na$_2$SO$_4$ sicc. and concentrated in the presence of heat (45° C.) until the start of crystallization and placed in the cold. The crystal mass deposited at 5° C. is filtered off with suction and washed with cold ethyl acetate and dried.

Y: 6 g (55%), $C_{21}H_{18}ClNO_2$, MW=351.84; IR (NaCl): $1/\lambda$ (cm$^{-1}$)=3434, 2959, 2903, 1703, 1531, 1489, 1425, 1303, 1091, 834, 702, 515; $^1$H-NMR (CDCl$_3$): $\delta$ (ppm)= 7.33–6.96 (m, 9H, arom), 4.02 (t, 2H, CH$_2$), 3.62 (s, 2H, CH$_2$), 3.02 (t, 2H, CH$_2$), 2.56 (quin, 2H, CH$_2$).

d) 7-(4-Chlorophenyl)-5-methyl-6-phenyl-2,3-dihydro-1H-pyrrolizine

A flask, filled with crystalline solid substance of 2-[2-(4-chlorophenyl)-1-phenyl-6,7-dihydro-5H-pyrrolizin-3-yl]-2-acetic acid (1.5 g, 4.3 mmol), is heated at 180° C. in an oil bath until the release of CO$_2$ controlled by a gas bubble counter subsides (10–15 min). The residue cooled to 50° C. is stirred with diisopropyl ether (50 ml) until it has cooled to room temperature, then the undissolved crystals are filtered off with suction and the crude product is crystallized from diisopropyl ether.

1.1 g of cream-coloured, crystalline compound are obtained.

Y: 73% (1.1 g), $C_{20}H_{18}ClN$, MW=307.83; Mp.: 120.0° C.; IR (KBr): $1/\lambda$ (cm$^{-1}$)=3050, 2970, 2870, 1606, 1535, 1487, 1424, 1088, 1010, 829, 766, 701; $^1$H-NMR (CDCl$_3$): δ (ppm)=7.3–6.98 (m, 9H, arom), 3.94 (t, 2H, CH$_2$), 3.02 (t, 2H, CH$_2$), 2.54 (quin, 2H, CH$_2$), 2.24 (s, 3H, CH$_3$).

e) 4-[1-(4-Chlorophenly)-3-methyl-6,7-dihydro-5H-pyrrolizin-2-yl]benzenesulphonamide 7-(4-Chlorophenyl)-5-methyl-6-phenyl-2,3-dihydro-1H-pyrrolizine (5.4 g, 0.0175 mol) is added in portions (0.5 g) to the chlorosulphonic acid (13 g, 0.112 mol) cooled to 0° C. in the flask, and the mixture is stirred at RT for 18 h. The chlorosulphonic acid is cautiously destroyed with water (10 ml) while cooling in an ice bath and resultant sulphuric acid is diluted. Resultant sulphochloride is extracted with ethyl acetate (50 ml), and the extract is dried over Na$_2$SO$_4$ sicc. and concentrated. The residue remaining after the evaporation of the solvent in vacuo is treated with a solution of NH$_3$ in CHCl$_3$ (150 ml), which was obtained by passing in NH$_3$ at 0° C. until it was saturated. The mixture is stirred for 1 h, and then the ammonium salts crystallized from the reaction mixture are filtered off with suction. The filtrate is concentrated and the residue (5.4 g) is purified by CC (SiO$_2$/EA-n-hexane 6:4). After the removal of the solvent, 1.0 g (15%) of the pure substance is obtained from the product fractions.

Y: 15%=1.0 g (%), $C_{20}H_{19}ClN_2O_2S$, MW=386.90; IR (KBr): $1/\lambda$ (cm$^{-1}$)=3335, 3255, 1595, 1489, 1340, 1164, 835, 749, 547; $^1$H-NMR (CDCl$_3$): δ (ppm)=7.83–7.79 (d, 2H, arom), 7.28–6.95 (m, 6H, arom), 4.77 (s, 2H, NH$_2$), 3.99–3.92 (t, 2H, CH$_2$), 3.03–2.96 (t, 2H, CH$_2$), 2.63–2.49 (quin, 2H, CH$_2$), 2.26 (s, 3H, CH$_3$).

EXAMPLE 22

Ethyl 1-(4-chlorophenyl)-2-(4-sulphamoylphenyl)-6,7-dihydro-5H-pyrrolizine-3-carboxylate a) Ethyl 1-(4-chlorophenyl)-2-phenyl-6,7-dihydro-5H-pyrrolizine-3-carboxylate 7-(4-Chlorophenyl)-6-phenyl-2,3-dihydro-1H-pyrrolizine (Example 21 b, 1.5 g, 5.1 mmol), dissolved in THF (10 ml), is treated with triethylamine (0.7 ml, 0.51 g, 5 mmol). A solution of diphosgene (0.5 g, 2.5 mmol), dissolved in THF (5 ml), is added dropwise to this solution at RT, it is stirred for 12 h, ethanol (abs., 3 ml, 2.37 g, 51 mmol) and triethylamine (0.7 ml, 0.51 g, 5 mmol) are added, and the mixture is stirred at RT for a further 72 h. The reaction mixture is concentrated in vacuo, and the residue is crystallized from EtOH and dried.

Y: 81.5% (1.52 g), $C_{22}H_{20}ClNO_2$, MW=365; IR (NaCl): $1/\lambda$ (cm$^{-1}$)=2985, 2969, 1694, 1545, 1473, 1415, 1385, 1311, 1221, 1126, 1097; $^1$H-NMR (CDCl$_3$): δ (ppm)= 7.28–7.17 (m, 5H, arom), 7.14–6.91 (AA'BB', 4H, arom), 4.40 (t, 2H, CH$_2$), 4.10 (q., OCH$_2$), 3.01 (t, 2H, CH$_2$), 2.56 (quin, 2H, CH$_2$), 1.055 (t, 3H, CH$_3$).

b) Ethyl 1-(4-chlorophenyl)-2-(4-sulphamoylphenyl)-6,7-dihydro-5H-pyrrolizine-3-carboxylate Ethyl 1-(4-chlorophenyl)-2-phenyl-6,7-dihydro-5H-pyrrolizine-3-carboxylate (1.6 g, 4.4 mmol) is suspended in chlorosulphonic acid (8 ml, 14.2 g, 120 mmol), which has previously been adjusted to a temperature of −10° C., and the mixture is stirred at RT for 16 h; it is then warmed briefly (30 min, 60° C.) and subsequently cooled again. The mixture is treated with ice (20 ml) and extracted with CHCl$_3$ (20 ml). The CHCl$_3$ phase dried over Na$_2$SO$_4$ sicc. is treated with a solution of NH$_3$ in CHCl$_3$ (20 ml) saturated in the cold, and the mixture is stirred at RT for a further 12 h. The insoluble substance at the bottom is then filtered off with suction. This residue is heated in 120 ml of ethanol, and undissolved salts are filtered off with suction. On concentration of the EtOH solution to 20% of the starting volume, 1.5 g of product crystallize out. After further concentration, an additional 170 mg are obtained in the cold.

Y: 85.3% (1.67 g), $C_{22}H_{21}ClN_2O_4S$, MW=444.94; Mp: dec from 110°; IR (NaCl): $1/\lambda$ (cm$^{-1}$)=3265, 2981, 1688, 1542, 1464, 1419, 1382, 1312, 1227, 1163, 1098; $^1$H-NMR (CDCl$_3$): δ (ppm)=7.73–7.68 (AA', 2H, arom), 7.27–7.23 (AA', 2H, arom), 7.04–7.00 (BB', 2H, arom), 6.81–677 (BB', 2H, arom), 4.31 (t, 2H, CH$_2$), 4.02 (q, 2H, OCH$_2$), 2.94–2.83 (t, 4H, CH$_2$+SO$_2$NH$_2$), 2.48 (quin, 2H, CH$_2$), 0.99 (t, 3H, CH$_3$).

EXAMPLE 23

Methyl 1-(4-chlorophenyl)-2-(4-sulphamoylphenyl)-6,7-dihydro-5H-pyrrolizine-3-carboxylate a) Methyl 1-(4-chlorophenyl)-2-phenyl-6,7-dihydro-5H-pyrrolizine-3-carboxylate 7-(4-Chlorophenyl)-6-phenyl-2,3-dihydro-1H-pyrrolizine (Example 21 b, 4.0 g, 13.6 mmol), dissolved in THF (25 ml) is treated with triethylamine (2.0 ml, 1.5 g, 15 mmol). A solution of diphosgene (1.5 g, 7.5 mmol), dissolved in THF (15 ml), is added dropwise to this solution at RT, and it is stirred for 12 h. Methanol (abs., 8.0 ml, 6.3 g, 200 mmol) and triethylamine (2.0 ml, 1.5 g, 15 mmol) are then added, and the mixture is stirred at RT for a further 48 h. The reaction mixture is concentrated in vacuo, ammonium salts are taken up in water (10 ml), and the residue which remains is filtered off with suction and dried. 4.7 g (98.3%) of crude product are obtained.

Y: 98.3% (4.7 g), $C_{21}H_{18}ClNO_2$, MW=351.84; Mp: 147–149° C.; IR (NaCl): $1/\lambda$ (cm$^{-1}$)=2951, 1703, 1545, 1468, 1435, 1405, 1394, 1311, 1218, 1162, 1094, 833, 727, 696; $^1$H-NMR (CDCl$_3$): δ (ppm)=7.25–717 (m, 5H, arom), 7.14–6.89 (AA'BB', 4H, arom), 4.40 (t, 2H, CH$_2$), 3.63 (s, 3H, COOCH$_3$), 3.00 (t, 2H, CH$_2$), 2.55 (quin, 2H, CH$_2$).

b) Methyl 1-(4-chlorophenyl)-2-(4-sulphamoylphenyl)-6,7-dihydro-5H-pyrrolizine-3-carboxylate Methyl 2-(4-chlorophenyl)-1-phenyl-6,7-dihydro-5H-pyrrolizine-3-carboxylate (4.0 g, 11.4 mmol) is dissolved in dichloroethane (40 ml), and the solution is cooled to 0–5° C. in an ice bath. A solution of chlorosulphonic acid (2.0 g, 17.3 mmol) in dichloroethane (20 ml) is slowly added dropwise to this (IT<10° C., 15 min) and the mixture is then stirred at RT for 12 h. A solution of NH$_3$ in dichloroethane (40 ml) saturated in the cold is added, and the mixture is stirred at RT for a further 12 h. It is then treated (pH 9) with water (20 ml), and the organic phase is separated in a separating funnel. Solid insoluble in water is filtered off from the aqueous phase with suction and dried in vacuo. The dried solid substance is crystallized from MeOH: 0.76 g (product A).

The dichloroethane phase is dried over Na$_2$SO$_4$ sicc. and concentrated in vacuo; a residue of 1.6 g remains (product B).

Product B:

Y: 32.6% (1.6 g), $C_{21}H_{19}ClN_2O_4S$, MW=430.91; Mp: dec 140° C.; IR (NaCl): $1/\lambda$ (cm$^{-1}$)=3022, 2951, 2886, 1708, 1596, 1545, 1488, 1459, 1399, 1220, 1121, 1098, 833; $^1$H-NMR (CD$_3$OD): δ (ppm)=7.29–7.17 (AA'+AA', 4H, arom), 7.14–7.10 (BB', 2H, arom), 6.94–6.89 (BB', 2H, arom), 4.39 (t, 2H, CH$_2$), 3.63 (s, 3H, COOCH$_3$), 3.00 (t, 2H, CH$_2$), 2.56 (quin, 2H, CH$_2$).

Product A:

is identical with product from Example 24

EXAMPLE 24

4-[1-(4-Chlorophenyl)-6,7-dihydro-5H-pyrrolizin-2-yl] benzenesulphonamide a) tert-Butyl 1-(4-chlorophenyl)-2-phenyl-6,7-dihydro-5H-pyrrolizine-3-carboxylate 7-(4-Chlorophenyl)-6-phenyl-2,3-dihydro-1H-pyrrolizine (Example 21 b, 0.75 g, 2.5 mmol), dissolved in THF (10 ml), is treated with triethylamine (0.3 ml, 0.25 g, 2.5 mmol). A solution of diphosgene (0.25 g, 1.25 mmol), dissolved in THF (5 ml), is added dropwise to this solution at RT, and it is stirred for 18 h. tert-Butyl alcohol (abs., 1.0 ml, 0.786 g, 10 mmol) and triethylamine (0.7 ml, 0.51 g, 5 mmol) are then added, and the mixture is stirred at RT for a further 48 h. The reaction mixture is partitioned between water (30 ml) and CHCl$_3$ (60 ml), and the ether phase is washed with Na$_2$CO$_3$ solution (5%, 20 ml). After removal of the solvent in vacuo, an oily residue (0.7 g), which by TLC (SiO$_2$, hexane/CH$_2$Cl$_2$ 1:1) still contains starting material (Rf 0.75) in addition to product (Rf 0.3), is obtained from the THF/CHCl$_3$ phase dried using Na$_2$SO$_4$ sicc. The residue is purified by CC (SiO$_2$, hexane/CH$_2$Cl$_2$ 1:1); 190 mg of the pure ester are obtained.

Y: 20% (0.19 g), $C_{24}H_{24}ClNO_2$, MW=393.92; $^1$H-NMR (CDCl$_3$): δ (ppm)=7.27–7.13 (m, 5H, arom), 7.12–6.89 (qu, 4H, arom), 4.42–4.35 (t, 2H, CH$_2$), 3.02–2.94 (t, 2H, CH$_2$), 2.57–2.49 (qui, 2H, CH$_2$).

b) 4-[1-(4-Chlorophenyl)-6,7-dihydro-5H-pyrrolizin-2-yl] benzenesulphonamide tert-Butyl 1-(4-chlorophenyl)-2-phenyl-6,7-dihydro-5H-pyrrolizine-3-carboxylate (190 mg, 0.5 mmol) is taken up in CHCl$_3$ (10 ml), the solution is cooled to 0–5° C. in an ice bath, and a solution of chlorosulphonic acid (1 ml, 1.75 g, 15 mmol) in CHCl$_3$ (20 ml) is then slowly added dropwise (IT<10° C., 15 min). The mixture is then stirred at RT for 12 h, a solution of NH$_3$ in dichloroethane (40 ml) saturated in the cold is added and it is stirred at RT for a further 12 h. It is then treated with ice water (5 ml), and the phase mixture is sucked through a G3 frit. The CHCl$_3$ phase is separated from the now clear aqueous phase in a separating funnel. The filter residue is washed with a little water and CHCl$_3$ and dried in vacuo. The dried solid substance is crystallized from MeOH: 0.13 g (70%).

Y: 70% (130 mg), $C_{19}H_{17}ClN_2O_2S$, MW=372.88; IR (NaCl): $1/\lambda$ (cm$^{-1}$)=3432, 3178, 3055, 1596, 1547, 1489, 1445, 1426, 1384, 1288, 1185, 1091, 1042, 833, 731, 721, 637; $^1$H-NMR (DMSO-d6): δ (ppm)=7.24–717 (AA'+AA'+CH, 5H, arom), 7.09–6.89 (BB'+BB', 4H, arom), 4.87 (s, 2H, SO$_2$NH$_2$), 4.29 (t, 2H, CH$_2$), 2.96 (t, 2H, CH$_2$), 2.52 (quin, 2H, CH$_2$).

The compounds of Examples 25–29 are prepared according to analogous procedures:

spectroscopic data for compounds 25–29 are listed in the figures.

EXAMPLE 30

4-(3-Methyl-6,7-dihydro-5H-pyrrolizin-1-yl) benzenesulphonamide a) 7-Phenyl-2,3-dihydro-1H-pyrrolizine 2-Benzyl-1-pyrroline (Example 1b, 85%, 74 g, 0.395 mol), dissolved in MeOH (360 ml), is treated with NaHCO$_3$ (38 g, 0.45 mol), and the mixture is cooled to 5° C. A solution of chloroacetaldehyde (45% strength in water, 68 g, 0.4 mol), dissolved in MeOH (100 ml) is added dropwise to the solution at this temperature, and the mixture is stirred for 18 h with exclusion of light.

The reaction mixture with the substance at the bottom is partitioned between semi-saturated NaCl solution (900 ml) and ethyl acetate (900 ml), the ethyl acetate phase is washed with saturated NaCl solution (300 ml) and dried using Na$_2$SO$_4$ sicc., and the solvent is removed in vacuo. The residue (82 g) has the purity necessary for the further reactions (TLC SiO$_2$, hexane/diethyl ether 1:1, Rf 0.65).

Y: 112% (82 g), $C_{13}H_{13}N$, MW=183.26; Mp: 60.4° C.; IR (NaCl): $1/\lambda$ (cm$^{-1}$)=2360, 1601, 1551, 1498, 1440, 1295, 1245, 1072, 958, 903, 764, 711, 690, 654, 609; $^1$H-NMR (CDCl$_3$): δ (ppm)=7.50–7.07 (m, 5H, arom), 6.64 and 6.53 (2×CH), 4.00 (t, 2H, CH$_2$), 3.09 (t, 2H, CH$_2$), 2.62–2.52 (q, 2H, CH$_2$); $^{13}$C-NMR (CDCl$_3$): δ (ppm)=136.6, 134.2, 128.4, 124.9, 124.3, 115.0, 114.3, 110.0, 46.1, 27.8, 25.2.

b) Ethyl oxo-(1-phenyl-6,7-dihydro-5H-pyrrolizin-3-yl) acetate

7-Phenyl-2,3-dihydro-1H-pyrrolizine (crude, 82 g, about 0.4 mol) is dissolved in THF (400 ml), the solution is cooled to 0–5° C. in an ice bath, then a solution of ethyl oxalyl chloride (50 ml, 61.1 g, 0.448 mol) in THF (200 ml) is added dropwise in the course of 30 min (IT<10° C., 15 min). The mixture is then stirred at this temperature for a further 1 h and at RT for 1 h. It is then treated with Na$_2$CO$_3$ solution (saturated, 300 ml) with ice-cooling and extracted 3 times with ethyl acetate (300 ml). The organic phase is washed in a separating funnel with NaCl solution (saturated, 300 ml) and separated from the aqueous phase. The ethyl acetate-THF phase is dried using Na$_2$SO$_4$ sicc., and the solvent is evaporated in vacuo. The dried residue (99 g) in CH$_2$Cl$_2$ is purified by CC (SiO$_2$, ether): 46.4 g of pure substance: (41.1%).

Y over a and b: 41% (46.4 g), $C_{17}H_{17}NO_3$, MW=283.33; Mp: 101.8° C.; IR (NaCl): $1/\lambda$ (cm$^{-1}$)=1734, 1630, 1450, 1428, 1217, 1148, 1046, 1006, 763, 696 $^1$H-NMR (DMSO-d6): δ (ppm)=7.63 (s, 1H, CH), 7.51–7.22 (m, 5H, arom), 4.46–4.35 (t, 2H, CH$_3$ and q, 2H, CH$_2$), 3.11 (t, 2H, CH$_2$), 2.62 (quin, 2H, CH$_2$), 1.43 (t, 3H, CH$_3$).

GC-MS: m/z (rel. int. [%]=284 (06); 283 (M$^{+*}$, 30); 211 (20); 210 ((M-COOEt$^*$)$^+$; 100); 167 (05); 154 (05); 153 (05); 141 (06); 127 (05); 115 (05).

c) 1-Phenyl-6,7-dihydro-5H-pyrrolizin-3-yl acetic acid

Ethyl oxo-(1-phenyl-6,7-dihydro-5H-pyrrolizin-3-yl) acetate (46 g, 0.163 mol) is dissolved in diethylene glycol-THF (1:1, 750 ml), hydrazine hydrate (80% strength, 110 ml, 113 g, 1.8 mol) is added, the mixture is adjusted to a temperature of 60° C. in an oil bath, and the mixture is stirred at this temperature for 1.5 h. THF is distilled off (350 ml) and the bottom temperature is increased to 100° C. stepwise (60 min). The mixture is allowed to cool to 60° C., KOH platelets (85%, 173 g, 2.62 mol) are added to the mixture, the mixture temperature is increased to 120° C., and it is subsequently stirred at this temperature for a further 2 h and then cooled. When 50° C. is reached, it is treated with ice water (1.2 l) and extracted 3 times with ethyl acetate (900 ml). The aqueous phase is acidified to pH 3 using HCl (20% strength), extracted 3 times with ethyl acetate (900 ml) and the organic phase is washed in a separating funnel with NaCl solution (saturated, 300 ml). The ethyl acetate phase is dried using $Na_2SO_4$ sicc., and the solvent is evaporated in vacuo. The residue crystallizes from hexane-ether 1:1:10.7 g (27.2%). After concentrating the mother liquor and taking up the residue in ethyl acetate, the solution is washed with water, dried over $Na_2SO_4$ sicc. and concentrated again: a further 11.3 g of product remain.

Y: 56% (22 g), $C_{15}H_{15}NO_2$, MW=241.29; Mp: 108.8° C.; IR (NaCl): $1/\lambda$ $(cm^{-1})$=2891, 1708, 1604, 1419, 1398, 1296, 1235, 758, 696; $^1$H-NMR (DMSO-d6): $\delta$ (ppm)=7.46–7.09 (m, 5H, arom), 6.40 (s, 1H, CH), 3.96–3.89 (t, 2H, $CH_2$), 3.11–3.04 (t, 2H, $CH_2$), 2.60–2.56 (q, 2H, $CH_2$); $^{13}$C-NMR (DMSO-d6): $\delta$ (ppm)=171.9, 136.6, 133.1, 128.6, 124.1, 123.9, 120.9, 113.5, 108.6, 44.1, 32.4, 27.1, 25.4.

c) 5-Methyl-7-phenyl-2,3-dihydro-1H-pyrrolizine

1-Phenyl-6,7-dihydro-5H-pyrrolizin-3-yl)acetic acid (21 g, 0.087 mol) is filled into a flask under protective gas, and this flask is immersed in an oil bath maintained at a temperature of 180° C. The mixture is treated at 180° C. until the evolution of gas subsides (45 min) and a TLC sample ($SiO_2$, ether-hexane 1:1) indicates complete conversion. The cooled melt is dissolved in ethyl acetate (300 ml) in the presence of heat, and washed 3 times with $Na_2CO_3$ solution (10%, 100 ml), once with NaCl (50 ml) and once with water (50 ml). The ethyl acetate phase is dried over $Na_2SO_4$ sicc. and concentrated: 16.1 g of yellow-brown solid (93.8%) remain.

Y: 93.8% (16.1 g), $C_{14}H_{15}N$, MW=197.28; Mp: 58.9° C.; IR (NaCl): $1/\lambda$ $(cm^{-1})$=2919, 2887, 1601, 1521, 1418, 1405, 1300, 1211, 1066, 750, 691, 653, 503; $^1$H-NMR (CDCl$_3$): $\delta$ (ppm)=7.45–7.08 (m, 5H, arom), 6.20 (1H, CH), 3.87–3.80 (t, 2H, $CH_2$), 3.10–3.03 (t, 2H, $CH_2$), 2.58–2.51 (t, 2H, $CH_2$), 2.23 (s, 3H, $CH_3$); $^{13}$C-NMR (CDCl$_3$): $\delta$ (ppm)= 136.8, 132.2, 128.4, 124.9, 124.1, 123.9, 114.4, 107.1, 44.1, 27.7, 25.7, 11.9.

d) 4-(3-Methyl-6,7-dihydro-5H-pyrrolizin-1-yl) benzenesulphonamide

5-Methyl-7-phenyl-2,3-dihydro-1H-pyrrolizine (370 mg, 1.9 mmol) is suspended in chlorosulphonic acid (1.5 ml, 2.62 g, 22.5 mmol), which has been cooled to −101C, with exclusion of moisture. The mixture is subsequently stirred at RT for 72 h, then treated cautiously with ice (10 g), extracted with chloroform (3×20 ml), and the combined chloroform extracts are washed with cold NaCl solution. The washed CHCl$_3$ extract is dried over $Na_2SO_4$ sicc.; then $NH_3$ from a pressurized container is passed into the filtered CHCl$_3$ solution of the sulphochloride. The suspension saturated with $NH_3$ is stirred for a further 1 h, then treated with ice water (15 ml) and the phase mixture is filtered off with suction through a G3 frit. The CHCl$_3$ phase is separated in a separating funnel from the now clear aqueous phase, the latter is extracted a further two times with CHCl$_3$ (150 ml), and the CHCl$_3$ phases are combined, dried over $Na_2SO_4$ sicc. and concentrated in vacuo. The solid substance (270 mg, 53%) remaining after stripping off the solvent is crystallized from EtOH 60%: 75 mg (14.2%).

Y: 53% (270 mg), $C_{14}H_{16}N_2O_2S$, MW=276.36; Mp: 198–207° C.; IR (NaCl): $1/\lambda$ $(cm^{-1})$=3348, 3253, 1596, 1528, 1430, 1327, 1302, 1151, 1095, 836, 543, 412; $^1$H-NMR (CDCl$_3$): $\delta$ (ppm)=7.72–7.49 (AA'BB', 4H, arom), 7.20 ($NH_2$), 6.23 (s, 11H, CH), 3.84 (t, 2H, $CH_2$), 3.03 (t, 2H, $CH_2$), 2.49 (quin, 2H, $CH_2$), 2.17 (s, 3H, $CH_3$); $^{13}$C-NMR (CDCl$_3$): $\delta$ (ppm)=134, 127.1, 126.5, 126.1, 125, 124.2, 113, 107.1, 44.0, 27.3, 25.8, 11.6.

The compound of Example 33 is synthesized from 2-benzyl-1-pyrroline (Example 1b) and α-bromo-tert-butyl methyl ketone according to the reaction sequence described for Example 30; the introduction of the 5-methyl group takes place via conversion of the 6-tert-butyl-7-phenyl-2,3-dihydro-1H-pyrrolizine into the ethyl 5-oxoacetate and its reduction to the acetic acid, which decarboxylates at elevated temperature.

The compounds of Examples 31 and 32 are prepared from 2-benzyl-1-pyrroline (Example 1b) and the haloketones 2-chlorobutanone (Example 31), or 2-chlorocyclohexanone (Example 32) analogously to the reaction sequence of method A of Example 34 described below. The substituents in positions 5 and 6 are introduced via an appropriate bromoketone (R2—CO—CHBr—R3).

EXAMPLE 34

4-(3-Trifluoromethyl-6,7-dihydro-5H-pyrrolizin-1-yl) benzenesulphonamide a) 5-Trifluoromethyl-7-phenyl-2,3-dihydro-1H-pyrrolizine Method A:

2-Benzyl-1-pyrroline (Example 1b, 85%, 4.4 g, 24 mmol) and 1-bromo-3,3,3-trifluoroacetone (3.82 g, 20 mmol) are mixed with one another in a 25 ml flask (exothermic), and the mixture is then stirred at 80° C. for 4 h. Two isomeric products are formed in the ratio 0.8:1 (TLC: $SiO_2$—hexane/ ether 8:2, Rf 0.6+Rf 0.3). The mixture is treated with water (10 ml) and acidified with HCl (10%, 5 ml); it is extracted 3 times with ethyl acetate (100 ml). The ethyl acetate phase is dried over $Na_2SO_4$ sicc. and concentrated. The residue (2.0 g) is purified by CC ($SiO_2$, n-hexane/ether 8:2):

TY: 1.28 g (25%).

Method B:

2-Benzyl-1-pyrroline (Example 1 b, 85%, 6.3 g, 34 mmol), dissolved in methanol (60 ml), 1-bromo-3,3,3-trifluoroacetone (3.82 g, 20 mmol) and $NaHCO_3$ (1.85 g, 22 mmol) are mixed with one another in a 100 ml flask, and the mixture is then stirred at RT for 88 h. Two isomeric products are formed in the ratio 2:1 (TLC: $SiO_2$-hexane/ether 8:2, Rf 0.6+Rf 0.3). The mixture is treated with water (50 ml) and acidified (pH 3–4) with HCl (10%); it is extracted 3 times with diethyl ether (150 ml). The ether phase is dried over $Na_2SO_4$ sicc. and concentrated. The residue (7.1 g) is purified by CC ($SiO_2$, n-hexane/ether 8:2):

TY: 3.05 g (54%).

Fractions 1–16:6-Trifluoromethyl-7-phenyl-2,3-dihydro-1H-pyrrolizine;

Y: 36% (2.0 g), $C_{14}H_{12}F_3N$, MW=251.25; Mp: 67.8° C.; IR (NaCl): $1/\lambda$ $(cm^{-1})$=3446, 2922, 2362, 1603, 1565, 1484, 1450, 1375, 1266, 1208, 1143, 1098, 758, 690; $^1$H-NMR (CDCl$_3$): δ (ppm)=7.38–7.08 (5H, arom), 6.78 (s, 1H, CH), 4.02–3.95 (t, 2H, CH$_2$), 3.02–2.95 (t, 2H, CH$_2$), 2.59–2.48 (q, 2H, CH$_2$); $^{13}$C-NMR (CDCl$_3$): δ (ppm)=137, 135.2, 128.7, 125.3, 125.2, 124.2, 119, 115.6, 111.8, 46.0, 27.4, 25.2.

Fraction 18–24: Mixed Fraction.

Fraction 26–56:5-Trifluoromethyl-7-phenyl-2,3-dihydro-1H-pyrrolizine, 520 mg;

Y: 18% (1.0 g), C$_{14}$H$_{12}$F$_3$N, MW=251.25; Mp: 61.60° C.; IR (NaCl): 1/λ (cm$^{-1}$)=2906, 2360, 1605, 1531, 1458, 1298, 1196, 1138, 1109, 1084, 971, 778, 765, 702; $^1$H-NMR (CDCl$_3$): δ (ppm)=7.44–7.23 (5H, arom), 7.00 (s, 1H, CH), 4.03–3.96 (t, 2H, CH$_2$), 2.96–2.88 (t, 2H, CH$_2$), 2.55–2.48 (q, 2H, CH$_2$); $^{13}$C-NMR (CDCl$_3$): δ (ppm)=136.8, 134.6, 132.0, 128.3, 128.2, 126.6, 126.0, 121.3, 115, 46.7, 27.5, 24.3.

b) 4-(3-Trifluoromethyl-6,7-dihydro-5H-pyrrolizin-1-yl)benzenesulphonamide

5-Trifluoromethyl-7-phenyl-2,3-dihydro-1H-pyrrolizine (750 mg, 3 mmol) is suspended in chlorosulphonic acid (10 ml, 17.5 g, 150 mmol) with exclusion of moisture. The mixture is then stirred at RT for 16 h. It is cautiously treated with ice (10 g) with ice-cooling, extracted with chloroform (3×30 ml) and the combined chloroform extracts are washed with cold NaCl solution. The washed CHCl$_3$ extract is dried over Na$_2$SO$_4$ sicc., and the filtered CHCl$_3$ solution of the sulphochloride is then cooled to 5° C. NH$_3$ is passed in from a pressurized container for 1 h. The NH$_3$-saturated suspension is stirred for a further 2 h and then treated with ice water (15 ml). The CHCl$_3$ phase is separated in a separating funnel from the aqueous phase, the latter is extracted a further two times with CHCl$_3$ (150 ml), and the CHCl$_3$ phases are combined, washed with water (20 ml), dried over Na$_2$SO$_4$ sicc. and concentrated in vacuo. The solid substance remaining after stripping off the solvent (0.5 g, 50%, concentration 90%) is crystallized from ethyl acetate: 0.2 g (concentration 98%).

Y: 45% (0.5 g, 90% strength), C$_{14}$H$_{13}$F$_3$N$_2$O$_2$S, MW=330.33; Mp: 153.5° C.; IR (NaCl): 1/λ (cm$^{-1}$) 3388, 3282, 1594, 1536, 1296, 1198, 1149, 1112, 1091, 1079, 796, 598; $^1$H-NMR (CDCl$_3$): δ (ppm)=7.95–7.44 (AA'BB'+br, 6H, arom +NH$_2$), 7.04 (s, 1H, CH), 4.03 (t, 2H, CH$_2$), 2.95 (t, 2H, CH$_2$), 2.57 (quin, 2H, CH$_2$); $^{13}$C-NMR (CDCl$_3$): δ (ppm)=142.9, 135.5, 131.8, 128.7, 128.3, 126.1, 125.6, 123.5, 115.3, 46.7, 27.3, 24.1.

EXAMPLE 35

4-(2-Isobutyl-3-methyl-6,7-dihydro-51H-pyrrolizin-1-yl)benzenesulphonamide a) 2-Methyl-1-(3-methyl-1-phenyl-6,7-dihydro-5H-pyrrolizin-2-yl)propan-1-one 5-Methyl-7-phenyl-2,3-dihydro-1H-pyrrolizine (Example 30 c, 7.8 g, 0.039 mol), dissolved in dichloroethane (140 ml) is treated at RT with isobutyryl chloride (4.6 ml, 4.8 g, 0.043 mol), and tin tetrachloride (5.3 ml, 11.8 g, 0.045 mol) in dichloroethane (30 ml) is subsequently added dropwise.

The mixture warms to 35° C. and is refluxed for 2 h at 73° C. It is then poured onto ice, rendered alkaline with NaOH (10%, 200 ml) and the organic phase is separated in a separating funnel. The alkali phase is extracted a further two times with dichloromethane (400 ml), which is added to the dichloroethane phase. This extract is dried over Na$_2$SO$_4$ sicc. and evaporated to dryness in vacuo. The residue (11.3 g) is washed with a little diisopropyl ether and the crystals (7.56 g, 72.5%) are filtered off with suction and dried.

Y: 72.5% (7.56 g), C$_{18}$H$_{21}$NO, MW=267.37; Mp: 158.7° C.; IR (NaCl): 1/λ (cm$^{-1}$)=2958, 1648, 1599, 1518, 1421, 1407, 1115, 977, 702; $^1$H-NMR (CDCl$_3$): δ (ppm)= 7.35–7.22 (m, 5H, arom), 3.91 (t, 2H, CH$_2$), 2.84 (t, 2H, CH$_2$), 2.70 (sept., 1H, C$\underline{H}$(CH$_3$)$_2$), 2.52–2.40 (quin, 2H, CH$_2$), 2.39 (s, 3H, CH$_3$), 0.925 (d, 6H, CH(C$\underline{H_3}$)$_2$); $^{13}$C-NMR (CDCl$_3$): δ (ppm)=205.2, 136.8, 133.3, 130.0, 128.9, 128.1, 125.8, 123.0, 116.0, 44.5, 38.1, 26.9, 23.8, 19.1, 12.1.

b) 6-Isobutyl-5-methyl-7-phenyl-2,3-dihydro-1H-pyrrolizine

A solution of 2-methyl-1-(3-methyl-1-phenyl-6,7-dihydro-5H-pyrrolizin-2-yl)-propan-1-one (7.5 g, 28 mmol) in CH$_2$Cl$_2$ (140 ml) is treated successively with NaCNBH$_3$ (7.4 g, 112 mmol) and ZnI$_2$ (12.5 g, 40 mmol) and the mixture is stirred at RT for 2 h (TLC: SiO$_2$/diethyl ether; starting material Rf 0.75; product Rf 8.8). The mixture is covered with a layer of H3PO4 (8%, 200 ml) with ice cooling and stirred for 16 h. The CH$_2$Cl$_2$ phase is separated and washed with water (50 ml), dried over Na$_2$SO$_4$ sicc. and concentrated in vacuo. The residue (7.5 g, 106%) is recrystallized from MeOH.

Y: 64.4% (4.5 g), C$_{18}$H$_{23}$N, MW=253.39; Mp: 95.4° C.; IR (NaCl): 1/λ (cm$^{-1}$)=2916, 2861, 1599, 1527, 1453, 1421, 1305, 760, 698; $^1$H-NMR (CDCl$_3$): δ (ppm)=7.35–7.23 (m, 5H, arom), 3.87 (t, 2H, CH$_2$), 2.94 (t, 2H, CH$_2$), 2.52–2.41 (quin +d, 4H, CH$_2$+CH$_2$CH), 2.17 (s, 3H, CH$_3$), 1.62 (m., 1H, CH$_2$C$\underline{H}$(CH$_3$)$_2$), 0.795 (d, 6H, CH(C$\underline{H_3}$)$_2$); $^{13}$C-NMR (CDCl$_3$): δ (ppm)=137.9, 132.0, 128.1, 128.1, 124.5, 120.4, 120.4, 114.7, 44.4, 34.5, 30.3, 27.0, 24.7, 22.6, 10.4.

c) 4-(2-Isobutyl-3-methyl-6,7-dihydro-5H-pyrrolizin-1-yl)benzenesulphonamide

6-Isobutyl-5-methyl-7-phenyl-2,3-dihydro-1H-pyrrolizine (4.0 g, 16 mmol) is dissolved in CHCl$_3$ abs. (20 ml), the solution is cooled to 5° C. and chlorosulphonic acid (10 ml, 17.5 g, 150 mmol) is slowly added dropwise. The mixture is heated for 2.5 h (5 8–61° C.) (TLC: SiO$_2$, ether-hexane 1:1, starting material Rf 0.9, chlorosulphonic acid Rf 0.8). The reaction mixture is quenched on ice (100 ml) and taken up in CHCl$_3$ (120 ml). The ice-water phase is extracted 3 times with CHCl$_3$ (120 ml), and the collected CHCl$_3$ solution is washed (100 ml of saturated NaCl solution), dried (Na$_2$SO$_4$ sicc.) and concentrated (residue: 7.2 g). The chlorosulphonation product (7.2 g) is dissolved in THF abs., and concentrated NH$_4$OH (25% strength, 4 ml) is slowly added dropwise. The mixture is stirred at RT for 16 h, treated with semi-concentrated NaCl solution (60 ml) and extracted 3 times with ethyl acetate (150 ml). The washed (40 ml of saturated NaCl solution) ethyl acetate phase is dried (Na$_2$SO$_4$ sicc.) and concentrated. The residue (5.0 g, concentration 83% according to HPLC) is digested with ether (10 ml) at RT (2.76 g, 51%, concentration 94%) and subsequently crystallized from ethanol (20 ml) and dried:

Y: 34,4%, (1.83 g, 99.7% strength), C$_{18}$H$_{24}$N$_2$O$_2$S, MW=332.47; Mp: 197.1° C.; IR (NaCl): 1/λ (cm$^{-1}$)=3337, 3235, 2948, 1595, 1332, 1161, 1093, 546; $^1$H-NMR (DMSO-d6): δ (ppm)=7.74–7.42 (m, 5H, arom), 7.24 (NH$_2$), 3.83 (t, 2H, CH$_2$), 2.87 (t, 2H, CH$_2$), 2.41–2.37 (quin +d, 4H, CH$_2$+CH$_2$CH), 2.09 (s, 3H, CH$_3$), 1.62 (m., 1H, CH$_2$CH(CH$_3$)$_2$), 0.735 (d, 6H, CH(CH$_3$)$_2$); $^{13}$C-NMR (DMSO-d6): δ (ppm)=141.7, 139.3, 133.1, 126.8, 125.8, 120.7, 119.1, 112.4, 44.2, 40.2, 34.3, 29.6, 26.5, 24.7, 22.4, 10.1.

The compounds of Examples 36–38 are prepared according to analogous procedures:

spectroscopic data for compounds 36–38 are listed in the figures.

EXAMPLE 39

4-[2-(Perfluoroisopropyl)-3-methyl-6,7-dihydro-5H-pyrrolizin-1-yl]benzenesulphonamide a) 2,2,2-Trifluoro-1-(3-methyl-1-phenol-6,7-dihydro-5H-pyrrolizin-2-yl)ethan-1-one 5-Methyl-7-phenyl-2,3-dihydro-1H-pyrrolizine (Example 30 c, 90%, 2.2 g, 0.01 mol), dissolved in dichloromethane (30 ml), is treated at RT with trifluoroacetic anhydride (1.4 ml, 2.14 g, 0.01 mol) and zinc chloride (1.36 g, 0.01 mol). The mixture is stirred at RT for 2 h, after which a TLC sample (SiO$_2$, hexane-ether 1:1, starting material Rf 0.8, main product Rf 0.4, by-product Rf 0.6) indicates complete reaction. The mixture is then treated with water, rendered alkaline with NaOH (10%, 200 ml) and extracted a further 2 times with CH$_2$Cl$_2$ (50 ml). The collected organic phases are combined, dried over Na$_2$SO$_4$ sicc. and evaporated to dryness in vacuo.

The residue is purified by means of CC (SiO$_2$, 200 g, hexane-ether 1:1): first 0.34 g of the by-product fraction, then 1.3 g (44.4% yield) of the desired compound are obtained.

Y: 44.4% (13 g); C$_{16}$H$_{14}$F$_3$NO, MW=293.29; Mp.: 111.4° C., IR (NaCl): 1/λ (cm$^{-1}$)=1662, 1601, 1446, 1423, 1383, 1236, 1194, 1124, 1080, 974, 759, 706, 698; $^1$H-NMR (CDCl$_3$): δ (ppm)=7.37–7.21 (m, 5H, arom), 3.95 (t, 2H, CH$_2$), 2.84 (t, 2H, CH$_2$), 2.52 (quin, 2H, CH$_2$), 2.45 (s, 3H, CH$_3$); GC-MS (70 eV): m/z (rel. int. [%]=293 (59); 224 (100); 207 (20); 225 (17); 294 (10); 127 (08); 167 (06); 194 (05).

b) 1,1,1,3,3,3-Hexafluoro-2-(3-methyl-1-phenyl-6,7-dihydro-5H-pyrrolizin-2-yl)-propan-2-ol The solution of 2,2,2-trifluoro-1-(3-methyl-1-phenyl-6,7-dihydro-5H-pyrrolizin-2-yl)-ethan-1-one (1.8 g, 6 mmol) in THF (70 ml) is treated successively with trifluoromethyltrimethylsilane (7.5 ml, 2 M in THF, 15 mmol) and tetrabutylammonium fluoride (bound to silica gel, 1.1 mmol/g of SiO$_2$; 0.5 g, 0.55 mmol) and stirred at 40° C. for 2 h (TLC: SiO$_2$/hexane-diethyl ether 1:1; starting material Rf 0.4; product Rf 8.5). The mixture is cooled in an ice bath and treated with NaOH (70 ml, 10% strength solution; 7 g, 175 mmol) and stirred at room temperature for 1 h. The THF phase is treated with diethyl ether (50 ml) and separated in a separating funnel and the aqueous phase is again extracted with diethyl ether (50 ml). The combined organic phases are washed with water (50 ml), dried over Na$_2$SO$_4$ sicc. and concentrated in vacuo.

Y: 110% (2.4 g); C$_{18}$H$_{23}$N, MW=253.39; Mp.: 106.1° C. IR (NaCl): 1/λ (cm$^{-1}$)=3522, 2958, 2924, 1603, 1423, 1303, 1263, 1223, 1203, 1132, 962, 948, 728, 710; $^1$H-NMR (CDCl$_3$): δ (ppm)=7.35–7.25 (m, 5H, arom), 3.94 (t, 2H, CH$_2$), 3.57 (s, 1H, OH), 2.67 (t, 2H, CH$_2$), 2.45 (quin +d, 4H, CH$_2$+CH$_2$CH), 2.29 (s, 3H, CH$_3$); GC-MS (EI-70 eV) m/z (rel. int. [%]=363 (97); 97 (100); 294 (98); 196 (24); 364 (19); 295 (18); 198 (17); 182 (13); 224 (12); 362 (06); 276 (06); 112 (06); 128 (05); 127 (05).

c) 5-Methyl-6-perfluoroisopropyl-7-phenyl-2,3-dihydro-1H-pyrrolizine

The solution of 1,1,1,3,3,3-hexafluoro-2-(3-methyl-1-phenyl-6,7-dihydro-5H-pyrrolizin-2-yl)propan-2-ol (2.2 g, 6 mmol) in CH$_2$Cl$_2$ abs. (25 ml) is slowly added dropwise at –50° C. to a solution of diethylaminosulphur trifluoride (DAST, 1.5 ml, 1.845 g, 11.5 mmol) in 25 ml of CH$_2$Cl$_2$ abs. The cooling bath is removed and the mixture is allowed to come to room temperature in the course of 2 h with stirring (TLC: SiO$_2$/hexane-diethyl ether 1:1; starting material Rf 0.4; product Rf 8.5). The mixture is cooled in an ice bath and rendered alkaline with NaHCO$_3$ solution (30 ml) and stirred for 10 min. The CH$_2$Cl$_2$ phase is separated in a separating funnel and the aqueous phase is again extracted with diethyl ether (50 ml). The combined organic phases are washed with satd. sodium chloride solution (50 ml), dried over Na$_2$SO$_4$ sicc. and concentrated in vacuo. The residue is purified by CC: SiO$_2$/hexane-diethyl ether 2:1; starting material Rf 0.3; product Rf 0.5).

Y: 69.9% (1.53 g); C$_{17}$H$_{14}$F$_7$N, MW=365.30; Mp: 63.10° C. IR (NaCl): 1/λ (cm$^{-1}$)=2964, 2360, 1606, 1423, 1304, 1275, 1234, 1217, 1134, 966, 729, 706; $^1$H-NMR (CDCl$_3$): δ (ppm)=7.3–7.19 (m, 5H, arom), 3.93 (t, 2H, CH$_2$), 2.68 (t, 2H, CH$_2$), 2.46 (quin+d, 4H, CH$_2$+CH$_3$CH), 2.29 (s, 3H, CH$_3$); GC-MS (EI-70 eV) m/z (rel. int. [%]=365 (100); 296 (57); 276 (26); 366 (19); 364 (15); 297 (11); 100(09); 268 (08); 212 (08); 196 (08); 207 (07); 199 (07); 294 (06); 227 (06); 226 (06); 277 (05); 114 (05).

d) 4-(5-Methyl-6-perfluoroisopropyl-7-phenyl-2,3-dihydro-1H-pyrrolizin-1-yl)benzenesulphonamide 5-Methyl-6-perfluoroisopropyl-7-phenyl-2,3-dihydro-1H-pyrrolizine (0.7 g, 1.9 mmol) is introduced into chlorosulphonic acid (2.6 ml, 4.54 g, 39 mmol) at –30° C. The mixture is warmed to 0–10° C. during the course of 2.5 h and then stirred for 42 h at RT until conversion into the acid chloride is complete. The monitoring of the reaction is carried out by means of HPLC. After this time, about 75% of the substance employed is present as sulphochloride in addition to 5% sulphonic acid and about 4% of starting material (TLC: SiO$_2$, ether-hexane 1:1, starting material Rf 0.7, sulphonic acid Rf 0, chlorosulphonic acid Rf 0.4). The reaction mixture is quenched on ice water (20 ml) and the ice-water phase is extracted 3 times with CHCl$_3$ (3×40 ml). The collected CHCl$_3$ extracts are washed (100 ml of satd. NaCl solution), dried (Na$_2$SO$_4$ sicc.) and concentrated (residue: 0.94 g, 94%, concentration according to HPLC: 88%). The chlorosulphonation product is dissolved in THF abs. (30 ml) and conc. NH$_4$OH (25% strength, 3 ml) is added with ice-cooling. The mixture is stirred at RT for 1 h, treated with semi-concentrated NaCl solution (60 ml) and extracted 3 times with ethyl acetate (3×50 ml). The ethyl acetate phase is dried (Na$_2$SO$_4$ sicc.) and concentrated. The residue (0.91 g, concentration 83.5% according to HfPLC, 90% yield) is first crystallized from aqueous EtOH (50% G/G; 6 ml) (concentration according to HPLC: 89.5%) and then crystallized from absolute ethanol (4 ml) and dried: (0.25 g, concentration according to HPLC: 96.8%). A further 0.15 g was obtained from the mother liquor (96% according to HPLC).

Y: 47.4%, (0.4 g), C$_{17}$H$_{15}$F$_7$N$_2$O$_2$S, MW=444.37; Mp: 199.60° C. IR (NaCl): 1/λ (cm$^{-1}$)=3340, 3253, 1598, 1338, 1276, 1221, 1162, 1145, 1132, 1092, 982, 968, 841, 739, 729, 551; $^1$H-NMR (DMSO-d6): δ (ppm)=7.85 and 7.37 (AA'BB', arom, 4H,J=8.4), 4.85 (NH$_2$), 3.95 (t, 2H, CH$_2$, J=7.0), 2.68 (t, 2H, CH$_2$, J=7.0), 2.49 (quin, 2H, CH$_2$, J=7.0), 2.29 (s, 3H, CH$_3$); GC-MS (El, 70 eV): m/z (rel int. %)=444 (100); 226 (52); 295 (50); 445 (21); 345 (11); 443 (09); 296 (09); 227 (09); 446 (07); 275 (07); 225 (07); 364 (06); 294 (05)

EXAMPLE 40

4-[2-(1,1,1,2,2,3,3-Heptafluoro-4-butyl)-3-methyl-6,7-dihydro-5H-pyrrolizin-1-yl]benzene-sulphonamide a) 1,1,1,2,2,3,3-Heptafluoro-4-(3-methyl-1-phenyl-6,7-dihydro-5H-pyrrolizin-2-yl)butan-4-one 5-Methyl-7-phenyl-2,3-dihydro-1H-pyrrolizine (Example 30 c, 1.0 g, 0.005 mol), dissolved in dichloroethane (20 ml) is treated with heptafluorobutyryl chloride (0.83 ml, 1.3 g, 0.0055 mol) at RT and finally tin tetrachloride (0.7 ml, 1,56 g, 0.006 mol) in dichloroethane (5 ml) is added dropwise. The mixture warms to 35° C. and is stirred at RT for 16 h. The GC-MS analysis shows a 60% reaction. The reaction mixture is rendered alkaline with NaOH (25%, 25 ml) in an ice bath and, after addition of CH$_2$Cl$_2$ (25 ml), the organic phase is separated in a separating funnel. The alkali phase is extracted a further two times with dichloromethane (2×20 ml). These CH$_2$Cl$_2$ extracts are combined, dried over Na$_2$SO$_4$ sicc. and evaporated to dryness in vacuo.

The residue (1.4 g) is purified by CC (SiO$_2$ (120 g), hexane-diethyl ether 7:3): 0.46 g of starting material are recovered in the forerun. In a second separation process, 0.180 g are obtained from an intermediate fraction and, in the afterrun of the first separation, 0.62 g of product, together 0.8 g (40.7% of theory).

Y: 40.7% (0.8 g); C$_{18}$H$_{14}$F$_7$NO, MW=393.31; Mp: 77.0° C., IR (NaCl): 1/λ (cm$^{-1}$)=1667, 1505, 1422, 1384, 1343, 1239, 1213, 1175, 1117, 1093, 870, 764, 717, 703; $^1$H-NMR (CDCl$_3$): δ (ppm)=7.37 (m, 5H, arom), 3.95 (t, 2H, CH$_2$), 2.89 (t, 2H, CH$_2$), 2.53 (quin, 2H, CH$_2$), 2.39 (s, 3H, CH$_3$); GC-MS (El, 70 eV): m/z (rel. int. %)=224.1 (100); 393.1 (35); 225.1 (18); 394.1 (07); 127.0 (06).

b) 2-(1,1,1,2,2,3,3-Heptafluoro-4-butyl)-3-methyl-1-phenyl-6,7-dihydro-5H-pyrrolizine The solution of 1,1,1,2,2,3,3-heptafluoro-4-(3-methyl-1-phenyl-6,7-dihydro-5H-pyrrolizin-2-yl)-butan-4-one (0.62 g, 1.6 mmol) in dichloroethane (20 ml) is treated successively with NaCNBH$_3$ (0.42 g, 6.4 mmol) and ZnI$_2$ (0.71 g, 2.24 mmol) and refluxed for 4 days (d). After 2 days, NaCNBH$_3$ (0.42 g, 6.4 mmol) and ZnI$_2$ (0.71 g, 2.24 mmol) are again added. The reaction is observed by means of GC-MS. After 2 days, 40% of the compound employed is reacted, and after 4 days 89%, in addition to a further 11% of starting material. The reaction is then terminated by addition of dilute phoshoric acid (8%, 50 ml). After the evolution of gas has ended, the mixture is extracted with methylene chloride, the organic phase is washed with water (50 ml) and the solvent is stripped off in vacuo after drying over Na$_2$SO$_4$ sicc. The residue (0.65 g, 82.4%, 77% strength according to GC-MS(TIC)) is employed in the subsequent reaction without further purification.

Y: 82.4% (0.65 g, 77% according to GC-MS (TIC)); C$_{18}$H$_{16}$F$_7$N, MW=379.32; Mp: 95.4° C. IR (NaCl): 1/λ (cm$^{-1}$)=2928, 1604, 1446, 1425, 1352, 1221, 1112, 1059, 963, 763, 745, 702; $^1$H-NMR (CDCl$_3$): δ (ppm)=7.36–7.20 (m, 5H, arom), 3.91 (t, 2H, CH$_2$, J=7.1), 3.28 (t, 2H, CH$_2$, J=20.0), 2.93 (t, 2H, CH$_2$, J=7.1), 2.47 (q, 2H, CH$_2$, J=7.1), 2.21 (s, 3H, CH$_3$); MS(EI, 70 eV): m/z (rel int. %)=379 (56); 210 (100); 211 (17); 208 (13); 380 (12).

c) 4-[2-(1,1,1,2,2,3,3-Heptafluoro-4-butyl)-3-methyl-6,7-dihydro-5H-pyrrolizin-1-yl]benzene-sulphonamide 2-(1,1,1,2,2,3,3-Heptafluoro-4-butyl)-3-methyl-1-phenyl-6,7-dihydro-5H-pyrrolizine (0.45 g, 77%, 1.1 mmol) is dissolved in CHCl$_3$ abs. (3 ml), the solution is cooled to 0° C. and chlorosulphonic acid (0.66 ml, 1.15 g, 10 mmol) is slowly added dropwise. The mixture is heated for 2.5 h (58–61° C.) (TLC: SiO$_2$, ether-hexane 1:1, starting material Rf 0.8, sulphonic acid Rf 0.0, chlorosulphonic acid Rf 0.5). The reaction mixture is quenched on ice (20 ml), extracted 3 times with CHCl$_3$ (3×25 ml) and the collected CHCl$_3$ solution is washed (30 ml of satd. NaCl solution), dried (Na$_2$SO$_4$ sicc.) and concentrated (residue: 1.0 g). The chlorosulphonation product (1.0 g) is dissolved in THF abs. (10 ml) and conc. NH$_4$OH (25% strength, 2,5 ml) is slowly added dropwise. The mixture is stirred at RT for 16 h, treated with semi-concentrated NH$_4$Cl solution (20 ml) and extracted 3 times with ethyl acetate (3×50 ml). The washed (40 ml of satd. NaCl solution) ethyl acetate phase is dried (Na$_2$SO$_4$ sicc.) and concentrated. The residue (0.3 g) is separated on SiO$_2$ (30 g) using ether as an eluent: from fractions 3–6:0.15 g, (concentration 87%) and then washed 2×with ether (0.5 ml) and dried: 0.09 g (90.2% according to HPLC)

Fractions 7–10:0.05 g (91.2% According to HPLC).

Y: 29.7%, (0.14 g, concentration 90.7%), C$_{18}$H$_{17}$F$_7$N$_2$O$_2$S, MW=458.4; Mp: 220.7° C. IR (NaCl): 1/λ (cm$^{-1}$)=3344, 3247, 1597, 1352, 1334, 1217, 1113, 1053, 747, 545; $^1$H-NMR (DMSO-d6): δ (ppm)=7.89 and 7.39 (AA'BB', 4H, arom, J=8.6), 5.96 (s, 2H, NH$_2$), 3.93 (t, 2H, CH$_2$, J=7.0), 3.30 (t, 2H, CH$_2$, J=19.8), 2.93 (t, 2H, CH$_2$, J=7.1), 2.53 (q, 2H, CH$_2$, J=7.1), 2.21 (s, 3H, CH$_3$).

The compound of Example 41 is prepared according to analogous procedures.

Biological Activity

Test System for Determining the Inhibition of 5-lipoxygenase

Human granulocytes are used as a source of 5-lipoxygenase. LTB$_4$ (leukotriene B$_4$) is formed from endogenous arachidonic acid by stimulation with calcium ionophore A 23187. The granulocytes are isolated and the enzyme reaction is carried out according to known processes (see Arch. Pharm. 330, 307–312 (1997)).

The blood protected from clotting with heparin is centrifuged over a discontinuous Percoll®-gradient and the granulocyte layer is pipetted off. After lysis of the erythrocytes, the granulocytes are washed repeatedly and then maintained at a specific cell count. The enzyme reaction is then started with calcium ionophore A 23187 in the presence or absence of the test substance after addition of Ca$^{2+}$. The synthesis of the leukotrienes is stopped after 1.5 minutes. The samples are centrifuged off and the supernatant is diluted. LTB$_4$ is determined quantitatively by means of ELISA.

Test System for Determining the Inhibition of cyclooxygenase-1

In this test system, the amount of prostaglandin E$_2$ formed from human platelets after addition of calcium ionophore is determined by means of ELISA. In this process, the platelets are obtained after centrifugation over a discontinuous Percoll® gradient. The enzyme reaction and the determination of the metabolites formed is carried out in principle as in the case of the determination of the inhibition of 5-lipoxygenase. Differences exist with respect to the incubation time. Furthermore, the addition of a thromboxane synthase inhibitor is necessary (see Arch. Pharm. Med. Chem. 330, 307–312 (1997)).

Test System for Determining the Inhibition of cyclooxygenase-2

$COX_2$ (from placenta of sheep) is preincubated at 4° C. for 10 min with test substance, then stimulated with arachidonic acid (5 μM) at 25° C. for 10 min. Diclofenac ($IC_{50}$ ($COX_2$)=3.0×10$^{-6}$ M) is used as a reference. The determination is carried out in 3 dilutions (10$^{-7}$, 10$^{-6}$, 10$^{-5}$ M). The $PGE_2$ concentrations are quantified by means of ELISA (see Mitchell J. A, et al. Proc. Nat. Acad. Sci. 90: 11693–11697 (1993)).

What is claimed is:

1. [α]-Fused pyrrole compounds of formula 1

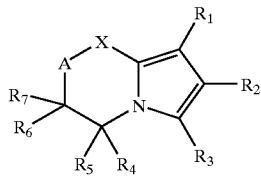

Formula 1 in which

X is CR8R9 or C(O);

A is CR10R11 or a bond between X and an atom carrying radicals R6 and R7;

one of the radicals R1, R2, R3 is 4-substituted phenyl, the substituent being selected from $C_{1-4}$-alkylthio, $C_{1-4}$-alkylsulfinyl, $C_{1-4}$-alkylsulfonyl, sulphamoyl, N—$C_{1-4}$-alkylsulphamoyl, N,N-di-$C_{1-4}$-alkylsulfamoyl, $C_{1-4}$-alkylsulphonamido or $C_{1-4}$-alkylsulphone-N—$C_{1-4}$-alkylamido;

a second of the radicals R1, R2, R3 is $C_{1-6}$-alkyl, $C_{1-6}$-alkyl substituted by identical or different substituents selected from halogen, $C_{3-7}$-cycloalkyl, $C_{1-4}$-alkoxy, trifluoromethoxy, hydroxyl, or trifluoromethyl, $C_{3-7}$-cycloalkyl, $C_{3-7}$-cycloalkyl substituted by identical or different substituents selected from halogen, $C_{1-4}$-alkyl, halo-$C_{1-4}$-alkyl, $C_{3-7}$-cycloalkyl, $C_{1-4}$-alkoxy, halo-$C_{1-4}$-alkoxy or hydroxyl, phenyl, phenyl substituted by identical or different substituents selected from halogen, $C_{1-4}$-alkyl, halo-$C_{1-4}$-alkyl, $C_{1-4}$-alkoxy, halo-$C_{1-4}$-alkoxy, $C_{1-4}$-alkylthio, hydroxyl, nitro, $C_{1-4}$-alkylsulfinyl, $C_{1-4}$-alkylsulfonyl, sulphamoyl, N—$C_{1-4}$-alkylsulphamoyl, N,N-di-$C_{1-4}$-alkylsulfamoyl, $C_{1-4}$-alkylsulphonamido or $C_{1-4}$-alkylsulphone-N—$C_{1-4}$-alkylamido; or a mono- or bicyclic aromatic, mono- or bicyclic non-aromatic, heterocyclic radical which contains 1, 2, or 3 heteroatoms independently of one another selected from N, O and S, heterocyclic radical which contains 1, 2, or 3 heteroatoms independently of one another selected from N, O and S substituted by identical or different substituents selected from halogen, $C_{1-4}$-alkyl, halo-$C_{1-4}$-alkyl, $C_{1-4}$-alkoxy, halo-$C_{1-4}$-alkoxy, $C_{1-4}$-alkylthio, hydroxyl, nitro, $C_{1-4}$-alkylsulfinyl, $C_{1-4}$-alkylsulfonyl, sulphamoyl, N—$C_{1-4}$-alkylsulphamoyl, N,N-di-$C_{1-4}$-alkylsulfamoyl, $C_{1-4}$-alkylsuphonamido or $C_{1-4}$-alkylsulphone-N—$C_{1-4}$-alkylamido;

a third of the radicals R1, R2, R3 is

H, $C_{1-4}$-alkyl, halo-$C_{1-4}$-alkyl, hydroxy-$C_{1-6}$-alkyl, —CHO, —COOH, —COCOOH, —COO—$C_{1-4}$-alkyl, —COO—$C_{1-4}$-Alkphenyl, —COCOO—$C_{1-4}$-alkyl, halogen, cyano, $C_{1-4}$-alkylsulphonyl, suiphamoyl or B—Y;

in which

B is $C_{1-8}$-alkylene or $C_{2-8}$-alkenylene;

Y is —COOH, —COO—$C_{1-4}$-alkyl, —SO$_3$—$C_{1-4}$-alkyl, —CHO or hydroxyl; or the second and third of the radicals R1, R2, R3, together with the C atoms to which they are bonded, form a saturated or unsaturated $C_3$–$C_7$-cycloalkyl;

R4–R11, which can be identical or different, are hydrogen, $C_{1-6}$-alkyl, hydroxy-$C_{1-6}$-alkyl, $C_{1-4}$-alkoxy-$C_{1-6}$-alkyl, hydroxyl, COOH or acyloxy, where vicinal radicals can also represent bonds or geminal radicals, also together with the C atom to which they are bonded, can represent carbonyl or $C_3$–$C_7$-cycloalkyl;

and optical isomers, physiologically tolerable salts and physiologically hydrolysable esters thereof.

2. Compounds according to claim 1, in which X is CR8R9, A is a bond between X and the atom carrying the radicals R6 and R7 and R4, R5, R6, R7, R8, R9, which can be identical or different, are hydrogen or $C_{1-4}$-alkyl.

3. Compounds according to claim 1, in which the second of the radicals R1, R2, R3 is 4-substituted phenyl.

4. Compounds according to claim 3, in which the substituent is fluorine, methyl or trifluoromethyl.

5. Compounds according to claim 1, in which the second of the radicals R1, R2, R3 is $C_{1-6}$-alkyl, $C_{3-7}$-cycloalkylmethyl or $C_{3-7}$-cycloalkyl.

6. Compounds according to claim 1, in which the second of the radicals R1, R2, R3 is polyfluorinated $C_{1-6}$-alkyl, $C_{3-7}$-cycloalkylmethyl or $C_{3-7}$-cycloalkyl.

7. Compounds according to claim 1, in which the third of the radicals R1, R2, R3 is hydrogen, $C_{1-6}$-alkyl, CF$_3$ or halogen.

8. Compounds according to claim 1, in which the first and the second of the radicals R1, R2, R3 are vicinal to one another.

9. Compounds according to claim 1, in which R1 is the first of the radicals R1, R2, R3.

10. Pharmaceutical composition, comprising at least one compound according to claim 1, together with pharmaceutically acceptable excipients.

11. A method of treatment of disorders of rheumatic type, comprising administering to a patient in need of such treatment a compound according to claim 1.

12. Compounds according to claim 1, wherein at least one of said $C_{1-6}$-alkyl, $C_{3-7}$-cycloalkyl, phenyl, or heterocyclic radical is mono-, di- or tri-substituted.

13. Compounds according to claim 1, wherein at least one of said mono- or bicyclic-aromatic, or mono- or bicyclic-non-aromatic is benzo-fused.

14. Compounds according to claim 1, wherein at least one of said $C_{1-8}$-alkylene or $C_{2-8}$-alkenylene is substituted by hydroxyl or $C_{1-4}$-alkoxy.

* * * * *